(12) United States Patent
Gray et al.

(10) Patent No.: US 11,841,360 B1
(45) Date of Patent: Dec. 12, 2023

(54) SYSTEMS, DEVICES, AND METHODS FOR EX VIVO ASSESSMENT OF RESPONSES TO MULTIPLE THERAPEUTIC AGENTS

(71) Applicant: Oregon Health & Science University, Portland, OR (US)

(72) Inventors: Joe Gray, Portland, OR (US); Zuzana Tatárová, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 1001 days.

(21) Appl. No.: 16/400,012

(22) Filed: Apr. 30, 2019

Related U.S. Application Data

(60) Provisional application No. 62/664,907, filed on Apr. 30, 2018.

(51) Int. Cl.
| | | |
|---|---|---|
| *G01N 1/00* | (2006.01) |
| *G01N 33/50* | (2006.01) |
| *C12M 3/00* | (2006.01) |
| *G01N 1/36* | (2006.01) |
| *G01N 1/30* | (2006.01) |
| *C12M 1/12* | (2006.01) |

(52) U.S. Cl.
CPC ......... *G01N 33/5011* (2013.01); *C12M 21/08* (2013.01); *C12M 23/06* (2013.01); *G01N 1/30* (2013.01); *G01N 1/36* (2013.01)

(58) Field of Classification Search
None
See application file for complete search history.

(56) References Cited

U.S. PATENT DOCUMENTS 10,183,155 B2 * 1/2019 Tepper ............... A61B 10/0266

OTHER PUBLICATIONS

Chang, et al., "Multiplexed Immunohistochemistry Image Analysis using Sparse Coding," Proc. Annu. Int. Conf. IEEE Eng. Med. Biol. Soc. EMBS, 2017, pp. 4046-4049.

Feeley, et al., "Galectin-3 directs antimicrobial guanylate binding proteins to vacuoles furnished with bacterial secretion systems," PNAS, vol. 114, No. 9, 2017, pp. E1698-E1706.

Jenkins, et al., "Ex Vivo Profiling of PD-1 Blockade Using Organotypic Tumor Spheroids," Cancer Discov., vol. 8, No. 2, 2017, pp. 197-212.

(Continued)

*Primary Examiner* — Jyoti Nagpaul
(74) *Attorney, Agent, or Firm* — Lee & Hayes, P.C.; Tanya M. Harding

(57) ABSTRACT

Provided is an ex vivo system allowing for assessment of tumor and other cell responses to pluralities of agents or agent combinations using a microdose delivery microdevice implanted into an ex vivo tissue sample. The microdevice permits localized intra-tissue sample agent delivery and provides the ability to predict the drug efficacy within days after application. Systems for maintaining tissue samples ex vivo over hours to weeks are provided, which can be used to house tissue samples during exposure of the tissue to microdoses of agents applied using the delivery microdevices. Also provided are biomarkers (galectin and/or neuropilin) useful in evaluating the efficacy of agents.

16 Claims, 33 Drawing Sheets
(24 of 33 Drawing Sheet(s) Filed in Color)

(56) References Cited

OTHER PUBLICATIONS

Jonas, et al., "An implantable microdevice to perform high-throughput in vivo drug sensitivity testing in tumors," Sci. Transl. Med., vol. 7, No. 284, p. 284ra57, 2015, 13 pages; as corrected in "Erratum for the Research Article: An implantable microdevice to perform high-throughput in vivo drug sensitivity testing in tumors," Sci. Transl. Med., vol. 11, No. 520, eaba 1552, 2019.
Tatárová, et al., "Microfluidic co-culture platform to quantify chemotaxis of primary stem cells," Lab Chip, vol. 16, No. 10, 2016, pp. 1934-1945.
Tsujikawa, et al., "Quantitative Multiplex Immunohistochemistry Reveals Myeloid-Inflamed Tumor-Immune Complexity Associated With Poor Prognosis," Cell Rep., vol. 19, No. 1, 2017, pp. 203-217.
Vlachogiannis, et al., "Patient-derived organoids model treatment response of metastatic gastrointestinal cancers," Science, vol. 359, 2018, pp. 920-926.
Watson, et al., "Microenvironment-Mediated Mechanisms of Resistance to HER2 Inhibitors Differ between HER2 +Breast Cancer Subtypes," Cell Syst., vol. 6, 2018, pp. 329-342.
Tatarova, et al., "Systematic identification of synergistic combinations of targeted agents and immunotherapies in breast cancer using intratumor multiplex implantable microdevice assay," Research Square, 2021, 37 pages.

\* cited by examiner

FIG. 1A
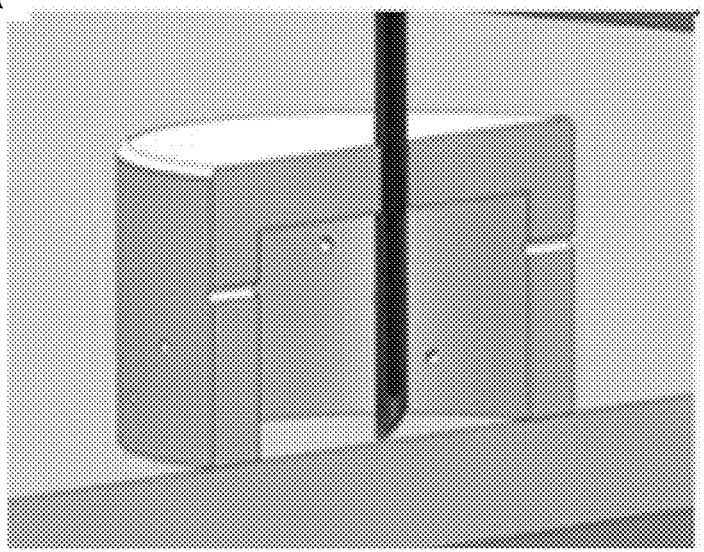
FIG. 1B
FIG. 1C
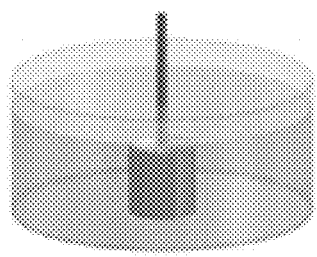
FIG. 1E
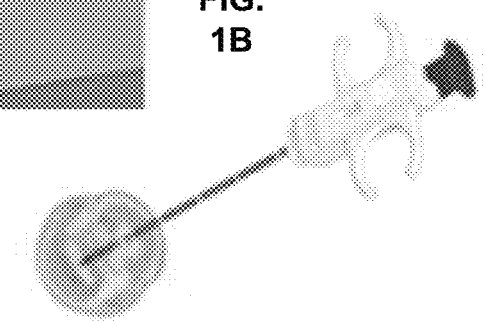
DEVICE
Tumor BIOPSY
FIG. 1D
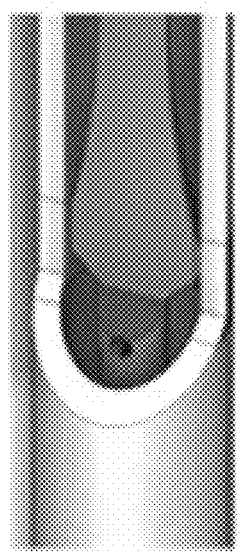
FIG. 1F
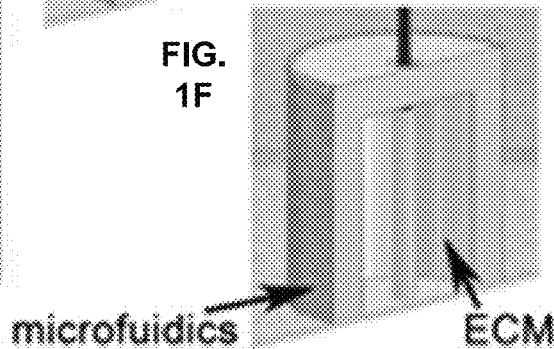
microfuidics  ECM

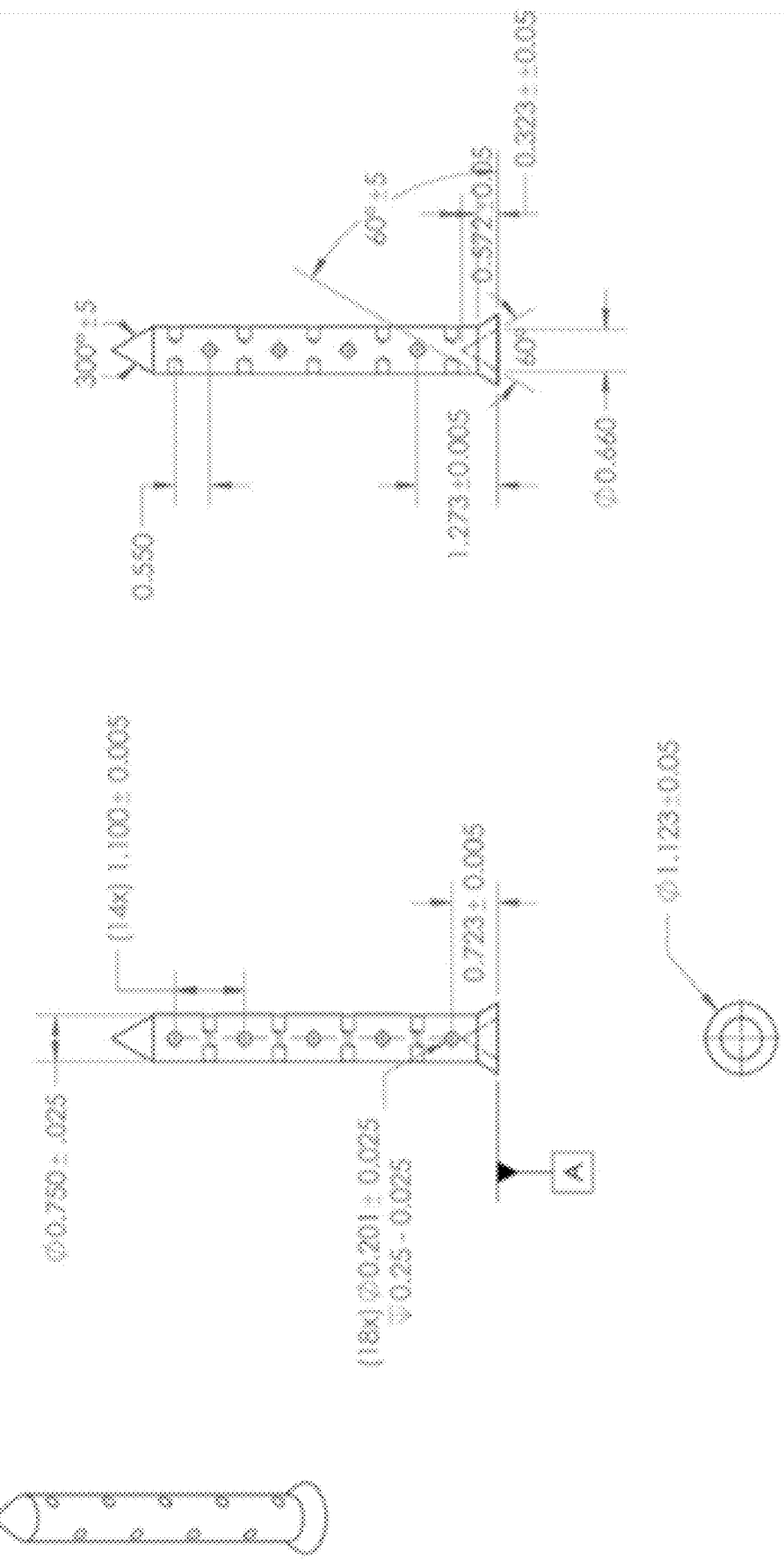

FIG.
5C
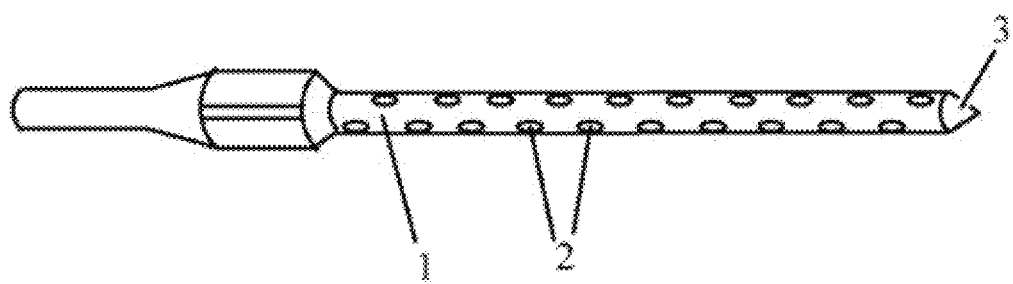

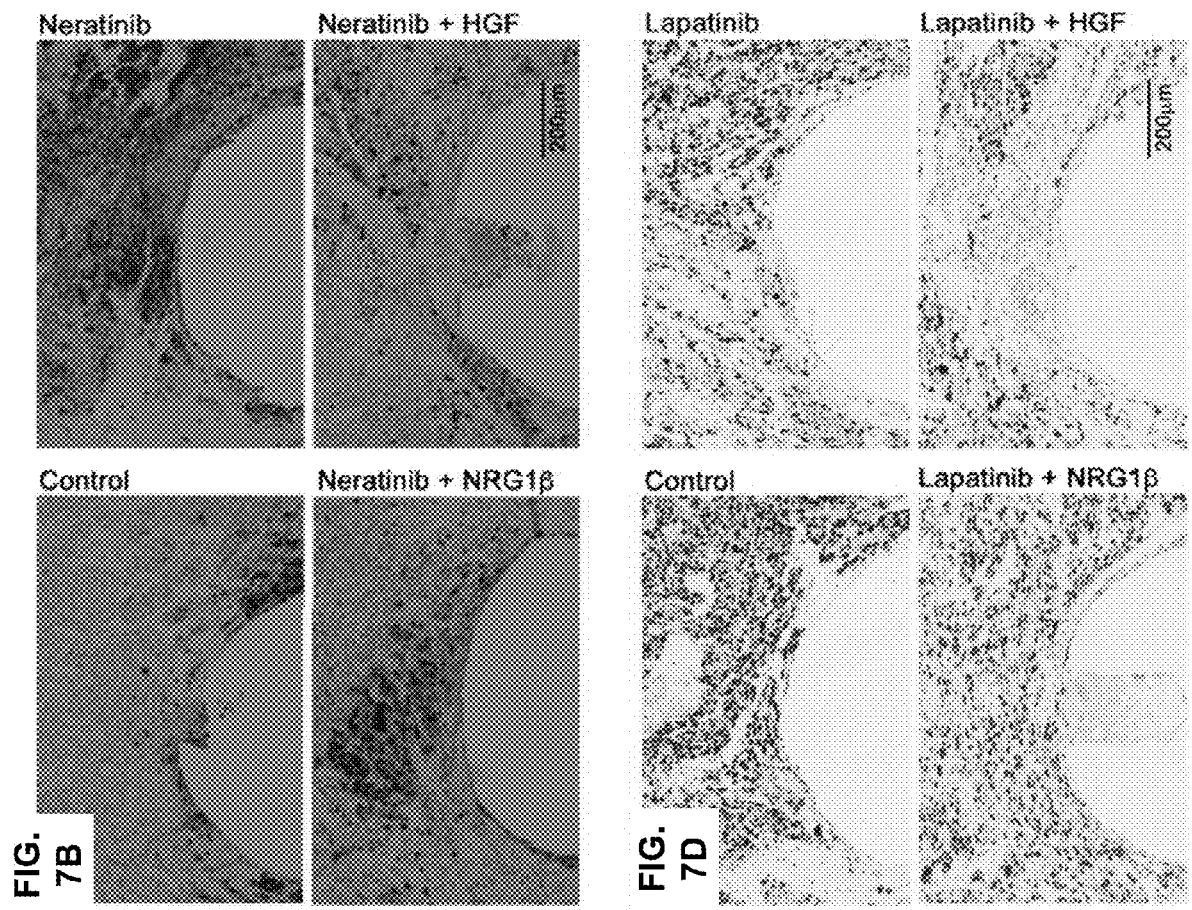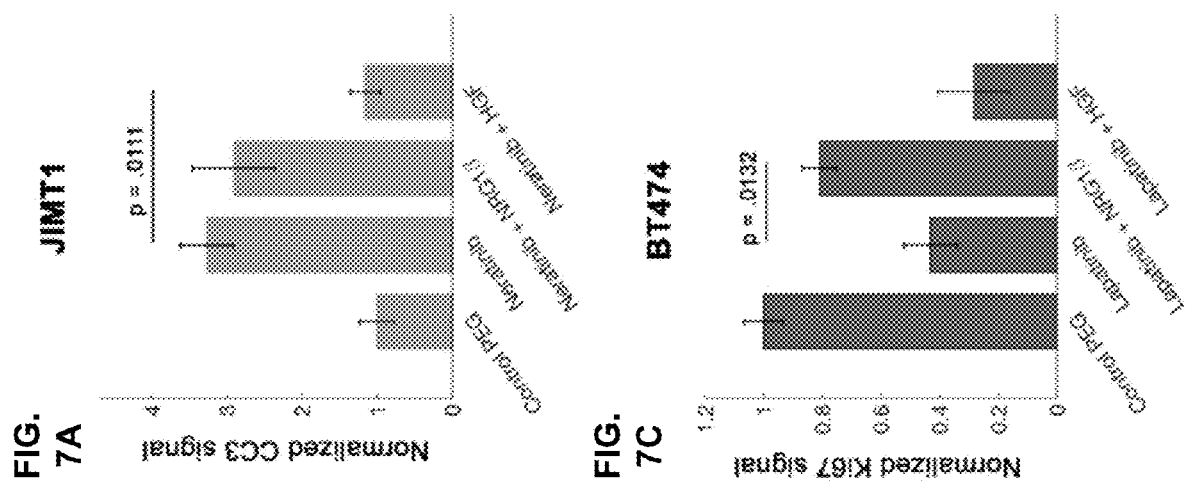

FIG. 8A
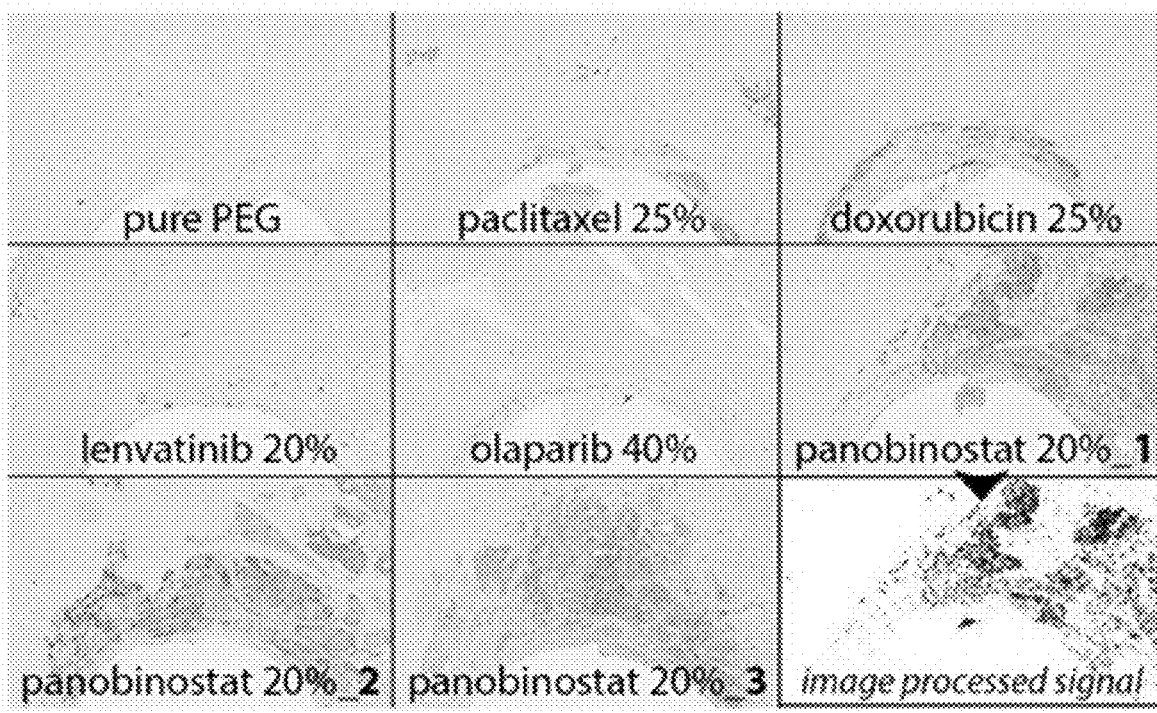
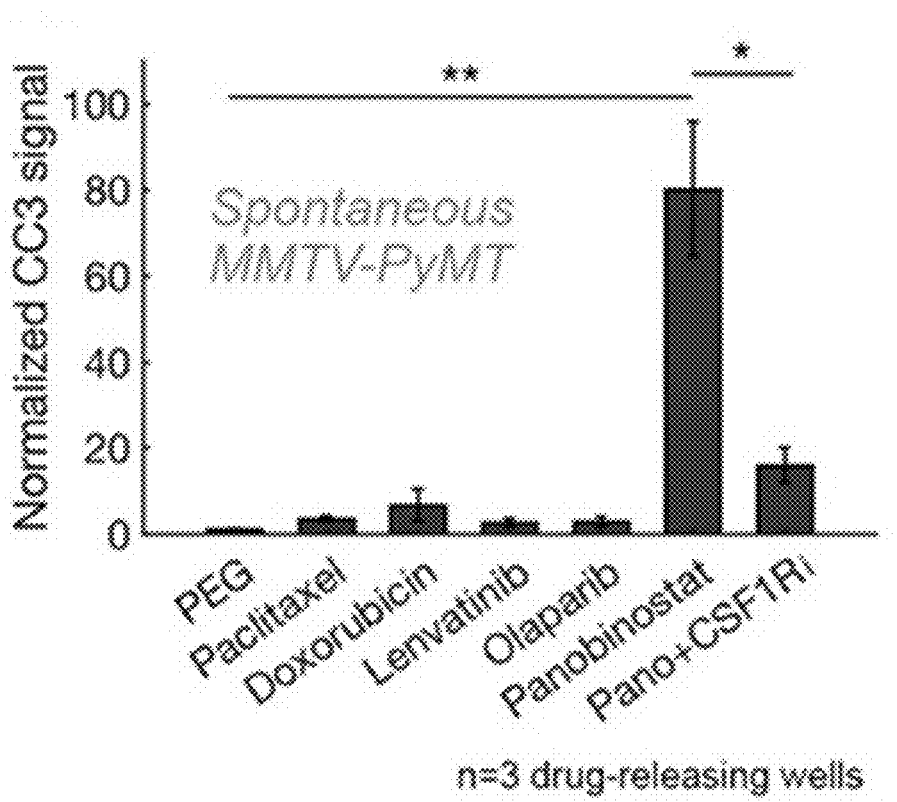

FIG. 8B

Mouse multiplex IHC panel

| Marker | Basic discrimination |
|---|---|
| Hematoxylin | nuclei |
| Ki67 | proliferation |
| CC3 | apoptosis |
| Pan-CK | Epithelial cells |
| CD45 | leukocytes |
| CD31 | Endothelial cells |
| AlphaSMA | Mesenchymal c. / EMT |
| CD3 | Pan T cells |
| CD11b | Pan-myeloid cells |
| CD4 | CD4 T cells |
| CD8 | CD8 T cells |
| GzmB | CD8 T cell activation |
| Foxp3 | Tregs |
| CSF-1R | TAMs |
| F4/80 | macrophages |
| CD11c | Dendritic cells |
| Ly6G | neutrophils |
| MHCi | Ag presentation |
| MHCii | Professional APC |
| Neuropilin-1 | Biomarker |
| Galectin-3 | Biomarker |

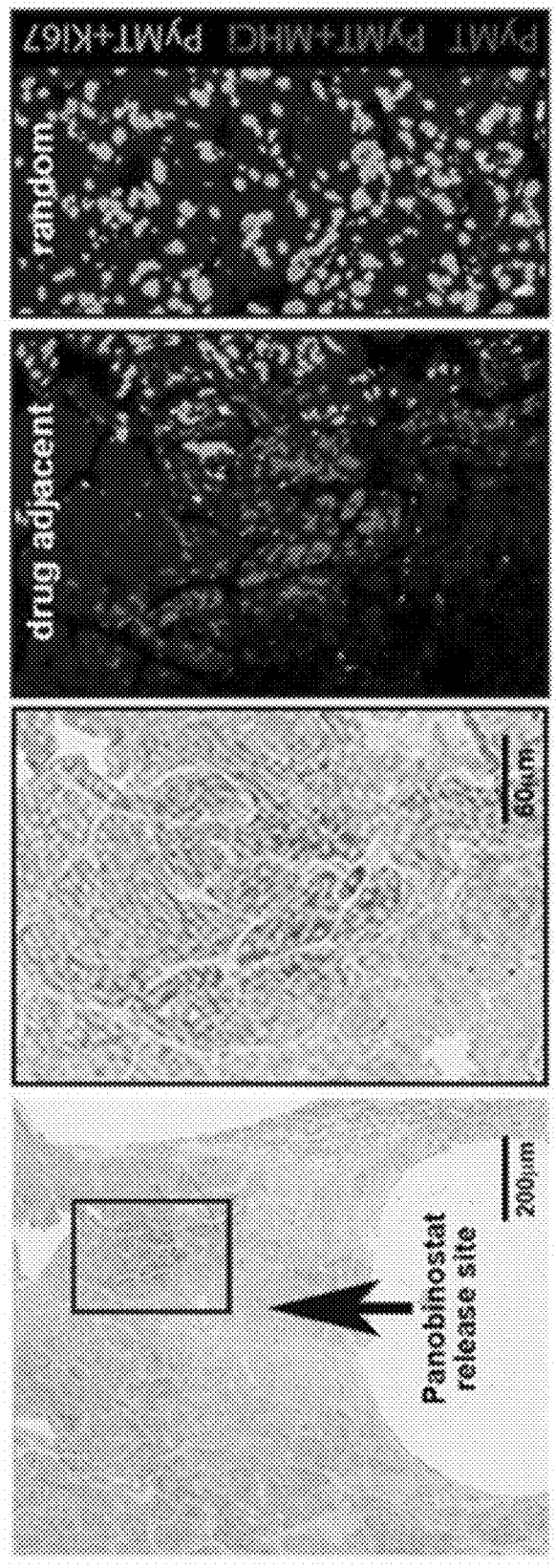
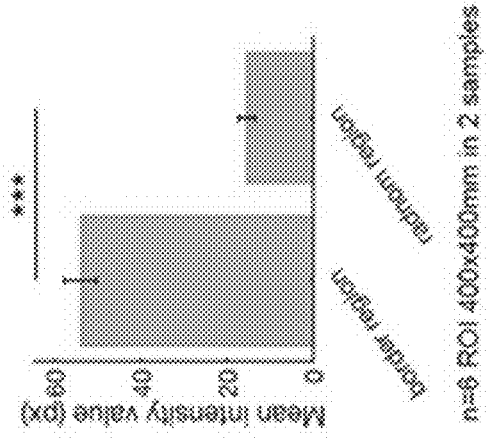
FIG. 8D

FIG. 10A
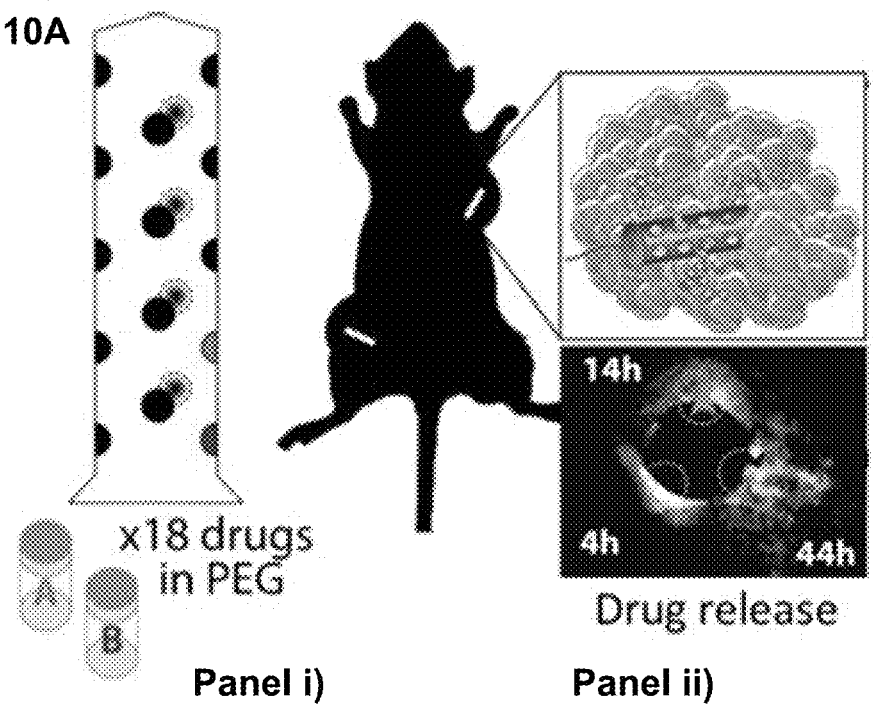
Panel i)     Panel ii)
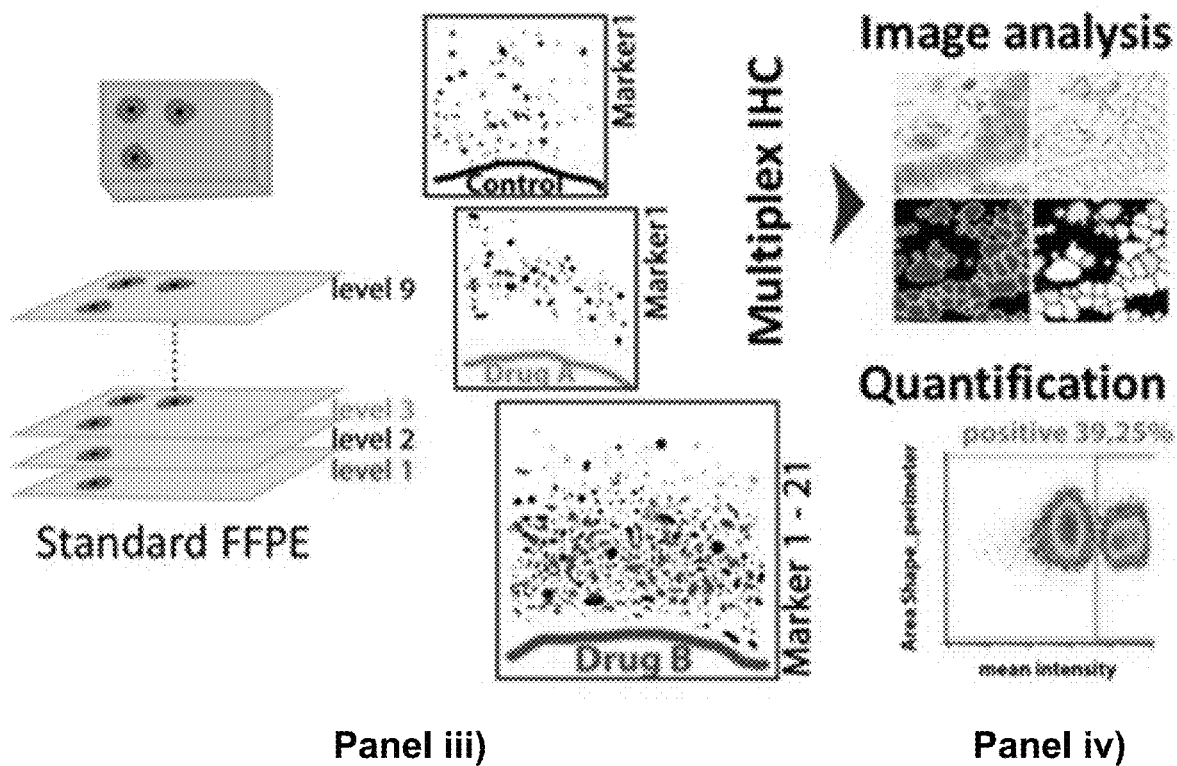
Panel iii)     Panel iv)

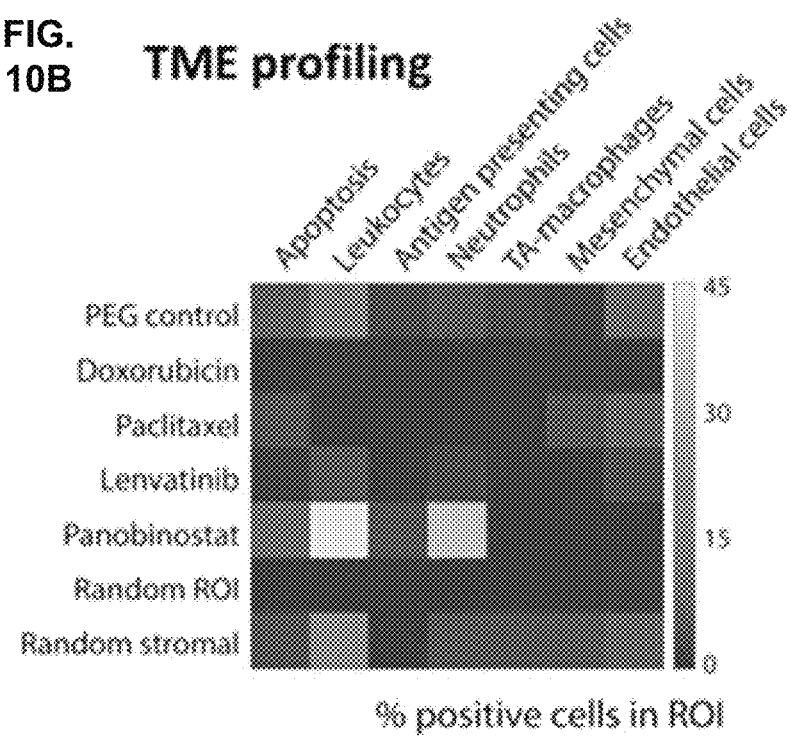
FIG. 10B TME profiling

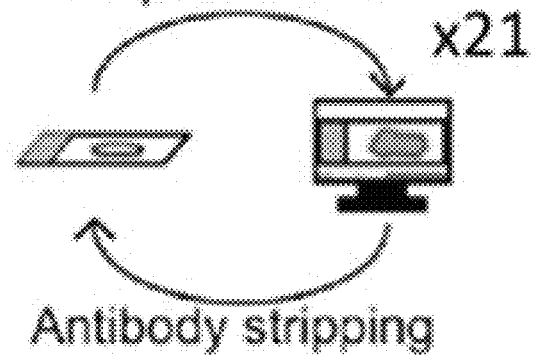
FIG. 11A
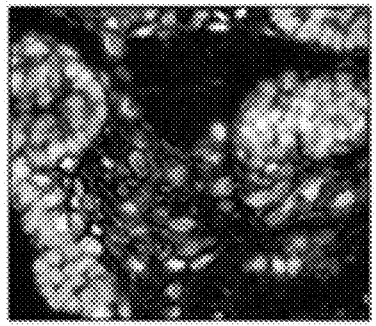
FIG. 11B
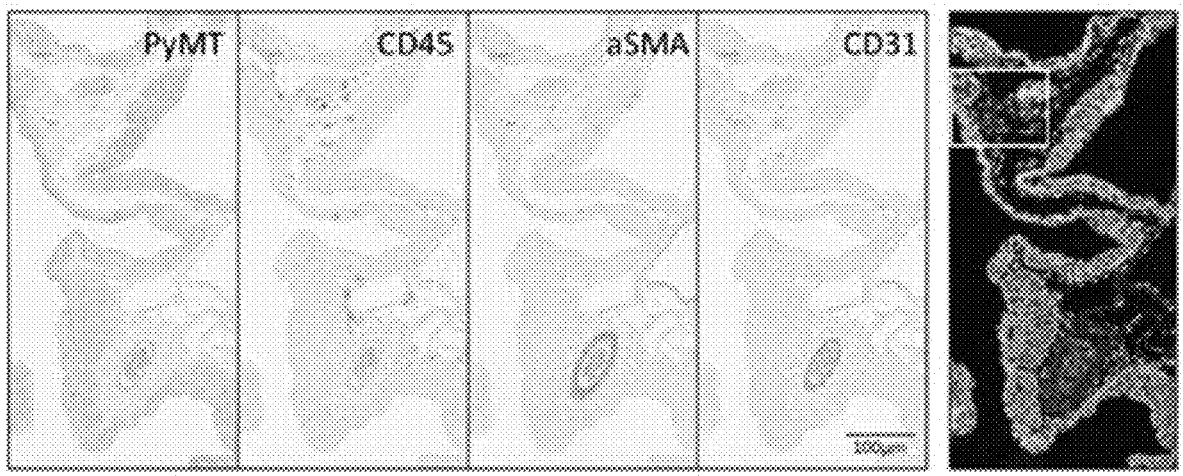

FIG. 12

| Fold change | Compound name | Function |
|---|---|---|
| 2.679 | panobinostat | pan HDACi |
| 2.605 | YC-1 | HIF-1a inhibitor |
| 2.422 | apicidin | fungal metabolite and HDACi |
| 2.29 | Trichostatin-a | class I and II HDACi |
| 1.927 | GSK-1070916 | Aurora B/C kinase inhibitor |
| 1.917 | SN-38 | active metabolite of irinotecan |
| 1.876 | Vorinostat | pan HDACi |
| 1.875 | AT-7519 | multi-CDKi → palbociclib FDA-approved |
| 1.837 | RITA | reactivation of p53 and tumor cell apoptosis |
| 1.722 | givinostat | class I and II HDACi ↘ venetoclax FDA-approved |
| 1.653 | Alvocidib | flavonoid alkaloid, multi-CDKi |
| 1.643 | Staurosporine | alkaloid, inhibition of protein kinases |
| 1.636 | Lestaurtinib | Staurosporin related |
| 0.677 | Doxorubicin | topoisomerase inhibitor, DNA intercalator |

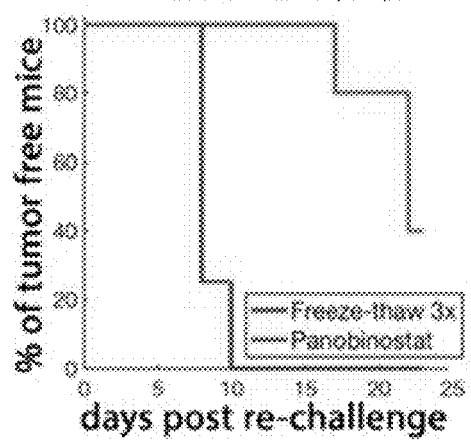
FIG. 14A Immunogenicity of panobinostat-mediated apoptosis
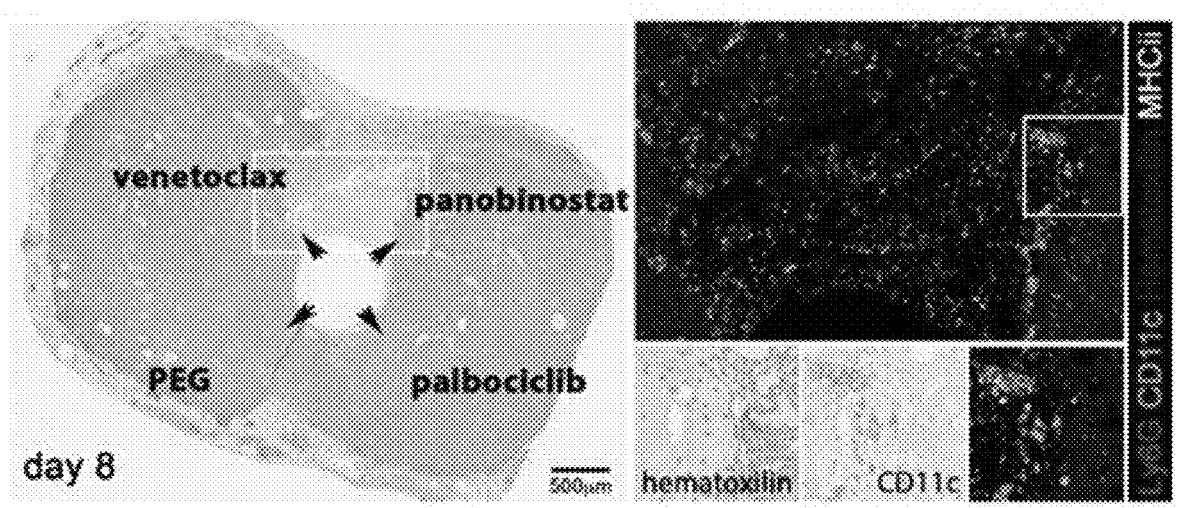
FIG. 14B Intersection of diffusing drugs identifies optimal COMBO

FIG. 16A

| Conditions | |
|---|---|
| PEG | |
| Panobinostat | |
| Pano + aGal3 | TME profiling with spatial resolution, day 2 & 3 |
| Pano + aLy6G | |
| Pano + aNRP1 | |
| aGal3 | |
| aLy6G | |
| aNRP1 | | x2 replicates/device
x2 tumors per mouse
x2 mice
8 replicates / condition
x0.75 = 6 assay areas

FIG. 16B Preliminary data, Normalized CC3 signal

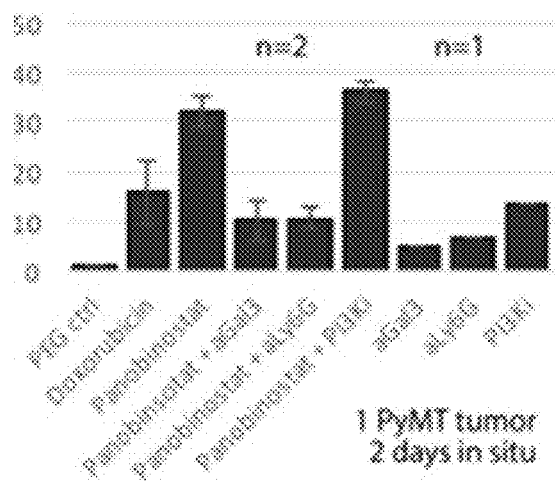

1 PyMT tumor
2 days in situ

FIG. 16C

| | | |
|---|---|---|
| extended mIHC | Galectin-3 | In vitro staining (i) |
| | Calreticulin | DAMPs hallmark (ii) |
| | LC3B, *TEM* | Autophagy (iii) |
| | ICAM-1, CC3 | Immunogenic apoptosis (iv) |
| | CXCR2, CD206 | N2 neutrophils (vi) |
| | ICAM-1 | N1 neutrophils (vii) |
| Set of interventions | a-Gal3 | All consequent phenotypes (i) |
| | 3-MA | Autophagy inhibition (iii) |
| | Pi3K | Autophagy increase (iii) |
| | IFNg | MHC-I increase (not only) (v) |
| | a-IFNGR | MHC-I decrease (v) |
| | ICAM-1 | neutrophil recruitment (vi) |
| | IFNb, TGFbi | N1 induction (vii) |
| | a-IFNAR | N1 inhibition, MHCi decrease |

FIG. 18A
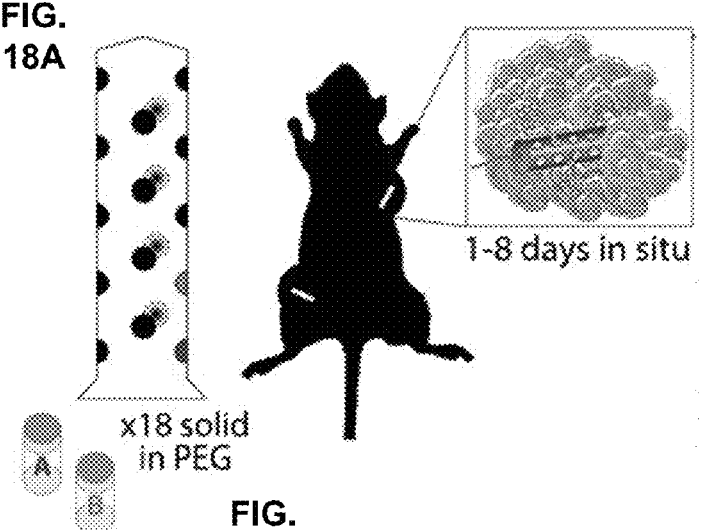
FIG. 18B
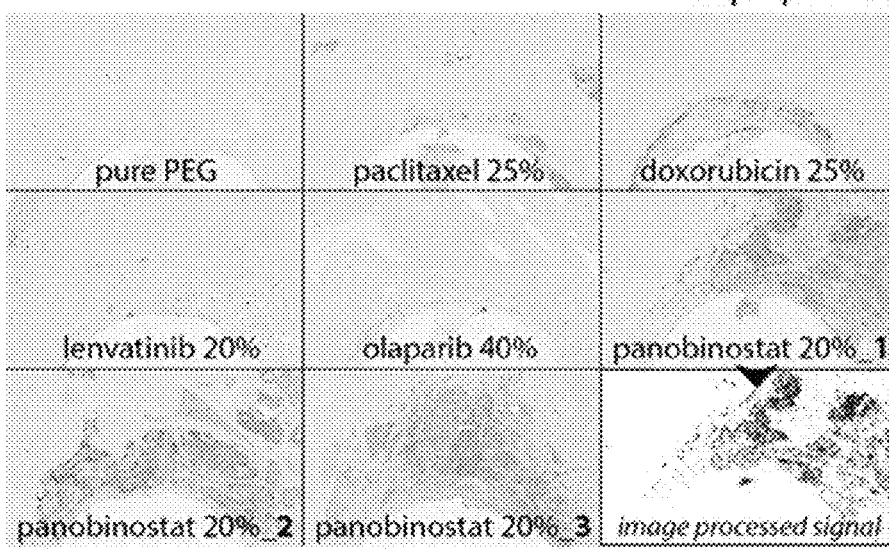
FIG. 18C TME profiling
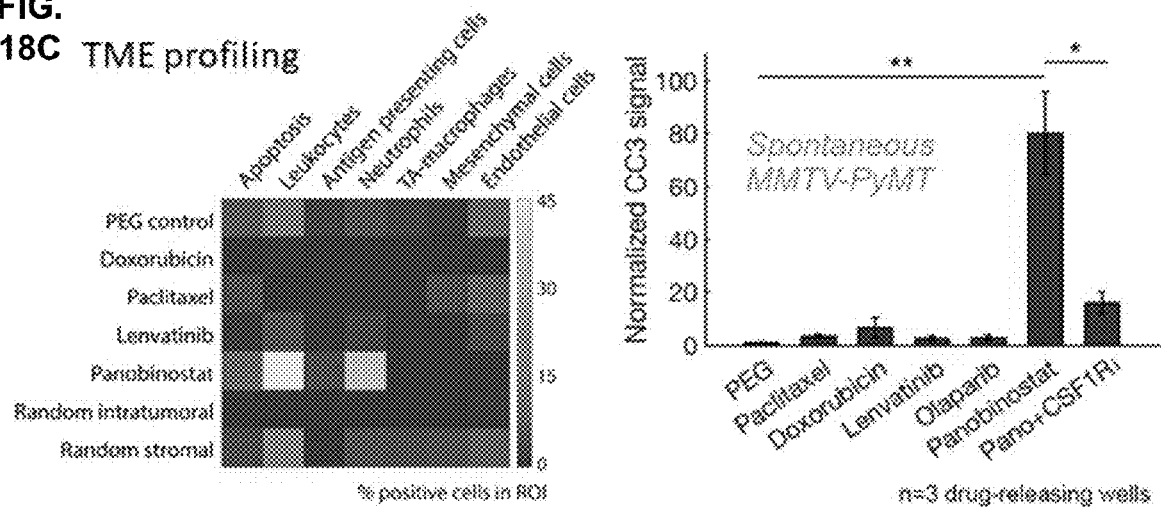

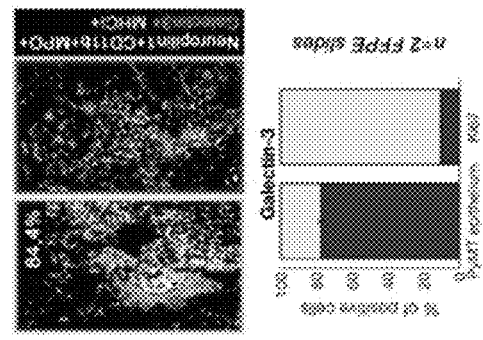
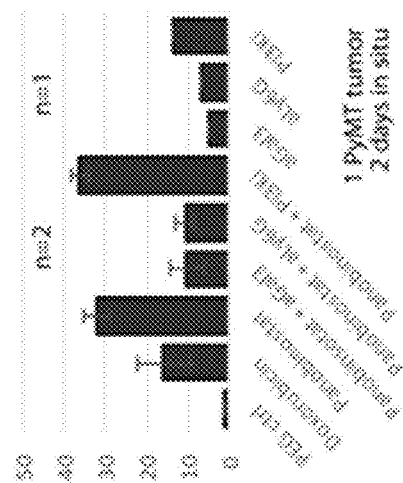
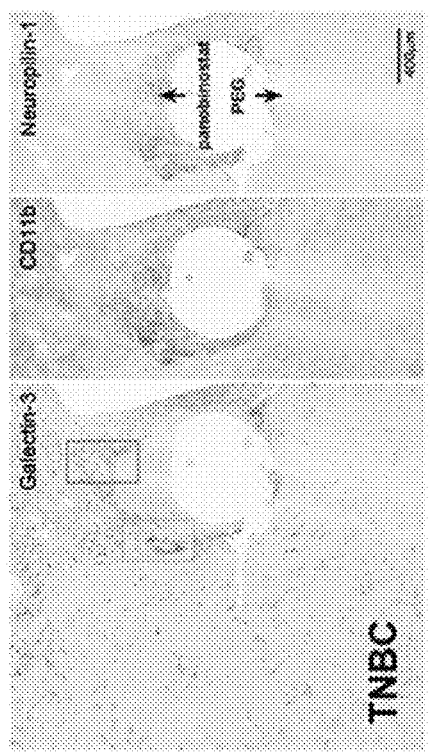
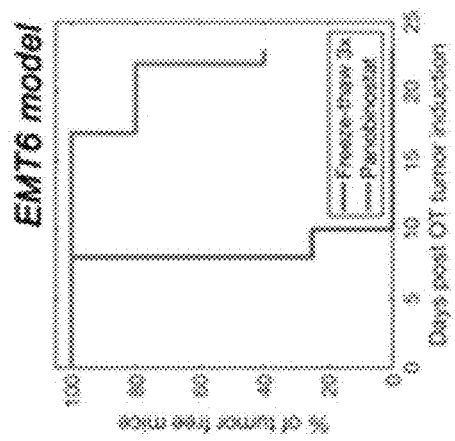
FIG. 19A  FIG. 19B  FIG. 19C

FIG. 20

| Microdevice 1 | | Microdevice 2 (same mouse, 2nd tumor) | |
|---|---|---|---|
| PEG | | | anti-Ly6G |
| Panobinostat 90% | | | anti-NRP1 |
| Panobinostat 90% | rmIFNβ | PEG | |
| Panobinostat 90% | anti-IFNAR | Panobinostat 50% | |
| Panobinostat 90% | ICAM1 | Panobinostat 50% | SM16 |
| Panobinostat 90% | anti-Gal3 | Panobinostat 50% | Pirfenidone |
| Panobinostat 90% | anti-Ly6G | Panobinostat 50% | Acriflavine |
| Panobinostat 90% | anti-NRP1 | SM16 | Panobinostat 50% |
| rmIFNβ | Panobinostat 90% | Pirfenidone | Panobinostat 50% |
| anti-IFNAR | Panobinostat 90% | Acriflavine | Panobinostat 50% |
| ICAM-1 | Panobinostat 90% | | SM16 |
| anti-Gal3 | Panobinostat 90% | | pirfenidone |
| anti-Ly6G | Panobinostat 90% | | acriflavine |
| anti-NRP1 | Panobinostat 90% | Pano LOW 90% | |
| | rmIFNβ | Pano LOW 90% | rmIFNβ |
| | anti-IFNAR | Pano LOW 90% | ICAM-1 |
| | ICAM-1 | rmIFNβ | Pano LOW 90% |
| | anti-Gal3 | ICAM-1 | Pano LOW 90% |

■CC3 signal low,■CC3 signal high. PEG, polyethylene glycol in which all small molecule drugs are formulated and thus serves as negative control. Pano LOW is a 12.5% instead of 30% panobinostat in PEG. SM16 and pirfenidone, TGFβ inhibitors. Acriflavine, hypoxia inhibitor. Different background represents comparable data.

FIG. 21A
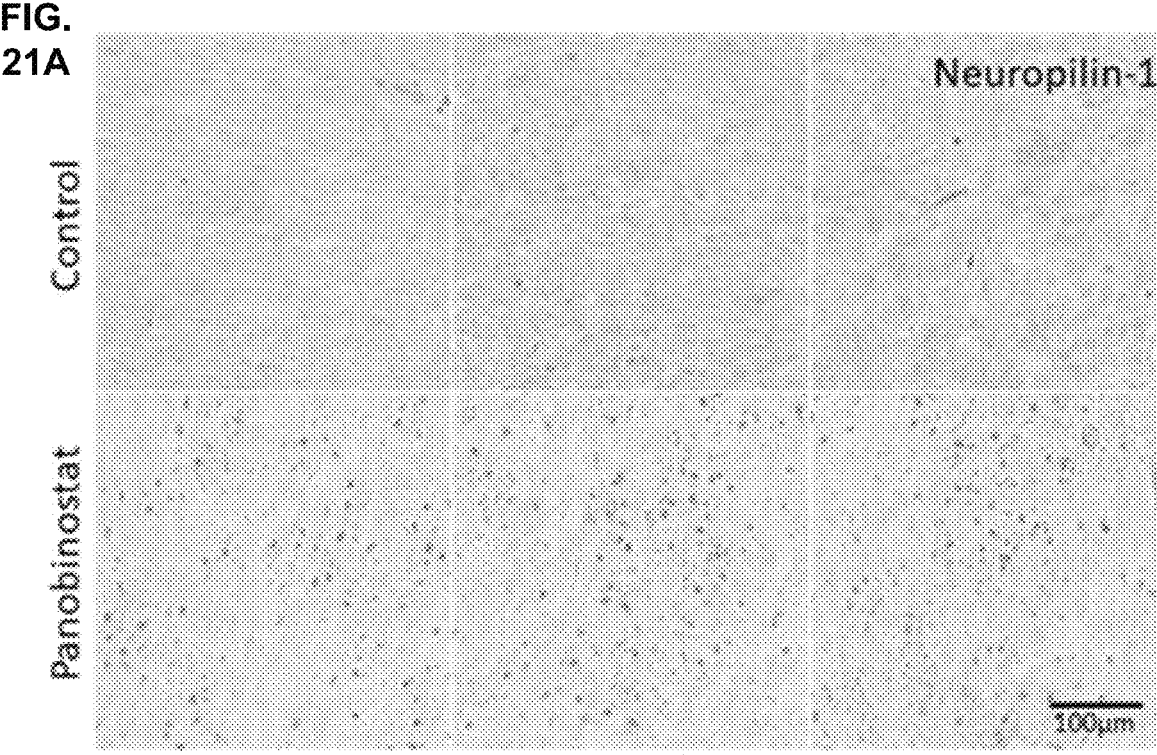
FIG. 21B Systemic drug-administration
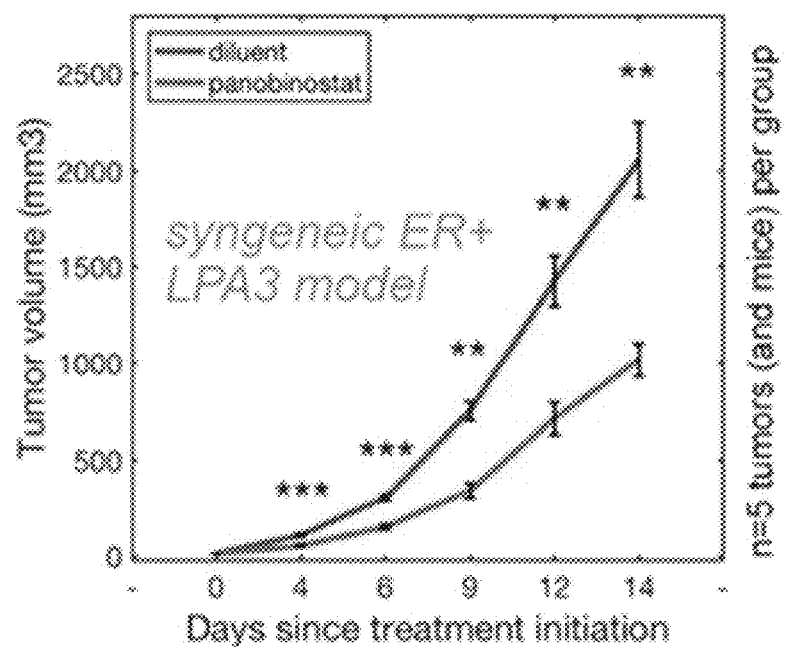

SYSTEMS, DEVICES, AND METHODS FOR EX VIVO ASSESSMENT OF RESPONSES TO MULTIPLE THERAPEUTIC AGENTS

CROSS-REFERENCE TO RELATED APPLICATION

This application claims priority to U.S. Provisional Application No. 62/664,907 filed on Apr. 30, 2018, which is incorporated herein by reference in its entirety as if fully set forth herein.

FIELD OF THE DISCLOSURE

The current disclosure provides devices, systems, and methods for local, ex vivo delivery of microdose amount(s) of active compound(s) into tissue, such as tumor tissue, that is maintained outside of a subject's body; and analysis of the response(s) of cells in the ex vivo tissue to the compounds. Also provided are expression profiles that provide insight into the responsiveness of ex vivo tissue to active compounds.

BACKGROUND OF THE DISCLOSURE

In the era of personalized medicine, therapies can be specifically tailored to patients based on tumor molecular characteristics. The critical issue is that only a subset of individuals exhibit clear and durable responses to the therapies employed. Achieving durable control will require a systemic approach that will i) prevent "rewiring" that enables therapeutic escape, ii) block resistance mechanisms that result from bidirectional interaction with the environment and iii) reactivate and enhance immune surveillance. Novel strategies will be needed to counter all of these mechanisms via administration of series of drug combinations that change as the tumors evolve under treatment pressure.

Given the importance of tumor microenvironment in immune modulation and the power of drug combination approaches, there is a high demand for personalized medicine tools that incorporate these features. There are two recent reports of the organotypic cultures derived from primary mouse and human samples, both using gastrointestinal tumors. Vlachogiannis et al. (*Science*, 359:920-926, 2018) has developed a "patient-derived organoid" model wherein heavily pretreated metastatic tumors are used to simulate cancer behavior ex vivo. Molecular profiling shows that this model system provides highly correlative data with respect to treatment response. The system is high-throughput but does not incorporate the immune compartment. Jenkins et al. (*Cancer Discov.*, 8(2):196-212, 2017) have developed an approach wherein tumors are first dissociated, then mixed with CD4, CD8 and myeloid (CD11b and/or CD11c) cells, and used to generate ex vivo organoid cultures to test candidate therapy. The authors claim the drug sensitivity testing has limited applicability for tumors lacking autologous immune/stromal cells based on comparisons of MC38 and CT26 derived spheroids. Additionally, the platform is not high-throughput, and the system is insufficient for performing screening of a functional therapy or combination.

Implantable devices for evaluation of active ingredients have recently been developed; see, for instance, U.S. Pat. No. 10,183,155 and Jonas et al. (*Sci. Transl. Med.* 7, 284ra57, 2015). However, the previously described systems are limited to in vivo use.

SUMMARY OF THE DISCLOSURE

Even though the immunotherapy field is revolutionizing the advanced cancer research, tools are still lacking that would maintain tissue-original complexity with intact immune system and on individual basis allow testing multiple drugs at once. The technology described herein addressing critical challenges that limit the development of such new precision medicine tool.

Disclosed herein is a novel pre-clinical model system for ex vivo culture of tumor biopsy core to incorporate high-throughput microdevices that allows for efficient, rapid, and safe assessment of tumor cell responses to a plurality of drugs and drug combinations. Also disclosed is a set of biomarkers that may be generated using the disclosed system that reflect the early response of tumor cells to drug treatment and provide an indicator of whether the treatment will be effective and durable. Such system is based on the recently developed implantable screening microdevice that permits localized intratumoral drug delivery and provides with the ability to predict the drug efficiency and select the right candidate within few days after application (Jonas et al., *Sci. Transl. Med.* 7, 284ra57, 2015).

One embodiment provides a method of assessing cell response to a plurality of anticancer agents, the method including: inserting into an ex vivo tissue sample an implantable drug-delivery device including at least 8 microwell reservoirs, and each reservoir holding one or more agents in solid form; incubating the ex vivo tissue sample with the inserted implantable drug-delivery device in a sustaining ex vivo environment for at least 12 hours and no more than 30 days; formalin fixing and paraffin embedding the ex vivo tissue sample with the drug-delivery device in place; analyzing composition or molecular status of tissue or cells adjacent each reservoir; and comparing the effects of each agent on adjacent tissue or cells. In specific examples of this embodiment, the cell is a tumor cell, the tissue sample is a tumor tissue sample, and at least one of the agents is an anti-cancer agent.

Another embodiment provides a method for determining efficacy of a compound in a tissue including: inserting into an ex vivo tissue sample outside of an organism an implantable microdevice including: a cylindrical support structure having microwells on a surface of or formed within the support structure, the microwells each containing and releasing after implantation a microdose of one or more active agents selected from therapeutic, prophylactic, and/or diagnostic agents; a microdose of one or more active agents in at least one microwell; and compound release mechanism including a polymeric matrix for controlling the release of the one or more active agents from the microwell; wherein the microdevice is configured to release the one or more active agents from the microwells to separate and discrete areas of tissue adjacent to each microwell without overlap between the discrete areas; incubating the ex vivo tissue sample with the inserted implantable microdevice in a sustaining ex vivo environment for at least 12 hours and no more than 10 days to produce agent-exposed tissue; and subjecting the agent-exposed tissue to multiplex immunohistochemistry (mIHC) analysis to determine the presence of Galectin-3 and Neuropilin-1, where presence or upregulation of either or both of Galectin-3 and Neuropilin-1 indicates the compound is effective.

Yet another embodiment is a method of determining efficacy of an anti-cancer agent to treat a solid tumor, including: administering the anti-cancer agent, to a subject having a solid tumor, for a period of at least 2 days;

subsequent to administering the anti-cancer agent: analyzing blood from the subject to determine presence and/or quantity of circulating galectin; and analyzing a tumor tissue sample from the solid tumor of the subject to determine the presence and/or quantity of neuropilin; wherein an increase in galectin and/or neuropilin compared to a control indicates that the anti-cancer agent is effective to treat the solid tumor.

Another embodiment is a method of assessing tumor cell response to a plurality of anticancer agents, the method including: obtaining a biopsy core of primary tumor tissue from a host; inserting into the biopsy core of primary tumor tissue an implantable drug-delivery microdevice including at least 8 microwell reservoirs, each reservoir holding one or more anticancer agents in solid form; maintaining the biopsy core of primary tumor tissue with the inserted microdevice in an extracellular matrix of stromal cells including endothelial cells, immune cells, and mesenchymal cells from the host, for at least 12 hours and no more than 30 days; formalin fixing and paraffin embedding the biopsy core of primary tumor tissue; analyzing the tumor tissue adjacent each reservoir using multiplex immunohistochemistry; and comparing the effects of each anticancer agent on adjacent tumor tissue.

BRIEF DESCRIPTION OF THE DRAWINGS

This application contains at least one drawing executed in color. Copies of this application with color drawing(s) will be provided by the Office upon request and payment of the necessary fee.

Many of the drawings submitted herein are better understood in color, which is not available in patent application publications at the time of filing. Applicants consider the color versions of the drawings as part of the original submission and reserve the right to present color images of the drawings in later proceedings.

FIGS. 1A-1F: Schematic representations of exemplary ex vivo tumor/tissue-microfluidic culture system as described herein. FIG. 1A shows a single tube/dome scaffold (for instance, made from polydimethylsiloxane (PDMS)), with a biopsy needle inserted from the top; a microdevice is situated within in the bore of the biopsy needle. FIG. 1B shows A tumor/tissue biopsy core extraction. FIG. 1C shows a single PDMS tube/dome scaffold submerged in a buffer solution to maintain pH and humidity to sustain survival of the extracted (ex vivo) tumor/tissue sample over an extended period of time. FIG. 1D is a cutaway view of a biopsy needle, revealing a modified implantable microdevice inside the biopsy needle without a tumor/tissue sample. The modified microdevice has a proximal handle to allow placement of the microdevice into a tumor biopsy core, or for deployment of a combined tumor biopsy and microdevice the into the single tube/dome scaffold along the central axis. The handle has an extended outer diameter immediately proximal to the microdevice that conforms to the inner surface of a biopsy needle to facilitate central alignment of the microdevice along the length of the biopsy needle. FIGS. 1E and 1F show a single PDMS tube/dome microfluidic scaffold having an inner chamber comprised of a biomimetic ECM material into which has been inserted a combined tumor biopsy (core) and microdevice. The single PDMS tube/dome scaffold is configured to allow microfluidic inflow into the system to perfuse the biomimetic ECM and combined tumor biopsy and microdevice FIG. 1D is a cutaway, showing the ex vivo implantable microdevice inside the biopsy needle without a tumor/tissue. FIGS. 1E and 1F show a PDMS tube/dome microfluidic scaffold into which has been inserted a tumor/tissue biopsy (core), into which has bene inserted a an implantable microdevice for delivery of active agent(s).

FIG. 2A is a single cylinder microfluidic scaffold housing a semi-solid ECM gel without a tumor/tissue core, which can be perfused through inlets. FIG. 2B is a microfluidic scaffold shown affixed to a slide surface; soft/necrotic tumors will not maintain cylindrical shape in a single-cylinder cylinder perfusion PDMS chamber.

FIG. 3A is an example device with two microfluidic PDMS layers that hold the tumor tissue intact (within the inner cylinder/dome) while also incorporating the ECM gel (in the outer compartment between the inner and outer PDMS cylinders). The dual cylinder design is configured to hold the tumor biopsy intact in the center compartment, and may be in communication through a plurality of pin-size holes or channels with the ECM/stromal component that occupies the outer compartment. As illustrated in FIG. 3C, the system can be completely submerged in medium, then perfused for long-term viability of the embedded tissue sample. In the embodiments illustrated here, the tumor core/tissue—microfluidic ex vivo culture does not incorporate stromal cells in the ECM gel, and is not "closed" on the top to form a dome format. FIG. 3D shows a schematic representation of a dual cylinder microfluidic culture system in cross sectional view.

FIG. 4A shows an illustrative perfusion system supply bottle, which can be pressurized for medium flow. FIG. 4B shows the top view of an exemplary "loaded" microfluidic scaffold, showing a supply pin directly touching spleen tissue inside the PDMS scaffold. Optionally, only the outer cylinder and the ECM matrix are in contact with the supply system. A drug delivery device is inserted in the center of the spleen tissue core. FIG. 4C shows spleen (left) and liver (right) tissue cored with the outer diameter of the scaffold (2 mm). The imprecise microdevice implantation is due to manual PDMS scaffold production in this illustration. FIG. 4D shows implant microdevices, including a close-up of drug-releasing reservoirs (left) as well as an insertable handle useful for sample manipulation. In the illustrated embodiment, the extended diameter above the assay area will direct the microdevice parallel to the biopsy needle well. FIG. 4E is schematic showing a microfluidic scaffold holder and automated supply system for user-friendly manipulation and long-term tissue maintenance in accordance with embodiments described herein. FIG. 4F is a graph illustrating results of a test of tissue maintenance in a representative double PDMS scaffold. Tumor tissues were inserted into the double PDMS scaffold and submerged. The system was supplied by flowing 10 ml of complete medium through three random inlets twice a day. Propidium iodide was infused to the scaffold at day 5, for dead-cell staining. Non-supplied ("no perfusion") tumor was not viable. Data suggest that the pulsed supply/perfusion as described in Tatárová et al. (*Lab Chip.* 16(10):1934-1945, 2016) increases the viability of the ex vivo intact tumor core to 90-100%.

FIGS. 5A-5C: FIG. 5A is an illustration of representative implantable microdevices (such as is described in U.S. Pat. No. 10,183,155). FIG. 5B provides technical drawings and dimensions for an embodiment of an implantable device useful in the ex vivo methods described herein. FIG. 5C is an illustration of an implantable microdevice showing the forward column 1 of the implantable device, along with multiple reservoirs 2 designed to accommodate anticancer or other therapeutic agents (for instance, in solid form). A conical or pointed distal end 3 assists in placement of the device in the intended tissue within the ex vivo containment device.

FIG. 6A: The illustrated implantable microdevice is a non-toxic 4×0.8 mm resin cylinder with eighteen 200 µm deep reservoirs, that are packed with drugs or drug combinations (active agents) in solid form. The device is implanted and stays in situ for up to 8 days; after which the tumor is harvested with the device in place and formalin fixed and paraffin embedded (FFPE). The tumor tissue is analyzed adjacent to each drug well using multiplex IHC (mIHC) with antibodies that interrogate cleaved caspase activity, epithelial, mesenchymal, endothelial status as well immune composition and activity. FIG. 6B: Design of the ex vivo platform using primary tumor biopsy. FIG. 6C: Image processing of the acquired phenotypes. Briefly, red staining is extracted by color deconvolution, image is transformed to 8 bit format and automatic threshold is applied. Two iterations of noise removal/dilation/closure and erosion are run using binary images. Fiji4 plugins and macro is used for automated image processing. Signal of individual markers are merged and the overlap is quantified on a single cell basis.

FIG. 7A-7D. Microenvironmental signals mediate resistance to targeted therapies in HER2+ breast cancers. Hepatocyte growth factor (HGF) and neuregulin-1b (NRG1b) mediate the resistance to tyrosine kinase inhibitors (TKIs), Neratinib and Lapatinib, in subtype-specific manner. While HGF is changing the TKI effectivity by decreasing apoptosis to normal levels in basal-like, JIMT1 (FIG. 7A), NRG1b restores the proliferation in luminal-like BT474 tumors (FIG. 7C) (Watson et al., *Cell Syst.* 1-14, 2018). The Initial discoveries were revealed using microenvironmental microarrays (MEMA, Gray and Korkola Lab). The implantable microdevice was used to validate these results in vivo which set the proof of concept and validated the correlative nature of the described implantable technique (FIGS. 7B, 7D).

FIGS. 8A-8J. Small scale screening and mIHC suggest synergy of panobinostat with anti-PD-1 therapy, and Galectin-3 and Neuropilin-1 to be the novel circulating and in situ predictive biomarkers of therapy response, respectively. (FIG. 8A) The MNA system identified panobinostat to induce apoptosis in the MMTV-PyMT mouse models of breast cancer after 3 days of in situ incubation. Mean intensity value of the CC3 signal was measured adjacent to the drug releasing reservoir and was normalized to control PEG only loaded reservoir. FIG. 8B) List of antibodies used in the MNA system and the basic probe categorization. FIG. 8C) mIHC was applied to panobinostat and doxorubicin reservoir. Most remarkable phenotypes of the basic panel are displayed. Blue is hematoxylin. We observed presence of a very small population of F4/80+MHCii+ macrophages in an immediate proximity to the panobinostat reservoir. Such macrophage population have strong positive prognostic value, especially when located in intratumoral nests vs. stroma (Kawai et al., *Cancer* 113(6):1387-1395, 2008). We expected that this population will be critical for effective panobinostat-mediated cell death and observed a significant decrease in CC3 signal next to panobinostat reservoir when mice were treated systemically by CSF-1R inhibitor for 10 days (FIG. 8A, last bar). Both molecules for antigen presentation, MHCii and MHCi, have increased presence in immunogenic vs. 'cold' tumors, inducing CTL infiltrate and predispose for checkpoint inhibitor response (Gibney et al., *Lancet Oncol.* 17(12):e542-e551, 2016). We observed a relative enhancement of MHCi on tumor cells right at the border of myeloid immune and tumor region (FIG. 8D).

Next, in the MNA panel, two biomarkers (Galectin-3 and Neuropilin-1) were included that have strong prognostic and/or predictive value in other cancers but their functional role in breast cancer is ambiguous or unknown, respectively. Using the second panobinostat replicate, it was found that neuropilin-1 is co-localized with the CD11 b pan-myeloid infiltrate while galectin-3 is present outside this area in a gradient manner (FIGS. 8E-8H). The galectin-3 marker is present preferably on tumor cells and exclusively on non-proliferating (non-GO) cells (FIG. 8E). Smeared Galectin-3 staining suggest that the protein is released into circulation in form of a free protein or bound to exosomes. The expected profile of Galectin-3 in circulation in breast cancer with respect to tumor progression (prognostic biomarker) and treatment response (predictive biomarker) is presented in FIG. 8F. (FIG. 8G) Neuropilin-1 cells are located on CD11 b positive pan-myeloid cells and more than 90% are myeloperoxidase positive neutrophils. This result suggest that Neuropilin-1 is a novel early (3 days) in situ predictive biomarker of positive treatment response as well as a novel biomarker of anti-tumor (N1) neutrophils. (FIG. 8H) Therapy response summarized showing overlayed images using pseudocolors at 3 days of panobinostat treatment in mouse models of triple negative and HER2+ breast cancer. (FIG. 8I) The systemic intraperitoneal drug-administration recapitulates the MNA identified treatment response as measured by tumor growth rate and Neuropilin-a IHC staining in situ (FIG. 8J). This validates the correlative nature of the MNA biotechnology as compared to whole animal studies.

FIGS. 10A-10B. (FIG. 10A) Multiplex nanodose assay system work flow: i) The implantable microdevice is a biocompatible 4×0.8 mm resin cylinder with eighteen reservoirs, that are packed with drugs or drug combinations in solid form. ii) Compounds are released into confined regions of tumors and are detected by fluorescence. After 1 to 8 days, iii) the tumor is harvested with the device in place, FFPE processed and stained by mIHC (iv) for apoptosis, proliferation, epithelial, mesenchymal, endothelial state and for immune complexity. iv) The drug-mediated effects are quantified using single cell-based image analysis and can be summarized in form of a heatmap (FIG. 10B).

FIGS. 11A-11B. Multiplex immunohistochemistry procedure. FIG. 11A) Schematic presentation of the mIHC staining procedure. FIG. 11B) Representative images of single stains and merged picture showing the same profile in pseudocolors. The section for staining was derived from an early tumor from the MMTV-PyMT model.

FIG. 12I a Table showing a list of drugs that directly upregulate major histocompatibility complex Class I (MHC-I) on ER+ MCF7 cells in transcriptomic studies.

FIG. 13A) Panobinostat mediates effective tumor killing and increases MHC-I expression on tumor cells in vivo at 3 days of exposure. Images show cross-section and CC3 staining adjacent to the drug-release site (top) and quantification of the MHC-I signal at the drug-well site vs. random tumor region (bottom). N=6 ROIs of 400× 400 µm size in 2 samples for each condition. Values are mean±SEM; ***$p<0.001$. FIG. 13B) The MNA-derived data showing prominent immune profiles and Galectin-3 and Neuropilin-1 to be positively correlated with panobinostat-mediated anti-tumor activity.

FIG. 14A-14B. FIG. 14A) Immunogenic potential of panobinostat in a vaccination study in the luminal A EMT6 mouse model. Tumor-free mice were identified by detecting tumors smaller than 4 mm in one dimension. N=4 for control and 5 for experimental group; respectively. FIG. 14B) Hematoxylin stained MMTV-PyMT tumor section at the intersection of drugs diffusing from the reservoirs as presented. Intersection of panobinostat/venetoclax is zoomed and shows prominent CD11c staining in bright field view and using pseudo-colors at the edge of the tumor cleared area.

FIGS. 16A-16C. Overview of the experimental design (FIG. 16A) and preliminary results (FIG. 16B) addressing the functional role of Galectin-3 and Neuropilin-1 in positive treatment response. (FIG. 16C) Extension of the mIHC staining and set of interventions further testing functional role of Galectin-3 and Neuropilin-1 in panobinostat mechanism of action.

FIG. 18A-18C. Multiplex nanodose assay identifies panobinostat to mediate tumor killing and infiltration of cytotoxic neutrophils. FIG. 18A) The implantable microdevice is a biocompatible 4×0.8 mm resin cylinder with eighteen reservoirs, that are packed with drugs or drug combinations in solid form. The device is implanted and stays in situ for up to 8 days; after which the tumor is harvested with the device in place, FFPE processed and stained by sequential IHC for apoptosis, proliferation, epithelial, mesenchymal, endothelial state as well as for immune complexity (FIG. 18B, 18C). FIG. 18B) Panobinostat significantly increased intratumoral apoptosis at three days of device incubation. Images show cross-section and CC3 staining for apoptosis adjacent to the drug-release site with replicates for panobinostat. The phenotype was associated with robust increase of neutrophils as shown by percentage of positive cells in the heatmap in (FIG. 18C). In all graphs, values are mean±SEM; *$p<0.05$, **$p<0.01$. The significance was determined by unpaired two tailed t-test.

FIG. 19A-19C. Panobinostat induces immunogenic apoptosis and Neuropilin-1 and Galectin-3 to play functional role in this process. FIG. 19A) Immunogenic potential of panobinostat in a vaccination study in the EMT6 mouse model (Rockwell, *Br J Cancer Suppl* 4:118-122, 1980). Tumor cells treated with panobinostat in vitro were injected into the right flank of immunocompetent BALB/c mice. The mice were re-challenged with live tumor cell injection into 4th mammary gland 10 days later. Mice vaccinated with panobinostat-death cells rejected the tumors after re-challenge. FIG. 19B) MMTV-PyMT (Guy et al., *Mol Cell Biol.* 12:954-61, 1992) tumor section with inserted device and stained for Galectin-3, CD11b pan-myeloid cells and Neuropilin-1. Cropped, pseudo-colored images and the stack bar graph display the spatial relation with other cell types. FIG. 19C) Graph showing CC3 signal decrease when panobinostat is combined with anti-Galectin3 antibody (M3/38) and anti-Ly6G (1A8) in the drug-releasing well.

FIG. 20 Is a table, illustrating experimental design to determine N1 neutrophil polarization importance for panobinostat mediated tumor killing.

FIG. 21. Systemic Panobinostat treatment enhances intratumoral Neuropilin-1 infiltrate and delays tumor growth

SUMMARY OF EMBODIMENTS OF THE DISCLOSURE

Figure 2A:
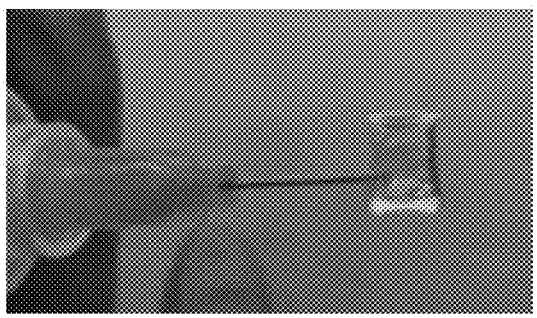
FIG. 2A-2B show representative microfluidic scaffolds.

There are provided herein devices, systems, and methods for determining the efficacy of a drug or drug combination to kill cancer cells.

In a specific example of a provided method, a cylindrical tumor or normal tissue biopsy core is extracted from a subject, for instance using a biopsy needle. A drug-eluting microimplant (an implantable micro-delivery device), loaded with one or more test agent(s) or mixtures or doses of test agents, is inserted into the ex vivo tumor biopsy core lengthwise (that is, the long axis of the implantable micro-delivery device is approximately parallel to the long axis of the tumor sample). The "loaded" tissue sample (that is, the tissue core with the embedded drug-eluting microimplant) is placed upright into a central compartment of a cylindrical microfluidics ex vivo system, for instance into a scaffold support structure, and provided with pulsatile perfusion for several hours or up to 28 days. In a specific embodiment, the loaded tissue sample is maintained in the sustaining microfluidic environment for 3 days. After the selected period of time (during which the test agents interact with adjacent cells and tissue in the tissue sample), the microimplant-loaded tissue sample (loaded tumor biopsy core) is removed from the microfluidics chamber and analyzed to determine one or more impacts of the agent(s) on the cells and/or tissue. In certain embodiments, the tissue sample is used to prepare histological sections to analyze, for instance, expression of one or more biomarkers in cells adjacent to microwells in the microimplant. In one particular embodiment, the presence of the biomarkers Galectin-3 (e.g., as illustrated in GenBank Accession No. O14786) and Neuropilin-1 (e.g., as illustrated in GenBank Accession No. P17931) is determined. As shown herein, the presence of these biomarkers is indicative of whether a particular drug or drug combination will be effective (i.e., kill cancer cells in a durable manner).

Galectin has a diffuse phenotype, and is therefore considered to be a circulating biomarker; whereas neuropilin is an in situ biomarker. By way of example, these biomarkers can be used to guide treatment decisions. For instance, a patient is treated with panobinostat, and on day 3 (though earlier and later at contemplated) galectin level is measured in the blood and neuropilin level is measured at the site of a tumor (for example, by taking a biopsy). If the patient is responding to treatment at day 3 (or whatever day is tested), as evidenced by increased expression of galectin and/or neuropilin, treatment continues.

In representative embodiments, the ex vivo culture platform combines:
  i) primary tumor/tissue cylindrical explant (OD 1-4 mm diameter, length up to 30 mm);
  ii) biomimetic environment (PDMS microfluidics, ECM-(like) matrix with or without stromal cells—submerged in a 37° C. buffered solution); and
  iii) an automated microfluidic supply system, which is linked to the ex vivo scaffold through metal tubes and tubing.

The biomimetic scaffold is, in some instances, made of a 0.5-2 mm thick PDMS dome that can be sealed to a slide surface (e.g. glass), for instance by high temperature (80° C.) bake overnight or by plasma treatment. The outer part of the scaffold will be filled with ECM-(like) matrix mixed or not mixed with stromal cells and these can be applied by injection into the outer PDMS space. Different matrices can be applied in the microenvironment, such as Matrigel, collagen, hydrogel, fibrin gels, and mixtures which mimic the ECM niche and generate physiologically relevant topography will be used. Stromal cell population mixed with the matrix may be be composed of endothelial, immune, and mesenchymal cells. Except from cell lines which will be preferred for human tumor/tissue explant; we will also incorporate primary circulating and bone marrow derived cells from the tumor/tissue host mouse when mouse tumor/tissues is used.

A representative procedure for ex vivo tumor/tissue biopsy core culture includes: assemble the PDMS scaffold; assemble the ECM-(like) matrix, with or without added stromal cells; after the matrix mixture solidifies, the biopsy needle together with the tumor piece inside is inserted vertically into this biomimetic scaffold. The implantable microdevice is then inserted into the tumor piece inside the biopsy needle (from the top opening). Optionally, the microdevice includes a handle that assists in stabilizing the tumor piece, for instance when the needle is being removed (e.g. with tweezers). This step leaves the tumor sample with the device directly exposed to the in vivo mimicking microenvironment. See FIG. 3D.

The platform, in this embodiment, is submerged in a standard culturing medium and put into a tissue culture incubator (5-10% $CO_2$, 37° C.). The PDMS elastomer is gas and vapor permeable and thus maintains pH and humidity. Additionally, such microfluidic/PDMS manifold generates a miniaturized environment that by default concentrates the soluble and ECM factors produced by the tumor/tissue explant and/or by the injected stromal cells (Tatárová et al., *Lab Chip.* 16(10):1934-1945, 2016).

Optionally, for instance where the tissue sample does not produce sufficient biological factors for cell viability, soluble factors may be introduced or diffused to the microenvironment through pin-size (e.g., diameter 0.5-3 mm) inlets/outlets in the PDMS double layer scaffold.

Embodiments of the scaffold are designed so that they can be attached to an automated or manual active microfluidic supply system that will increase the nutrient delivery and viability of the cells (Tatárová et al., *Lab Chip.* 16(10):1934-1945, 2016). Timing of the supply pulsing will be optimized depending on the tumor/tissue explant size so that it balances the nutrient delivery and washout of the cell produced stromal factors. The pulses of nutrient medium flow and nutrient medium diffusion into the system (flow stopped) will range between 5 s-2 hours for the flow step and 5 s-24 h for the diffusion (supply flow stopped).

After performing the functional drug sensitivity screen (0-28 days), the tissue surrounding the micro-delivery device is analyzed, for instance using standard formalin fixed paraffin embedded histology or OCT or tissue clearing.

One embodiment provides a method of assessing cell response to a plurality of anticancer agents, the method including: inserting into an ex vivo tissue sample an implantable drug-delivery device including at least 8 microwell reservoirs, and each reservoir holding one or more agents in solid form; incubating the ex vivo tissue sample with the inserted implantable drug-delivery device in a sustaining ex vivo environment for at least 12 hours and no more than 30 days; formalin fixing and paraffin embedding the ex vivo tissue sample with the drug-delivery device in place; analyzing composition or molecular status of tissue or cells adjacent each reservoir; and comparing the effects of each agent on adjacent tissue or cells. In specific examples of this embodiment, the cell is a tumor cell, the tissue sample is a tumor tissue sample, and at least one of the agents is an anti-cancer agent.

Agents useful in the provided methods include anti-cancer agents, carcinogens, growth factors, siRNAs, small molecules, cytokines, chemokines, antibodies, and radio-labeled compounds, as well as more generally any bio-active or suspected to be bio-active diffusible compound or mixture.

In more examples of these methods, analyzing the composition or the molecular status of tissue or cells adjacent each reservoir includes one or more of immunohistochemistry (IHC), immuno-detection, in situ RNA hybridization, sequencing, protein isolation, nucleic acid isolation, microscopic observation, or staining. More generally, any technique can be used to analyze the health, status, viability, and biological condition of cells and tissues in these methods.

In examples of the provided method embodiments, at least one microwell reservoir contains two different agents. In examples of the provided method embodiments, each microwell reservoir contains a different agent, a different mixture of agents, and/or a different dosage of agents.

Another embodiment provides a method for determining efficacy of a compound in a tissue including: inserting into an ex vivo tissue sample outside of an organism an implantable microdevice including: a cylindrical support structure having microwells on a surface of or formed within the support structure, the microwells each containing and releasing after implantation a microdose of one or more active agents selected from therapeutic, prophylactic, and/or diagnostic agents; a microdose of one or more active agents in at least one microwell; and compound release mechanism including a polymeric matrix for controlling the release of the one or more active agents from the microwell; wherein the microdevice is configured to release the one or more active agents from the microwells to separate and discrete areas of tissue adjacent to each microwell without overlap between the discrete areas; incubating the ex vivo tissue sample with the inserted implantable microdevice in a sustaining ex vivo environment for at least 12 hours and no more than 10 days to produce agent-exposed tissue; and subjecting the agent-exposed tissue to multiplex immunohistochemistry (mIHC) analysis to determine the presence of Galectin-3 and Neuropilin-1, where presence or upregulation of either or both of Galectin-3 and Neuropilin-1 indicates the compound is effective.

In examples of this method embodiment, the tissue sample is a tumor tissue sample, and at least one of the agents is an anti-cancer agent.

In additional examples, at least one agent is an anti-cancer agent, a carcinogen, a growth factor, an siRNA, a small molecule, a cytokine, a chemokine, an antibody, or a radio-labeled compound. More generally, any bio-active or suspected to be bio-active diffusible compound or mixture can be loaded into a microwell. In some embodiments, at least one microwell reservoir contains two different agents. In additional embodiments, each microwell reservoir contains a different agent, a different mixture of agents, and/or a different dosage of agents.

In other embodiments of the methods for determining efficacy of a compound in a tissue, analyzing the composition or the molecular status of tissue or cells adjacent each reservoir includes one or more of immunohistochemistry (IHC), immuno-detection, in situ RNA hybridization, sequencing, protein isolation, nucleic acid isolation, microscopic observation, or staining.

Yet another embodiment is a method of determining efficacy of an anti-cancer agent to treat a solid tumor, including: administering the anti-cancer agent, to a subject having a solid tumor, for a period of at least 2 days; subsequent to administering the anti-cancer agent: analyzing blood from the subject to determine presence and/or quantity of circulating galectin; and analyzing a tumor tissue sample from the solid tumor of the subject to determine the presence and/or quantity of neuropilin; wherein an increase in galectin and/or neuropilin compared to a control indicates that the anti-cancer agent is effective to treat the solid tumor.

Another embodiment is a method of assessing tumor cell response to a plurality of anticancer agents, the method including: obtaining a biopsy core of primary tumor tissue from a host; inserting into the biopsy core of primary tumor tissue an implantable drug-delivery microdevice including at least 8 microwell reservoirs, each reservoir holding one or more anticancer agents in solid form; maintaining the biopsy core of primary tumor tissue with the inserted microdevice in an extracellular matrix of stromal cells including endothelial cells, immune cells, and mesenchymal cells from the host, for at least 12 hours and no more than 30 days; formalin fixing and paraffin embedding the biopsy core of primary tumor tissue; analyzing the tumor tissue adjacent each reservoir using multiplex immunohistochemistry; and comparing the effects of each anticancer agent on adjacent tumor tissue.

In any of the described embodiments, the solid tumor may be a breast cancer tumor.

Figure 3A:
FIGS. 3A-3D illustrate the structure and use of a dual cylinder (two-layered) microfluidic culture system.
Figure 3B:
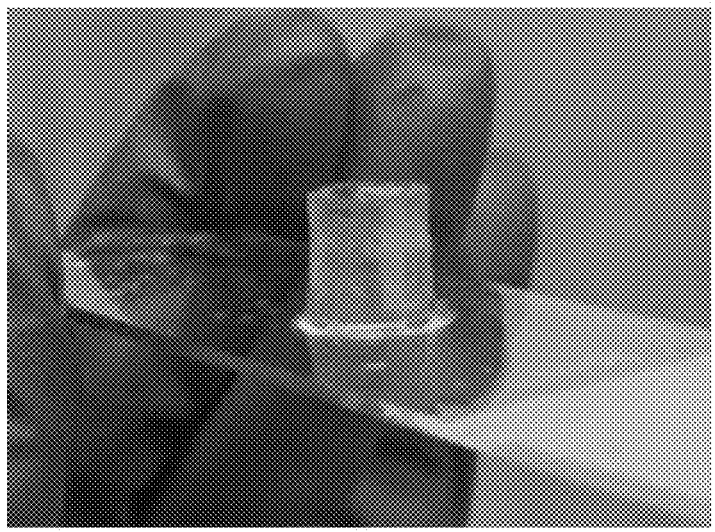
Figure 3C:
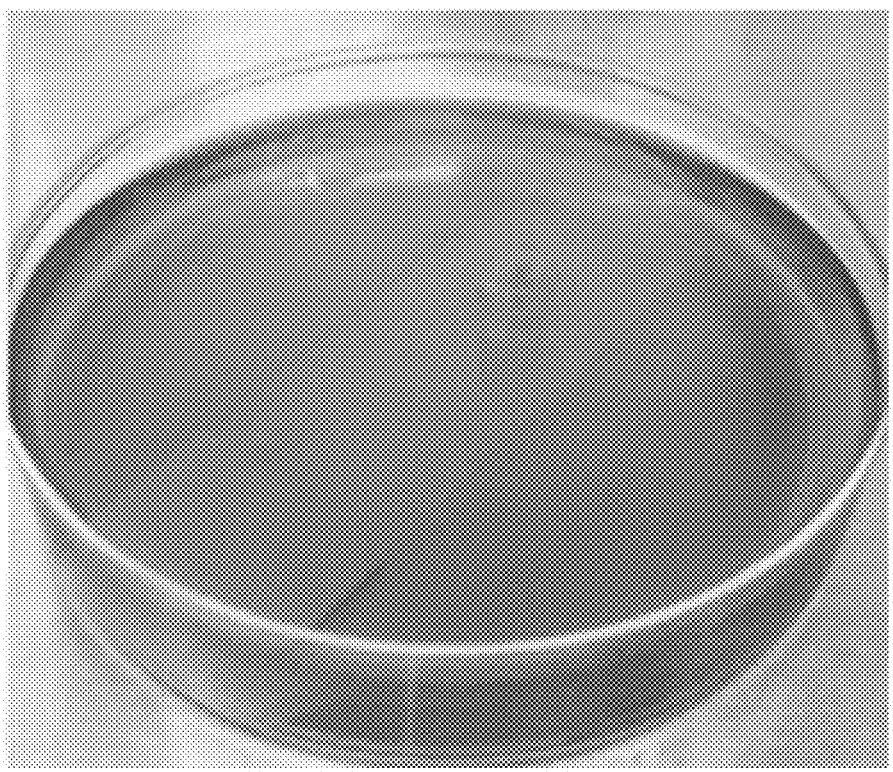
Figure 3D:
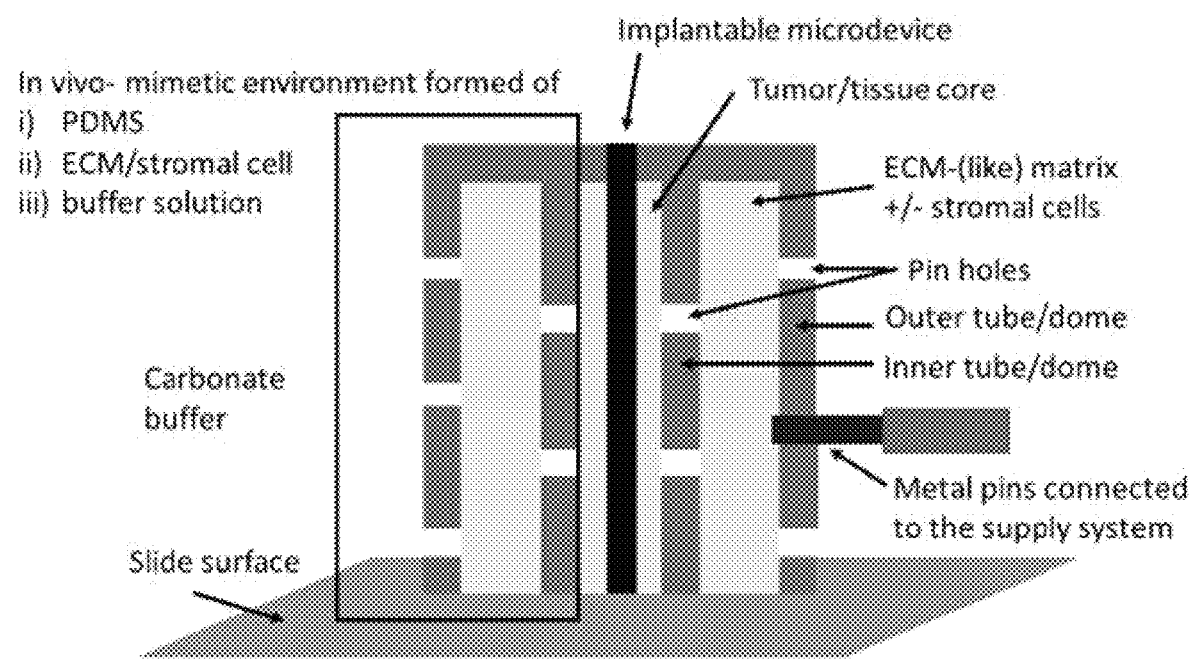

In any of the described embodiments, the sustaining ex vivo environment includes the device described in FIG. 3D.

DETAILED DISCLOSURE

A strength of the Jonas et al. (*Sci. Transl. Med.* 7, 284ra57, 2015) microdelivery device approach is that all measurements of biological impact are performed within a live tissue in the native tumor microenvironment, and with an intact immune system. The ex vivo methods and systems described in this disclosure combine a modified Jonas microneedle delivery device technology with microfluidic tissue maintenance and multiplexed immunohistochemistry (such as is described in Tsujikawa, et al., *Cell Rep.* 19, 203-221, 2017) to enable insights to mechanisms of response and resistance and propose rational combination treatment in breast cancers (BC) as well as other solid tumors. Correlation studies can be employed with the ex vivo implantable methodology to provide a novel pre-clinical model system to guide treatment selection.

Provided herein is a high-throughput ex vivo platform for drug-sensitivity screening using intact primary tumor biopsy tissue (e.g., a substantially cylindrical core sample), an implantable microdevice (e.g., a cylindrical drug-eluting system that can be placed into/along the longitudinal axis of the cylindrical tumor biopsy), and a microfluidic device or system that sustains cells in the tissue sample over a period of hours to days.

Embodiments described herein provide a 'vertical' frame of a microfluidic design that is adapted to accommodate a biopsy core (such as a tumor or other disease or normal tissue biopsy core), as compared to previously known 'flat' microfluidics that might be employed for tumor/tissue/organ slices. Embodiments of the provided "vertical" microfluidic device involve concentric PDMS cylindrical tube(s), with pin holes (for example, 0.01 mm-10 mm in diameter) that allow movement of fluids; an outer tube that can be perfused by external pump using automated pneumatic regulators or manually (by hand); an inner compartment bounded by the inner surface of the inner tube configured to receive a biopsy sample (such as a substantially cylindrical biopsy core; which biopsy sample, in turn, may receive an implantable microdevice); and space between outer wall of inner tube and inner wall of outer tube which, during operation in certain embodiments, defines an outer compartment which is filled with a simulated/biomimetic ECM populated with or without stromal cells.

The system can be functionalized using a microfluidic pulse perfusion to maintain high viability of fresh primary cultures ex vivo, such as that described in Tatárová et al. (*Lab Chip*. 16(10):1934-1945, 2016).

Implantable screening microdevices (such as those described in Jonas et al., *Sci. Transl. Med.* 7, 284ra57, 2015; and U.S. Pat. No. 10,183,155) may be adapted to the ex vivo culture system and methods, and can be incorporated for use with intact ex vivo tumor/microfluidic culture for multiple drug-testing.

Selection of the right therapy for individual cancer patients, such as breast cancer patients, must take into consideration not only the drug effects on the tumor cells, but also drug effects on the tumor microenvironment (TME). TME has equal importance to tumor intrinsic properties for cancer progression and drug response. A current challenge in testing drug effects on the tumor and TME response is to maintain the spatial organization of the tissue by preserving the original tissue intact rather than disassociating them, while performing high-throughput drug-sensitivity screening at the same time. In the system disclosed herein, screening is performed 'outside of the patient' to produce a safe alternative in situ model of tumor response in the body.

The Ex Vivo Platform

FIGS. 1-4) is intended to balance simplicity for general availability, efficiency for high-throughput and rapid result acquisition, and recapitulation of the tumor microenvironment for accurate measurements as compared to in vivo data.

One embodiment of the provided ex vivo culture system includes: primary tumor biopsy (1-6 mm in diameter, up to 50 mm long); a biomimetic environment (extracellular matrices +/−stromal cells), and simple microfluidics (two PDMS tubes 0.1-10 mm thick aligned one outside the other and communicating through pin-size holes (0.1-10 mm in diameter). The pin-size holes will be regularly or randomly placed in the inner and outer PDMS tubes and there will be 1-50 of them in each layer.

Figure 2B:
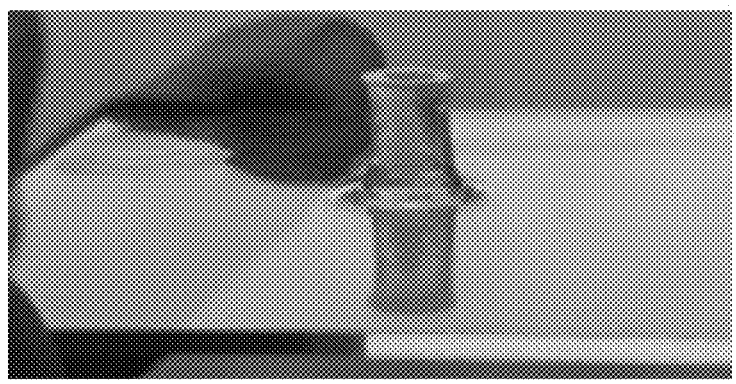

Another embodiment of the provided ex vivo tumor/tissue—microfluidic culture system is shown in FIGS. 1A-1F and FIGS. 2A-2B. This embodiment includes a single cylindrical polydimethylsioxane (PDMS) tube/dome housing a biomimetic ECM environment. This biomimetic ECM environment may optionally incorporate stromal cells into its composition. A primary tumor biopsy or tissue sample (1-4 mm in diameter, up to 25 mm long is deposited into the biomimetic ECM environment along the central axis of the ex vivo tumor/tissue—microfluidic culture system. The tumor/tissue biopsy may further be implanted with a drug screening microdevice positioned along the sample's central axis (FIGS. 1D, 1E, and 1F). The cylindrical PDMS tube is configured with a plurality of channels or pin-size holes (depicted in FIG. 1A) which serve as a microfluidics system by which the biomimetic ECM and tissue core biopsy may be perfused (FIG. 1F and FIG. 2A). In embodiments, it is also advantageous to use a pulsatile perfusion regimen to maintain cell viability within the biopsy core sample. In embodiments it is also advantageous to attach the cylindrical PDMS tube to a rigid base, such as a glass slide (FIG. 2B). This attachment may be effected, for example, by sealing the distal or open end of the tube/dome to the rigid base surface by plasma oxidation or by a high temperature bake (for example, 80° C. applied overnight). The entire ex vivo tumor/tissue—microfluidic culture system may further be submerged in a buffer solution to maintain pH and humidity to sustain survival of the extracted (ex vivo) tumor/tissue sample over an extended period of time (FIG. 10).

In one embodiment, the PDMS scaffold is comprised of concentric cylinder, up to 30 mm tall, forming two separate compartments, herein referred to as a dual cylinder system. An exemplary dual cylinder PDMA scaffold system is shown in FIG. 3A. In a dual cylinder system, an 'inner tube' of cylindrical shape having a specified mean diameter and wall thickness is generated. The inner surface of this inner tube defines the boundary of an 'inner compartment' that is intended to receive a biopsy tumor/tissue sample (the sample may optionally have an implantable microdevice deployed along its central axis). In embodiments, the inner tube mean diameter and wall thickness may range between 1-4 mm and 0.5-3 mm, respectively, depending on the diameter of tumor/tissue core sample. The inner (PDMA) tube provides support to maintain the tumor/tissue core intact when said tumor core is deposited into the inner compartment of the inner tube. The dual cylinder system also comprises an 'outer tube' having a larger mean diameter than the inner tube and positioned along a common centerline such that a concentric dual-tube assembly is defined. In embodiments, the outer tube mean diameter and wall thickness may range between 6-15 mm and 0.4-3 mm, respectively. The outer tube is sized so that there is space between the outer surface of the inner tube and the inner surface of the outer tube, said space defining an 'outer compartment.' Exemplary radial widths for this outer compartment may range between 0.5-5 mm. In embodiments this outer compartment may be filled with a biomimetic ECM material that may optionally be seeded with stromal cells (see FIG. 3B) for example, by injection of the ECM/stromal cell mixture into the space, to generate a biomimetic ECM environment. Different matrices may be employed for the biomimetic ECM environment, including Matrigel, collagen, hydrogel, fibrin gels, and mixtures which mimic the epidermal ECM niche and generate physiologically relevant topography. Stromal cell populations mixed with the biomimetic ECM matrix can include endothelial, immune, and mesenchymal cells. These cells can be derived from cell lines, or they can be primary circulating immune cells and/or total bone marrow harvested from a host.

Figure 4A:
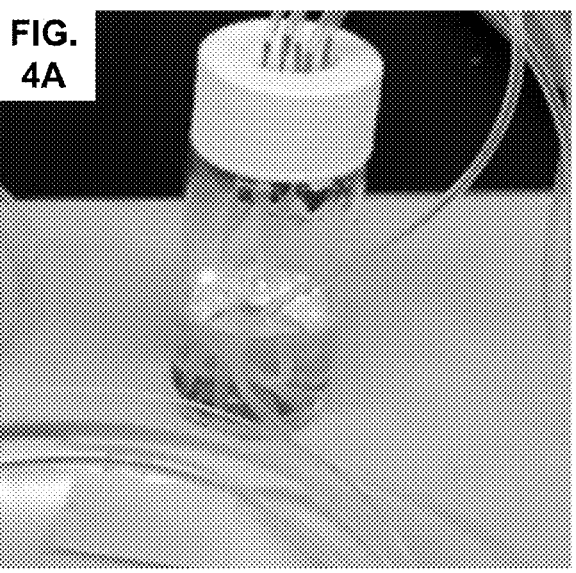
FIGS. 4A-4F show a tumor core/microfluidic scaffold combined with an active microfluidic supply system and with the implantable screening microdevice deployed into the biopsy core.
Figure 4B:
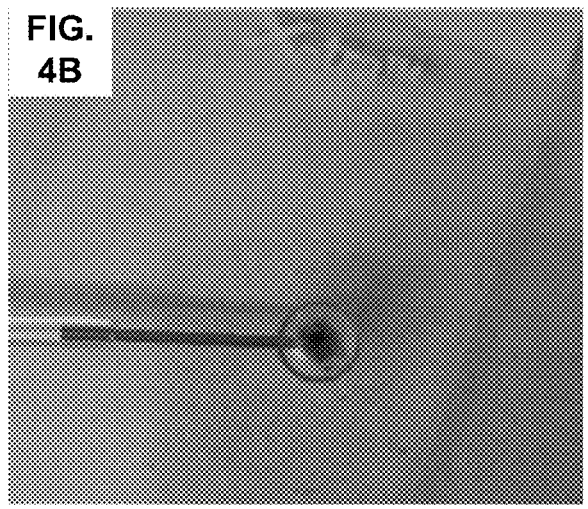
Figure 4C:
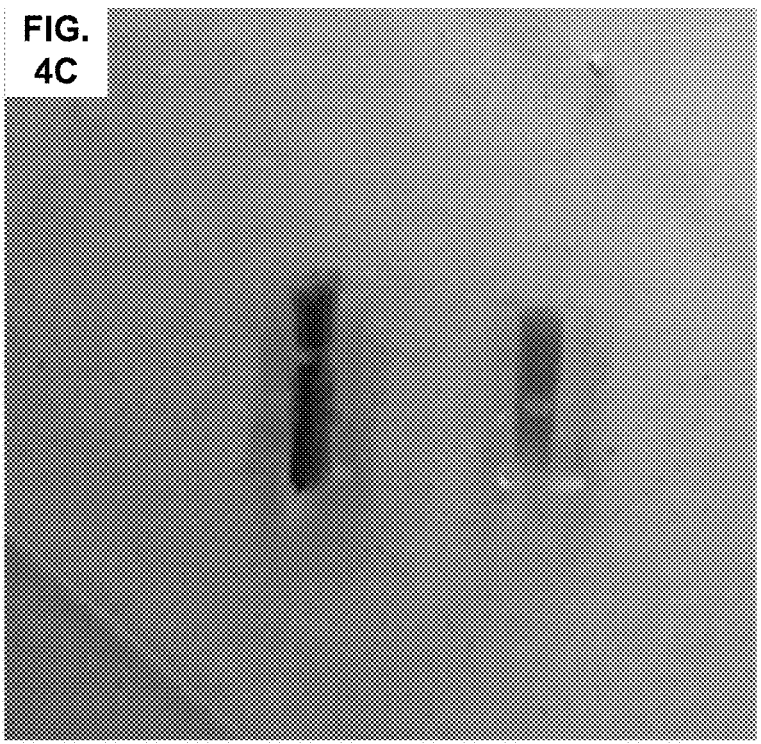
Figure 4D:
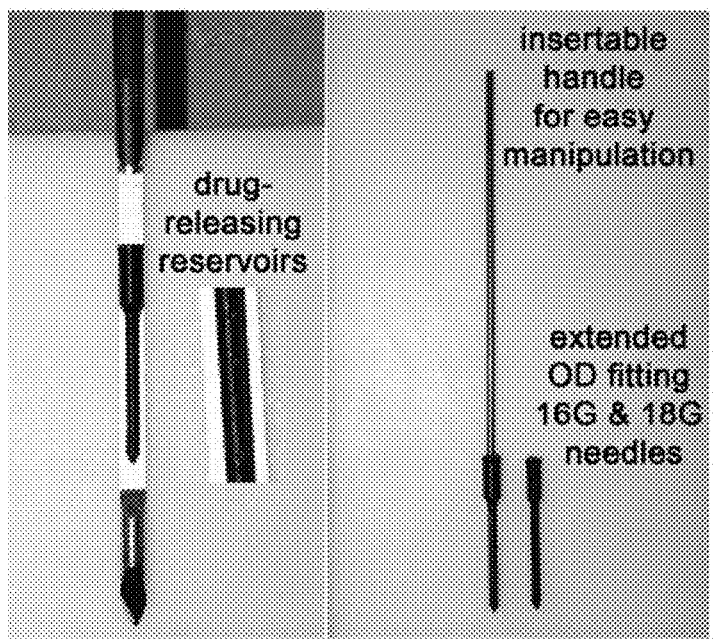
Figure 4E:
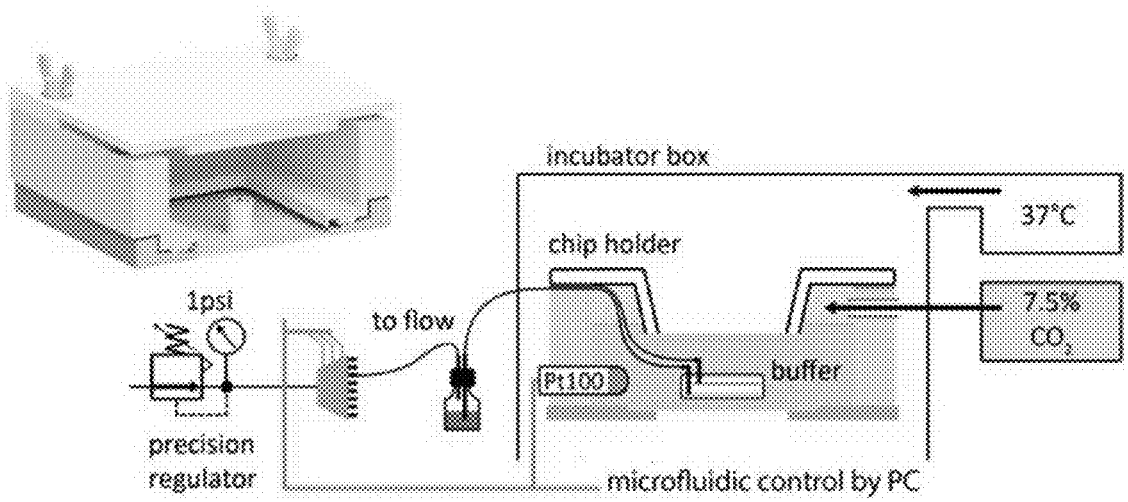
Figure 4F:
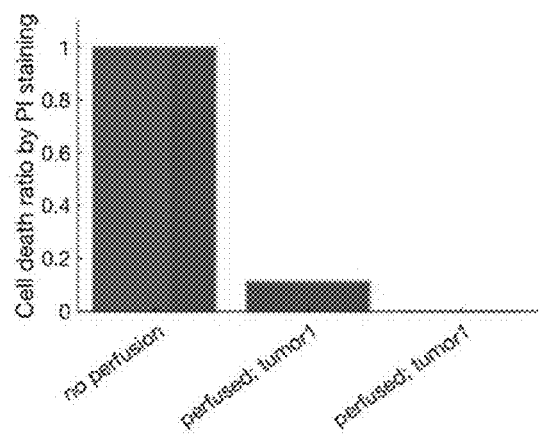

The dual cylinder system also comprises a microfluidics "manifold" aspect to enable perfusion of the ex vivo tumor/tissue—scaffold system and maintain cell and tissue viability. The inner tube is configured with a plurality pin holes that allow fluid communication between the inner compartment and outer compartment. Similarly, the outer tube is configured with a plurality of pin holes that serve as fluid inflow and fluid outflow sites to allow perfusion of the overall system. In embodiments, the number of pin holes for on each tube may vary between 2 and 40 holes having sizes in the range of 0.5-30 mm. A pulsatile perfusion regimen may be employed to maintain cell viability and communication between the ECM compartment and the tumor/tissue sample. The outer tube is connected via its plurality of pin holes to an active supply system (Tatárová et al., *Lab Chip*. 16(10):1934-1945, 2016) to maintain the viability of the tumor/ECM/stroma ex vivo microfluidic culture. In embodiments the whole system may be submerged in a buffered solution to maintain humidity and increase the ex vivo culture viability as shown in FIG. 3C (see Tatárová et al., *Lab Chip.* 16(10):1934-1945, 2016). For example, the ex vivo tumor/tissue—scaffold system may be submerged in a standard culturing medium and maintained in a tissue culture incubator (5-10% $CO_2$, 37° C.). FIG. 4E shows a schematic of an exemplary microfluidic scaffold holder system and automated supply system that allows for user-friendly manipulation and long-term tissue maintenance. This embodiment is functionalized through automated pressure-valves and generation of tissue-culture environment (adapted and modified from (Tatárová et al., 2016)). The microfluidic scaffold holder system may be configured to allow for i) submersion of the microfluidic device in a carbonate buffer, ii) infusion of $CO_2$, iii) measurement of temperature in close proximity to the scaffold and iv) fixation of the supply tubing to avoid loosening connections, thereby allowing unattended operation for several days (Tatárová et al., 2016).

FIG. 3D shows a schematic cross section of an exemplary dual cylinder device in accordance with the descriptions above. As shown, the device comprises an outer tube/dome component and an inner tube/dome component made of PDMS attached to a slide surface. These tube/dome components are each configured with a plurality "pin holes" that serve as inlets and outlets for fluid flow. As such, these components comprise a vapor-permeable microfluidics manifold system that can be perfused by an external pump supply system as well as submerges in a medium such as a carbonate buffer. The outer compartment is filled with an ECM-like matrix that may be optionally seeded with stromal cells as described above. The inner compartment holds the tumor/tissue core with an implantable microdevice inserted centrally along its length. On the left side of the figure, it is noted that the (i) PDMS outer and inner tube/domes, (ii) the ECM/stromal cell compartment, and (iii) the buffer solution in which the system is submerged comprise an in vivo-mimetic environment.

As noted above, in the disclosed system, a tissue sample (such as a cylindrical tumor or tissue biopsy core) is intended to be inserted vertically and centrally into the inner compartment of an inner PDMS tube. Furthermore, an implantable microdevice is to be inserted into said tissue sample, for instance, from a top opening, as depicted in FIG. 1E. In some embodiments it is advantageous to modify the microdevice to integrate a handle at its proximal end to facilitate placement of the distally located implantable microdevice into the tumor biopsy (FIG. 4D). The integration of such a handle facilitates the manipulation of a microdevice-implanted tissue sample and facilitates its deployment into inner compartment of the scaffold system. In some embodiments, the handle may have a section with an increased diameter (relative to the rest of the handle and microimplant), said increased diameter being sized to conform to the inner bore diameter of a biopsy needle. This region of increased diameter to serves to ensure axial alignment of the microdevice when it is translated within the bore of the biopsy needle. Once the tumor sample is deployed into the inner compartment of the biomimetic scaffold it is exposed to the in vivo mimicking microenvironment as described above (that is, a microfluidic scaffold incorporating the ECM+/−stromal cells, submerged in buffered solution, and connected to active perfusion supply system).)

Alternatively, the "straight" insertion in the tumor core can be mediating through magnetic forces by placing a magnet into the tip of the implantable device. The magnetic forces can be activated applying electromagnetic environment at the time of insertion that will pull the device perpendicular to the slide surface. After the implantable device is in place, the biopsy needle is removed (if primarily inserted with the tumor/tissue core).

An aspect of the PDMS elastomer comprising the scaffold described herein is that it is gas and vapor permeable and thus able to maintain a consistent pH and humidity environment. Additionally, such microfluidic/PDMS manifold generates a miniaturized environment that by default concentrates the soluble and ECM factors produced by the injected stromal cells (Tatárová et al., *Lab Chip.* 16(10): 1934-1945, 2016). Soluble factors are allowed to diffuse to the inner microenvironment through inlets (holes, such as pinholes) in the wall of the inner tube. Additionally, pumps and automated pulsed supply may be employed to increase the perfusion of the system and viability of the cells as noted above (Tatárová et al., *Lab Chip.* 16(10):1934-1945, 2016).

Timing of the supply pulsing can be optimized so that the supply and washout of the cell produced factors are balanced. After performing the functional drug sensitivity screen, the tumor tissue will be processed as for standard formalin-fixed paraffin-embedded (FFPE) (for instance, similarly as descried in Jonas et al., *Sci. Transl. Med.* 7, 284ra57, 2015). OCT or tissue clearing will be used as alternative for other visualization techniques. Reporter systems incorporated for e.g. CC3 signal can provide live detection of drug sensitivity without the need for visualization.

As described herein, the provided microenvironment platform keeps the original tumor tissue intact and viable. Thus, the tissue in contact with the active agent(s) in the microdelivery device reacts to those agent(s) in a substantially "native" manner, even though the tissue is maintained ex vivo.

I. Implantable Micro-Delivery Devices

Certain methods and systems described herein employ an implantable (into tissue) microdevice to deliver one or more active agents to adjacent tissue. Useful implantable microdelivery devices can be found, for instance, in U.S. Pat. No. 10,183,155, issued Jan. 22, 2019. "Active Agent," as used herein, refers to a physiologically or pharmacologically active agent that can act locally and/or systemically in the body. The term "active agent" includes agents that can be administered to a subject for the treatment (e.g., therapeutic agent), prevention (e.g., prophylactic agent), or diagnosis (e.g., diagnostic agent) of a disease or disorder. Also included in the term are agents or compounds that are being tested for the efficacy as a treatment, prevention, or diagnosis agent including diffusible chemicals, such as carcinogens, proteins such as growth factors, cytokines or chemokines or an siRNA.

A. Support Structure. "Support Structure," as used herein, refers to the body of the device to which one or more microwells are attached or within which one or more microwells are formed. Devices generally include one or more microwells formed on or within a support structure. The support structure forms the body of the device. The support structure can be fabricated to form devices having a variety of shapes. For example, the device can be cuboid, cubic, or cylindrical in shape. Optionally, the device is cylindrical or substantially cylindrical. The support structure may also be configured to have one or more areas of separation. For example, depending on such factors as the material used and number of microwells, the areas of separation may include perforations, a material of enhanced flexibility or lower durometer, hinges, joints, etc., which allow portions of the support structure to be separated or to flex.

The device is generally sized to be implanted using a needle or the like. In certain embodiments, the dimensions of the device are suitable for implantation using an 18 gauge biopsy needle, stylet, cannula or catheter. For instance, example cylindrical implantable devices have a diameter of between 0.5 mm and 2 mm, for instance between 0.5 mm and 1.5 mm, or between 0.5 mm and 1.0 mm. In a particular embodiment, the cylindrical device has a diameter of approximately 0.9 mm. In certain embodiments, the cylindrical device has a length of less than 5 mm, more preferably less than 4 mm, most preferably less than 3 mm. In a particular embodiment, the implantable device has a length of 2.5 mm.

B. Microwells. "Microwell," as used herein, refers to a chamber, void, or depression formed within or on the support structure. In a preferred embodiment, it is a discrete chamber not commonly accessible via other microwells or a channel, port, or reservoir accessing more than one microwell. The surface of the device includes a plurality of microwells, each of which typically includes a solid bottom proximal to the support structure, one or more solid side walls, and an opening located on the surface of the device distal to the support structure. Alternatively, the microwells can be in the form of a hemispherical bowl. The microwells must be discrete and fillable so that agent to be delivered can be loaded prior to implantation, but be releasable after implantation. The microwells may be fillable from a central lumen, or common delivery channel within the device (so long as the common channel can be sealed to prevent cross-contamination between microwells), which can be directed into one or more microwells, or filled from the outside of the device and then sealed. In the certain embodiments, each microwell is isolated from other microwells to prevent any contamination of agent in one microwell with that in another. Microwells are be separated by sufficient support structure or microwell wall thickness that agent released from one microwell does not overlap with agent released from adjacent microwell(s).

Devices can contain any number of microwells. Optionally, wells are provided in five rows of eight wells. Representative numbers of microwells range from four to 100. The microwells may have any dimensions (e.g., length/width, diameter, and/or depth) suitable for a particular application, and which can be supported on the intended microdelivery device. In some embodiments, all of the microwells in a device have the same shape and dimensions. In such cases, all of the microwells in the device may also have substantially the same volume. In other embodiments, the array contains microwells with multiple shapes, dimensions, or combinations thereof. In such cases, microwells with one or more different volumes are likely to be incorporated into a single device.

The microwells can have any suitable shape. For example, the microwells can be circular, ovoid, quadrilateral, rectangular, square, triangular, pentagonal, hexagonal, heptagonal, or octagonal. In some embodiments, the microwells are rectangular in shape. In these instances, the shape of the microwells can be defined in terms of the length of the four side walls forming the perimeter of the rectangular microwell.

In certain instances, the rectangular microwells have side walls ranging from 50 microns to 500 microns in length, for instance from 100 microns to 400 microns in length. In particular embodiments, the four side walls forming the perimeter of the rectangular microwell are of substantially equivalent length (i.e., the microwell has a square shape). Example sizes are 100×100, 200×200, and 400×400 microns, with depths of 100 to 300 microns.

In some embodiments, the microwells are spherical in shape. In certain instances, the spherical microwells have diameters ranging from 50 microns to 500 microns, for instance from 100 microns to 400 microns.

The depth of the microwells, governed by the height of the solid side walls forming the microwells, can vary to provide microwells having the desired volume and/or volume-to-surface-area ratio for particular applications. In certain instances, the depth of the microwells ranges from 50 microns to 500 microns, for instance from 75 microns to 400 microns, or from 100 to 300 microns.

The microwells may have any volume suitable for a particular application. In certain instances, the volume of the microwells ranges from $1.25 \times 10^5$ cubic microns to $1.25 \times 10^8$ cubic microns, for instance from $1.00 \times 10^5$ cubic microns to $6.40 \times 10^7$ cubic microns, or for instance from $1.00 \times 10^5$ cubic microns to $4.80 \times 10^7$ cubic microns.

The microwells may be arranged on or within the support structure in a variety of geometries depending upon the overall device shape. In particular embodiments, the microwells are arranged so as to virtually eliminate overlap in the tissue of active agents released from different microwells. For example, in some embodiments, the microwells are arranged on or within the support structure with the axes of the microwells relatively parallel and the distal openings in a relatively single plane. In this configuration the microwells can be arranged in rectangular or circular arrays. Alternatively, the microwells may be arranged in a three-dimensional pattern where the distal ends of the microwells lie in multiple planes. In this three-dimensional pattern the axes of the microwells may be relatively parallel or be skewed relative to one another, depending on the overall shape of the device.

The microwells may be equally spaced from one another or irregularly spaced. In preferred embodiments, the edges of neighboring microwells are separated by at least 50 microns, for instance at least 75 microns, or for instance at least 100 microns. In certain embodiments, the edges of neighboring microwells are separated by at least 100 microns, 200 microns, 300 microns, or 400 microns.

Cylindrical devices are contemplated with a diameter ranging from 500-1100 microns, and a height of 2-4 mm. Microwells are contemplated to be added by micromachining, for instances microwell diameters ranged from 130-600 microns and microwell depth ranged from 50-600 microns.

Microwells may also have edges, walls, or be recessed within the device to help prevent overlap between agent released into the tissues from the microwells. Means for sealing the microwells may also be designed so that release only occurs through one area, such as the center, of the microwell, to further limit overlap with agent released from adjacent microwells into the tissue.

In general, microwells provide local delivery of individual compounds/mixtures/dosages. "Local Delivery" and "Local Administration," as generally used herein, refer to the administration of an active agent to a target tissue location from a source that is at the target tissue location, or adjacent to or in close proximity to the target tissue location.

C. Materials Used to Form Devices. Devices may be fabricated from any biocompatible material or combination of materials that do not interfere with delivery of one or more active agents, assays performed, or data collection, if employed. "Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

Optionally, the device may be radiopaque to facilitate imaging. In some cases, one or more portions of the device are fabricated from a material, such as stainless steel, which is radiopaque. In some cases, one or more contrast agents are incorporated into the device to improve radiopacity or imaging of the device.

Appropriate materials include biocompatible polymers, generally nonbiodegradable, since the device is intended to be embedded into and remain within an ex vivo tissue sample.

Biodegradable polymeric materials may be used to fabricate the device. "Biodegradable Polymer" and "Bioerodible Polymer" are used herein interchangeably, and generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment. Suitable degradation times are from hours to weeks, more preferable from days to weeks.

The microwells and support structure are generally fabricated from biocompatible materials that provide the device with suitable integrity to permit device implantation into an ex vivo tissue sample, and to provide the desired residence time within the target tissue. In instances where the microwells, support structure, or both are fabricated from a non-biocompatible material, the non-biocompatible material may be coated with another material to render the microwells and support structure biocompatible.

In some embodiments, the microwells and support structure are formed from a single material. In other embodiments, the microwells and support structure are formed from multiple materials that are combined so as to form an integral structure. Examples of materials that can be used to form the microwells and/or support structure include polymers, silicones, glasses, metals, ceramics, inorganic materials, and combinations thereof. In certain embodiments, the microwells and support structure are formed from composite materials, such as, for example, a composite of a polymer and a semiconductor material, such as silicon. Devices have been manufactured out of the following materials, Acrylic resin, polycarbonate, Acetal resin (DELRIN™), polytetrafluoroethylene (TEFLON™, polyether-ether-ketone (PEEK), polysuflone and polyphenol sulfone (RADEL™)

In some embodiments, the microwells, support structure, or combination thereof, are formed from or include a polymer. Examples of suitable polymers include polyacrylates, polymethacrylates, polycarbonates, polystyrenes, polyethylenes, polypropylenes, polyvinylchlorides, polytetrafluoroethylenes, fluorinated polymers, silicones such as polydimethylsiloxane (PDMS), polyvinylidene chloride, bis-benzocyclobutene (BCB), polyimides, fluorinated derivatives of polyimides, polyurethanes, poly(ethylene vinyl acetate), poly(alkylene oxides) such as poly(ethylene glycol) (PEG), or copolymers or blend thereof.

In certain embodiments, microwells, support structure, or a combination thereof, are fabricated from or include one or more biodegradable polymers. Examples of suitable biodegradable polymers include polyhydroxyacids, such as poly (lactic acid), poly(glycolic acid), and poly(lactic acid-co-glycolic acids); polyhydroxyalkanoates such as poly3-hydroxybutyrate or poly4-hydroxybutyrate; poly (caprolactones); poly(orthoesters); poly(phosphazenes); polyesteramides; polyanhydrides; poly(dioxanones); poly (alkylene alkylates); poly(hydroxyacid)/poly(alkylene oxide) copolymers; poly(caprolactone)/poly(alkylene oxide) copolymers; biodegradable polyurethanes; poly(amino acids); polyetheresters; polyacetals; polycyanoacrylates; poly(oxyethylene)/poly(oxypropylene) copolymers, or a blend or copolymer thereof, may be used. Biodegradable shape memory polymers, such as those described in U.S. Pat. No. 5,189,110 or 5,139,832, may also be employed.

In some embodiments, the microwells, support structure, or combination thereof, formed from or include a metal. Examples of suitable metals include, but are not limited to, cobalt, chromium, nickel, platinum, gold, silver, silicon, stainless steel, titanium, tantalum, and any of their alloys (e.g., nickel-titanium alloys), and combinations thereof. Biodegradable metals such as magnesium-based metals may also be used.

In particular embodiments, the microwells, support structure, or combination thereof are fabricated from or include silicon or a ceramic such as hydroxyapatite, alumina, zirconia, bioglass, piezo ceramics, or nanocermics. In particular embodiments, the microwells, support structure, or combination thereof are fabricated from or include a polymer formed from SU-8, the structure of which is known to those of skill in the art (see, e.g., U.S. Pat. No. 10,183,155).

The device may include an agent that prevents or reduces biofilm formation or inflammation or other foreign body reaction to the device once implanted. Such an agent may be incorporated within one or more of the component materials of the device, or coated on a surface the device, or portions thereof. In certain embodiments, one or more portions of the device is coated with a polymer coating to prevent or reduce biofilm formation or inflammation or other foreign body reaction to the device.

Figure 5B:
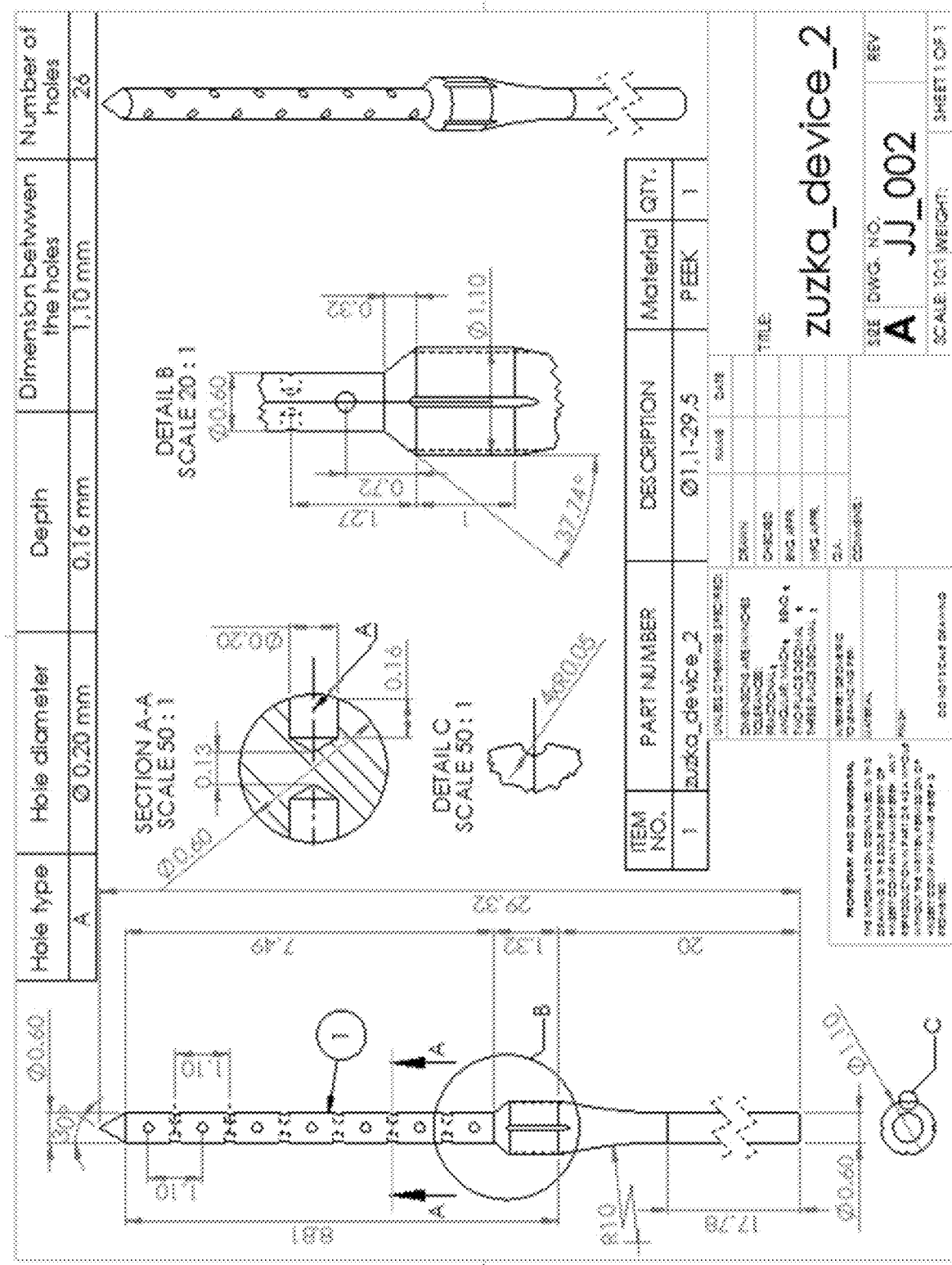

Representative examples of cylindrical micro-implantable delivery devices are illustrated in FIGS. 5A and 5B. The device contains a support structure, forming the body of the device. The device has a proximal end, and a plurality of microwells formed within the support structure. One or more of the microwells contain an active agent or agents, which can be released independently or in combination.

D. Active Agent Release Mechanisms: While it is contemplated that compound release from microwells in the delivery device may be passive (that is, occur substantially by passive transport such as diffusion), it is acknowledged that drug compounds have inherently different transport rates, which depend on their chemical properties. To obtain optimal diffusion of the active agent into the surrounding tissue, one option is to control the release of the active agent from the microwells. For instance, release of the active agent may be controlled so as to virtually eliminate overlap in the tissue of active agents released from different microwells. The release systems may be natural or synthetic. In some variations, the release system may be selected based on the period over which release is desired, the rate of diffusion desired, or the amount of diffusion desired. Active agents held in microwells can be released not only with distinct active agents and concentrations, but also at different kinetics, depending on (for instance) a different material coating in each well (such as platinum or gold or polymer).

i. Microwell Opening: Altering the size of the microwell opening can influence the rate of drug release. A large opening results in a faster release of the active agent into the surrounding tissue than a small opening. This may be advantageous for drugs that diffuse slowly through the tissue. A smaller opening may be advantageous for drugs that diffuse rapidly through the tissue.

ii. Membranes and Films: A membrane or film may be applied to the well after the active agent is incorporated, for instance to isolate the active agent until the time of use. The film may be manually removed immediately prior to use or may be degraded upon implantation (depending on its constituents) to allow release of the active agent into the surrounding tissue. Alternatively, a porous membrane may be used to cover the microwells to control rate of release after implantation.

iii. Matrices: The active agent may be contained (inside of the microwell) within a matrix formed of a biodegradable material or a material which releases the incorporated substance by diffusion out of or degradation of the matrix, or by dissolution of the substance into surrounding interstitial fluid. Preferably, the matrix includes poly (ethylene glycol) (PEG). When provided in a matrix, the substance may be homogeneously or heterogeneously distributed within the matrix. Selection of the matrix may be dependent on the desired rate of release of the substance. Both biodegradable and nonbiodegradable matrices can be used for delivery of the substances. Suitable release matrices include, without limitation, polymers and polymeric matrices, non-polymeric matrices, or inorganic and organic excipients and diluents such as, but not limited to, calcium carbonate and sugar.

iv. Hydrogels: "Hydrogel," as used herein, refers to materials which swell extensively in water and dissolve or erode with time depending on the viscosity and the molecular weight of the material. A hydrogel pad can be placed within each microwell. Compounds may then be placed on top of hydrogel pads located within the microwells. In such embodiments, when the device is implanted, small amounts of fluid from the surrounding tissue diffuse into the microwells and cause the hydrogel pads to expand. During expansion, the compounds are forced into the surrounding tissue. Hydrogel release mechanisms can achieve significantly larger intra-tissue active agent concentrations in short time frames and therefore allows for more a rapid active agent efficacy analysis.

Active agent delivery can be fine-tuned by using hydrogels with different hydrophilic expansive properties. By way of example, the hydrogel is poly-acrylamide based. Other exemplary hydrogel-forming polymer materials include cellulose ethers, different viscosity/molecular weight grades of hypromelloses such as hydroxypropyl methyl cellulose (HPMC K4M to K100M available from Dow Chemical); cross-linked acrylates such as CARBOPOL™; alginates; guar or xanthan gum; carrageenan; carboxymethylcellulose; and mixtures thereof. The hydrogel-forming polymeric material is present in an amount from about 2% to about 80% by weight, preferably 3% to 50% by weight of the matrix.

II. Active Agents

One or more active agents are incorporated in one or more of the microwells in the devices. In some devices, the microwells contain one or more active agents, in one or more dosages, alone or in one or more combinations. In other devices, not all of the microwells contain an active agent. In these embodiments, empty microwells may serve as a control, or to increase distance between released active agents thereby decreasing or eliminating overlap of two or more diffused agents.

In some embodiments, each microwell which contains an active agent contains a different active agent or different combination of active agents. In some embodiments, the microwells each contains an active agent or combination of active agents in differing amounts of active agents, differing ratios of active agents (for instance, different amounts of two or more agents being tested together, for instance for combined effects), or different excipients/formulations of active agents. This allows variation not only of the drug, but also the dosage, release pharmacokinetics, and testing of various combinations at the same.

A. Compounds: In various embodiments, the active agent is an anti-neoplastic agent. "Anti-neoplastic agent", as used herein, refers to an active agent that either inhibits the growth and multiplication of neoplastic cells, such as by interfering with the cell's ability to replicate DNA, and/or is cytotoxic to neoplastic cells. Representative anti-neoplastic agents include alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and *vinca* alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as camptothecin, irinotecan, and topotecan as well as derivatives of epipodophyllotoxins such as amsacrine, etoposide, etoposide phosphate, and teniposide). Anti-angiogenic compounds may also be tested, such as thalidomide.

Other active agents may be anti-infectives such as antivirals, antibiotics, or antifungals; or immunomodulators, such as immunoenhancers, vaccines, or immunosuppressants (including anti-inflammatories); or hormones or their analogues, or hormone agonists or antagonists.

Active agents may be small molecule active agents or larger molecules (e.g., macromolecules) such as proteins, peptides, carbohydrates and nucleic acids. "Small Molecule", as used herein, refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

Compounds (agents) other than anti-neoplastic (or anti-cancer) agents are also contemplated. These include carcinogens, mutagens, nucleic acids (such as siRNAs), growth factors, and any other biologically active molecules, compounds, or compositions.

B. Microdose: "Microdose," as used herein, refers to an amount of an active agent that is locally administered to a tissue to determine one or more clinical parameters, such as efficacy of active agent, the metabolism of the active agent, or a combination thereof. The devices deliver a microdose amount of a substance to a target tissue, ex vivo but in a native-like tissue environment. A microdose amount may be from about 0.001 µg (or less) to about 1,000 µg, or about 10,000 µg (or more) of the substance. In certain embodiments, the amount of the microdose is optimized so as to virtually eliminate overlap in the tissue of active agents released from different microwells. Those of skill will readily appreciate that microdose levels may vary as a function of the specific substance employed, the target tissue, and/or the medical condition being treated.

The compound may be delivered in a controlled release, sustained release, delayed release, bolus followed by sustained release, and/or pulsatile release. Delivery may also occur over any time period. For example, it may occur over a period of minutes to hours, or days to weeks. In certain embodiments, release is complete within 48 hours, with substantially all drug being released within 12, 24, 36, or 48 hours. Optionally, the release profile and delivery time is optimized so as to virtually eliminate overlap in the tissue of active agents released from different microwells.

The agent may be applied as a powder, particulate, or in a solution or suspension, with the solvent removed by drying, evaporation, lyophilization or suction.

III. Methods of Manufacture

Devices can be fabricated using methods known in the art, such as patterning, photolithography, etching and CNC micromachining. Suitable methods for the manufacture of devices can be selected in view of a variety of factors, including the design of the device (e.g., the size of the device, the relative arrangement of device features, etc.) and the component materials used to form the device.

Examples of suitable techniques that can be used, alone or in combination, for the fabrication of devices include LIGA (Lithographic Galvanoforming Abforming) techniques using X-ray lithography, high-aspect-ratio photolithography using a photoresist, such as an epoxy-based negative photoresist such as EPON™ SU-8 (also referred to as EPIKOTE™ 157), microelectro-discharge machining (µEDM), high-aspect-ratio machining by deep reactive ion etching (DRIE), hot embossing, 3-dimensional printing, stereolithography, laser machining, ion beam machining, and mechanical micro-cutting using micro-tools made of hard materials such as diamond.

Detailed methods for microfabrication are described in, for example, "Microreactors, Epoch-making Technology for Synthesis" (edited by Jun-ichi Yoshida and published by CMC Publishing Co., Ltd., 2003) and "Fine Processing Technology, Application Volume—Application to Photonics, Electronics and Mechatronics—" (edited by the Meeting Committee of the Society of Polymer Science, Japan, and published by NTS Inc., 2003.

As demonstrated in U.S. Pat. No. 10,183,155, implantable micro-delivery devices have been loaded with distinct compounds in up to 30 microwells. The compounds have been loaded as crystalline powder, lyophilized powder, compressed microtablets, as liquids dissolved in water or buffer solution, as solid dissolved in poly(ethylene-glycol) of molecular weight 200, 400, 600, 800, 1000, 1450, 3400 and 7500.

IV. Methods of Use

The device and corresponding assays deliver confined, locally-delivered, precise quantities of drugs into a solid tissue sample (e.g., a biopsy, such as a tumor biopsy) outside of a living organism and allow rapid and minimally invasive diagnostic assessment of interactions between drugs and tissues in ex vivo tissue maintained in a sustaining, in vivo-like environment.

The device is implanted directly into an excised (ex vivo) tumor or other tissue sample to be tested/treated/analyzed. In embodiments involving cancer, the tissue will typically be transformed, i.e. cancerous tissue, but in other embodiments the tissue may be infected with bacteria, fungus or virus, in need of immunomodulation (i.e., immunosuppression or immunoenhancement), or in need of hormonal adjustment or some other treatment. Normal tissue is also contemplated. In some cases, a hormone may be useful for treating a cancer. The device is particularly useful in testing combination of drugs that may be more effective in combination.

In some embodiments, the microdosing device is inserted into the tumor or other (healthy or diseased) tissue while that tissue is in the subject, then a biopsy or other tissue sample is removed from the subject with the microdosing device intact in the extracted sample. The resultant ex vivo sample, already containing a microdosing device, is then maintained ex vivo (for instance in a microfluidic device as described herein) to allow the micro-dosed agents time to act on adjacent tissue. Subsequent analysis can be carried out as described herein.

The device releases an array of drug microdoses locally, and uses state of the art detection methods to identify the drugs or combinations inducing a response. By using microdoses of drugs, the device is capable of testing individual patients, or individual tissues, for response to large range of agent regimens, ex vivo and without inducing systemic toxicities. These data can be used, for instance along with genomic data, to accurately predict systemic drug response.

In some variations, a microdose amount is used in early human studies, e.g., before a phase I clinical trial, to evaluate the effect of the substance on a target tissue, or to obtain pharmacokinetic or metabolic data.

The assay may be used to detect one or more of: a degree of agent permeation through the target tissue; a physiochemical effect of the agent on the target tissue; a pharmacological effect of the agent on the tissue; and/or interactions between two or more co-administered agents, including the reaction(s) of cells in the target tissue to such interactions. The assay may be configured to provide various data such as data related to efficacy such as chemotherapeutic efficacy; activity such as tumor cell invasiveness; toxicity such as toxicity due to one or more agents being delivered or toxicity due to cell death; endothelial branching, activation or inhibition of immune cells; and combinations of these.

A. Target Tissues: "Tissue," as used herein, refers to groups of cells that perform a particular function, as well as organs, which are aggregates of tissues. Given that the target tissue, or a sample thereof (such as a biopsy) is removed and placed into a support scaffold for ex vivo testing, the target tissue can be any tissue from the subject that can be sampled. The target tissue may be located anywhere in a patient's body, such as locations including: liver, lung, kidney, prostate, ovary, spleen, lymph node, thyroid, pancreas, heart, skeletal muscle, intestine, larynx, esophagus and stomach. In embodiments involving cancer analysis or treatment, the target tissue is tumor tissue such as adenoma, adenocarcinoma, squamous cell carcinoma, basal cell carcinoma, small cell carcinoma, large cell undifferentiated carcinoma, chondrosarcoma, fibrosarcoma, or a combination thereof.

The target tissue may also be a tissue which is infected, for example, with a virus, bacteria, fungus or parasite, or which is characterized by inflammation or is in need of immunostimulation.

"Tumor," as used herein, refers to an abnormal mass of tissue that results from the proliferation of cells. Typically, solid tumors do not contain cysts or liquid areas within the tissue mass. Solid tumors can arise in any part of the body, and may be benign (not cancerous) or malignant (cancerous). Most types of cancer other than leukemias can form solid tumors. Solid tumors include, for example, adenocarcinomas, carcinomas, hemangiomas, liposarcomas, lymphomas, melanomas and sarcomas.

B. Excision of the Target Tissue: The tissue sample is excised from the patient using any recognized procedure, including percutaneous, minimally invasive, or open procedures that provide access to the target tissue of a patient. For example, a tissue sample may be obtained via an open surgical procedure, or by a minimally invasive procedure such as laparoscopy, endoscopy, arthroscopy, and catheter-based procedures.

An image of the target tissue, such as a tumor, may be performed prior to harvest or during harvest, for instance to allow image guidance-enhanced selection of the tissue sample.

Upon removal from the subject, the tissue sample is inserted into a support microfluidic ex vivo scaffold as described herein, and introduced to a tissue-maintaining environment to permit maintenance of the tissue sample ex vivo for a period of hours to weeks.

C. Delivery of the Device: Devices may be implanted into the excised target tissue (e.g., a tumor or other tissue biopsy or tissue core) via injection directly into the tissue, usually for instance from a proximal end of the tissue sample along the long axis of the sample.

In most cases, the device is implanted into a tumor using a biopsy-type needle, cannula, catheter or stylet. The devices may be delivered using a needle, such as a 19 to 24 gauge biopsy needle—though it is contemplated that the delivery mechanism must be small enough to deliver the device into the excised tissue sample.

In some embodiments, the (loaded) micro-delivery device is placed using a cutting biopsy needle with sharp stuffer tip. The stuffer needle is then retracted while keeping the needle in place. The device is delivered through the needle into the excised, ex vivo tissues sample, then the need is retracted.

Unlike the in vivo system provided in U.S. Pat. No. 10,183,155 and Jonas et al. (*Sci. Transl. Med.* 7, 284ra57, 2015), there is no need to retrieve the device after a period of time. Instead, the device and the surrounding excised tissue sample (for instance, tumor biopsy) can be analyzed without concern about disrupting the spatial orientation of the tissue relative to the device. The simple maintenance of spatial orientation achieved through the provided ex vivo embodiments ensures ease of assessment of the efficacy, dose dependency, and type of response (i.e., apoptosis, necrosis, inflammation, subclinical response) of each agent or agent preparation included in the implanted microdevice.

D. Analysis of Tissue: Following introduction of the micro-delivery device and exposure of the ex vivo tissue sample to the agents/test compound(s), usually less than 7 days from microdevice insertion, more preferably within 24 to 48 hours following microdevice insertion, the treated tissue sample is analyzed, for example, by microscopic examination, by enzyme assays, and other histology and immunohistochemistry techniques, for instance to assess cancer or infected cells. By way of example, the tissue sample including the embedded micro-delivery device may be embedded in acrylic or another matrix, sectioned, and histological analysis or other analyses performed. Alternatively, the cylinder of tissue can be cut open and flattened into a slab of tissue. The flattened tissue slab can then be analyzed, for instance by immunohistochemistry and other techniques. Optionally, the slab of tissue may embedded in paraffin, acrylamide or other fixation compounds in preparation for preservation or analytical techniques.

V. Biomarkers and Related Analyses

Provided herein is the discovery that Galectin-3 (e.g., as illustrated in GenBank Accession No. 014786) and Neuropilin-1 (e.g., as illustrated in GenBank Accession No. P17931) are useful as biomarkers which indicate the efficacy of an anti-cancer treatment, or more generally which indicate that a compound may trigger cell death or immune cell recruitment. As described herein, the presence (or relatively increased abundance, for instance compared to a control such as an untreated tissue) of these biomarkers is indicative of whether a particular drug or drug combination will be effective (for instance, for killing cancer cells in a durable manner).

Galectin is shown herein to have a diffuse phenotype, and is therefore considered to be a circulating biomarker. In contract, neuropilin is an in situ biomarker. Thus, galectin can be detected circulating in a blood sample from a subject, whereas neuropilin is beneficially detected in situ in a tissue sample, such as through immunohistochemistry and the like.

By way of example, these biomarkers can be used to evaluate, grade, and qualify compounds tested using the ex vivo system used herein. However, their usefulness is not linked or limited to use with the herein provided ex vivo, micro-dosing implantable devices. These biomarkers provide robust indicators of the efficacy of compounds to kill cells, for instance tumor cells in solid tumors, even when such compounds are applied in non-micro doses, and/or are applied in vivo or in situ. In addition, these biomarkers can be used to guide treatment decisions. For instance, a patient is treated with panobinostat, and on day 3 (though earlier and later at contemplated) galectin level is measured in the blood and neuropilin level is measured at the site of a tumor (for example, by taking a biopsy). If the patient is responding to treatment at day 3 (or whatever day is tested), as evidenced by increased expression of galectin and/or neuropilin, treatment continues.

Though exemplified through detection of the galectin-3 and neuropilin-1 proteins using immunohistochemistry, it will be recognized by those of ordinary skill that these proteins can be detected in a number of ways. In addition, the level of protein expression can be correlated with the level of mRNA expression, and thus detection of mRNAs encoding galectin or neuropilin also can be sued as biomarkers in methods described herein.

VI. Kits

Kits may contain one or more of the devices described herein. Any number and type of deployment devices/tools, tumor sample maintenance devices/tools, and imaging devices may also be included. The kits may also contain additional in vitro assays for evaluating samples, such as a matrix for fixing tissue samples for histological analysis.

The kits may also include instructions for using the devices, tools, and/or assays contained therein.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments, Set 1

1. A method of assessing tumor cell response to from 15 to 40 anticancer agents, the method including: inserting into a tumor an implantable device including from 15 to 40 reservoirs, each reservoir being from 180 μm to 250 μm deep, and each reservoir holding one or more anticancer agents in solid form; maintaining the implantable device in situ in the tumor for from one to ten days; harvesting the tumor with the device in place; formalin fixing and paraffin embedding the tumor; analyzing the tumor tissue adjacent each reservoir using multiplex immunohistochemistry; and comparing the effects of each anticancer agent on adjacent tumor tissue.

2. The method of embodiment 1 wherein the multiplex immunohistochemistry is accomplished with antibodies that interrogate cleaved caspase activity.

3. The method of any of embodiments 1 and 2 wherein the multiplex immunohistochemistry is accomplished with antibodies that interrogate epithelial status.

4. The method of any of embodiments 1, 2, and 3 wherein the multiplex immunohistochemistry is accomplished with antibodies that interrogate mesenchymal status.

5. The method of any of embodiments 1, 2, 3, and 4 wherein the multiplex immunohistochemistry is accomplished with antibodies that interrogate endothelial status.

6. The method of any of embodiments 1, 2, 3, 4, and 5 wherein the multiplex immunohistochemistry is accomplished with antibodies that interrogate immune composition and activity.

7. The method of any of embodiments 1, 2, 3, 4, 5, and 6 wherein the implantable device including from 15 to 30 reservoirs.

8. A method of assessing tumor cell response to from 15 to 40 anticancer agents, the method including: collecting from a host a biopsy core of primary tumor tissue; maintaining the biopsy core of primary tumor tissue in an extracellular matrix of stromal cells including endothelial cells, immune cells, and mesenchymal cells from the host; inserting into the biopsy core of primary tumor tissue an implantable device including from 15 to 40 reservoirs of from 120 μm to 250 μm deep reservoirs, each reservoir holding one or more anticancer agents in solid form; maintaining the implantable device in biopsy core of primary tumor tissue for from one to ten days; formalin fixing and paraffin embedding the biopsy core of primary tumor tissue; analyzing the tumor tissue adjacent each reservoir using multiplex immunohistochemistry; and comparing the effects of each anticancer agent on adjacent tumor tissue.

9. The method of any of embodiments, 1, 2, 3, 4, 5, 6, 7, and 8, wherein the reservoirs have a diameter of from about 0.15 mm to about 0.25 mm.

10. The method of any of embodiments, 1, 2, 3, 4, 5, 6, 7, 8, and 9, wherein the reservoirs have a diameter of from about 0.17 mm to about 0.23 mm.

11. The method of any of embodiments, 1, 2, 3, 4, 5, 6, 7, 8, 9, and 10, wherein the reservoirs have a depth of from about 0.10 mm to about 0.22 mm.

12. The method of any of embodiments, 1, 2, 3, 4, 5, 6, 7, 8, 9, 10, and 11, wherein the reservoirs have a depth of from about 0.10 mm to about 0.22 mm.

13. An implantable device including: a columnar staff from 5 mm to 10 mm in length, said columnar staff having a conical distal end; and from 15 to 40 reservoirs of from 180 μm to 250 μm deep dispersed substantially equally around the surface of the columnar staff, and each reservoir holding one or more anticancer agents in solid form.

14. The method of any of embodiments 1-12 and the implantable device of embodiment 13 wherein at least one reservoir contains one or more anticancer agents selected from the group of abemaciclib, arbitrexate, anastrozole, capecitabine, carboplatin, cisplatin, cyclophosphamide, docetaxel, doxorubicin, epirubicin, eribulin, everolimus, exemestane, 5-fluorouracil, fulvestrant, gemcitabine, goserelin, ixabepilone, lapatinib, letrozole, megestrol, methotrexate, neratinib, paclitaxel, albumin-bound paclitaxel, palbociclib, pamidronate, olaparib, lenvatinib, panobinostat, ribociclib, tamoxifen, toremifene, vinblastine, vinorelbine; or a pharmaceutically acceptable salt thereof.

15. The method of any of embodiments 1-12 and the implantable device of Embodiment 13 wherein at least one reservoir contains a combination of anticancer agents selected from the group of: doxorubicin hydrochloride and cyclophosphamide; doxorubicin hydrochloride, cyclophosphamide, and paclitaxel; doxorubicin hydrochloride, cyclophosphamide, and fluorouracil; cyclophosphamide, methotrexate, and fluorouracil; fluorouracil, epirubicin hydrochloride, and cyclophosphamide; and docetaxel, doxorubicin hydrochloride, and cyclophosphamide.

16. A method for determining efficacy of a compound in a tissue: including inserting into an ex vivo tissue sample outside of an organism an implantable microdevice including: a cylindrical support structure having microwells on a surface of or formed within the support structure, the microwells each containing and releasing after implantation a microdose of one or more active agents selected from therapeutic, prophylactic, and/or diagnostic agents; a microdose of one or more active agents in at least one microwell; and compound release mechanism including a polymeric matrix for controlling the release of the one or more active agents from the microwell; wherein the microdevice is configured to release the one or more active agents from the microwells to separate and discrete areas of tissue adjacent to each microwell without overlap between the discrete areas.

17. The method of embodiment 16, including a compound release mechanism including a film, a membrane, and/or a hydrogel pad.

18. The method of embodiment 16 or 17, wherein the microdevice includes two or more active agents, dosages of active agents, or combinations of active agent within the microwells.

19. The method of any one of embodiments 16-18, wherein the microdevice has microwells releasing active agent with different pharmacokinetic release profiles.

20. The method of any one of embodiments 16-19, wherein the microdevice is implanted using a catheter and a guide wire, wherein the guidewire is mechanically coupled to the support structure of the microdevice.

21. The method of any one of embodiments 16-20, wherein the microwells of the microdevice are separated by walls or include recessions which limit release of active agents into areas of release from adjacent microwells.

22. The method of any one of embodiments 16-21, wherein active agent is released from the microwells as a bolus, sustained release, delayed release, bolus followed by sustained release, and/or pulsatile release.

23. The method of any one of embodiments 16-22, wherein the active agent is present in solid form in the microwell or the device does not include needles or a fluid reservoir.

24. The method of any one of embodiments 16-23, wherein the microdevice is formed by a method including deep ion etching, nano imprint lithography, micromachining, laser etching, three dimensional printing, and/or stereolithoraphy.

25. The method of any one of embodiments 16-24, further including cutting the ex vivo tissue sample along an axis parallel to a length of the microdevice to form a slab of tissue to be analyzed.

26. The method of any one of embodiments 16-25, further including performing an assay on the tissue to characterize an impact of the active agents on the tissue sample.

27. The method of embodiment 26, wherein the assay is performed on one or more slices of the tissue sample, which slices are made substantially perpendicular to an axis parallel to a length of the microdevice.

28. The method of any one of embodiments 16-27, wherein the tissue is a tumor.

Exemplary Embodiments, Set 2

1. A method of assessing cell response to a plurality of anticancer agents, the method including:
   inserting into an ex vivo tissue sample an implantable drug-delivery device including at least 8 microwell reservoirs, and each reservoir holding one or more agents in solid form;
   incubating the ex vivo tissue sample with the inserted implantable drug-delivery device in a sustaining ex vivo environment for at least 12 hours and no more than 10 days;
   formalin fixing and paraffin embedding the ex vivo tissue sample with the drug-delivery device in place;
   analyzing composition or molecular status of tissue or cells adjacent each reservoir; and
   comparing the effects of each agent on adjacent tissue or cells.

2. The method of embodiment 1, wherein the cell is a tumor cell, the tissue sample is a tumor tissue sample, and at least one of the agents is an anti-cancer agent.

3. The method of embodiment 2, wherein at least one agent is an anti-cancer agent, a carcinogen, a growth factor, an siRNA, a small molecule, a cytokine, a chemokine, an antibody, or a radio-labeled compound.

4. The method of embodiment 1, wherein analyzing the composition or the molecular status of tissue or cells adjacent each reservoir includes one or more of immunohistochemistry (IHC), immuno-detection, in situ RNA hybridization, sequencing, protein isolation, nucleic acid isolation, microscopic observation, or staining.

5. The method of embodiment 1, wherein at least one microwell reservoir contains two different agents.

6. The method of embodiment 5, wherein each microwell reservoir contains a different agent, a different mixture of agents, and/or a different dosage of agents.

7. A method for determining efficacy of a compound in a tissue including:
   inserting into an ex vivo tissue sample outside of an organism an implantable microdevice including:
      a cylindrical support structure having microwells on a surface of or formed within the support structure, the microwells each containing and releasing after implantation a microdose of one or more active agents selected from therapeutic, prophylactic, and/or diagnostic agents;
      a microdose of one or more active agents in at least one microwell; and
      compound release mechanism including a polymeric matrix for controlling the release of the one or more active agents from the microwell;
   wherein the microdevice is configured to release the one or more active agents from the microwells to separate and discrete areas of tissue adjacent to each microwell without overlap between the discrete areas;
   incubating the ex vivo tissue sample with the inserted implantable microdevice in a sustaining ex vivo environment for at least 12 hours and no more than 10 days to produce agent-exposed tissue; and subjecting the agent-exposed tissue to multiplex immunohistochemistry (mIHC) analysis to determine the presence of Galectin-3 and Neuropilin-1, where presence or upregulation of either or both of Galectin-3 and Neuropilin-1 indicates the compound is effective.

8. The method of embodiment 7, wherein the tissue sample is a tumor tissue sample, and at least one of the agents is an anti-cancer agent.

9. The method of embodiment 7, wherein at least one agent is an anti-cancer agent, a carcinogen, a growth factor, an siRNA, a small molecule, a cytokine, a chemokine, an antibody, or a radio-labeled compound.

10. The method of embodiment 7, wherein analyzing the composition or the molecular status of tissue or cells adjacent each reservoir includes one or more of immunohistochemistry (IHC), immuno-detection, in situ RNA hybridization, sequencing, protein isolation, nucleic acid isolation, microscopic observation, or staining.

11. The method of embodiment 7, wherein at least one microwell reservoir contains two different agents.

12. The method of embodiment 7, wherein each microwell reservoir contains a different agent, a different mixture of agents, and/or a different dosage of agents.

13. A method of determining efficacy of an anti-cancer agent to treat a solid tumor, including:
   administering the anti-cancer agent, to a subject having a solid tumor, for a period of at least 2 days;
   subsequent to administering the anti-cancer agent:
      analyzing blood from the subject to determine presence and/or quantity of circulating galectin; and
      analyzing a tumor tissue sample from the solid tumor of the subject to determine the presence and/or quantity of neuropilin;
   wherein an increase in galectin and/or neuropilin compared to a control indicates that the anti-cancer agent is effective to treat the solid tumor.

14. The method of embodiment 13, wherein the solid tumor is a breast cancer tumor.

15. The method of embodiment 1, wherein the sustaining ex vivo environment includes the device described in FIG. 3D.

16. A method of assessing tumor cell response to a plurality of anticancer agents, the method including:
   obtaining a biopsy core of primary tumor tissue from a host;
   inserting into the biopsy core of primary tumor tissue an implantable drug-delivery microdevice including at least 8 microwell reservoirs, each reservoir holding one or more anticancer agents in solid form;
   maintaining the biopsy core of primary tumor tissue with the inserted microdevice in an extracellular matrix of stromal cells including endothelial cells, immune cells, and mesenchymal cells from the host, for at least 12 hours and no more than 30 days;
   formalin fixing and paraffin embedding the biopsy core of primary tumor tissue;
   analyzing the tumor tissue adjacent each reservoir using multiplex immunohistochemistry; and
   comparing the effects of each anticancer agent on adjacent tumor tissue.

Example 1: Next Generation Precision Medicine for Optimal Breast Cancer Treatment Selection In the era of personalized medicine, therapies can be perfectly suited to patients based on tumor molecular characteristics. The critical issue is that only a subset of individuals exhibit clear and durable responses. Achieving durable control will require systemic approach that will i) prevent "rewiring" that enables therapeutic escape, ii) block resistance mechanisms that result from bidirectional interaction with the environment and iii) reactivate and enhance immune surveillance. Novel strategies will be needed to counter all of these mechanisms via administration of series of drug combinations that change as the tumors evolve under treatment pressure.

We have developed a novel pre-clinical model system that allows for efficient, fast and harmless assessment of tumor cell responses to large numbers of drug (combination)s. Such system is based on the recently developed implantable screening microdevice that permits localized intratumoral drug delivery and provides with the ability to predict the drug efficiency and select the right candidate within few days after application (Jonas et al., Sci Transl. Med. 7, 284ra59, 2015).

The unique strength of our approach is that all measurements are performed within a live tissue in the native tumor microenvironment, and with an intact immune system. We combine this technology with multiplexed immunohistochemistry (Tsujikawa et al., Cell Rep 19:203-217, 2017) to bring in novel insights to mechanisms of response and resistance and propose rational combination treatment in breast cancers (BC). In parallel, through correlation studies we will upgrade the implantable methodology and build a novel pre-clinical model system that will serve as the next generation standard of care for treatment selection.

Figures 6A, 6B, 6C:
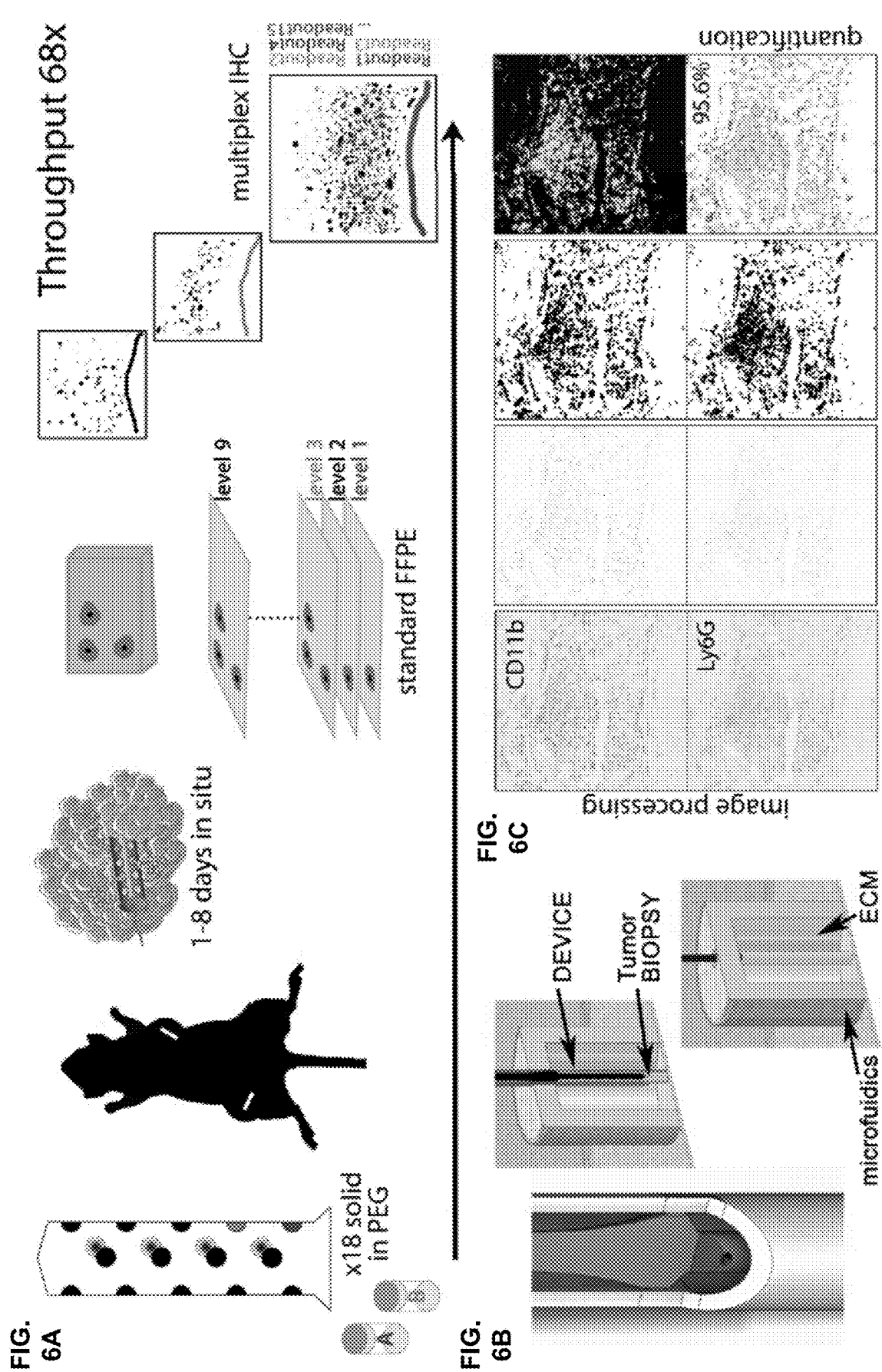
FIGS. 6A-6C. Exemplary process flow of the MNA system.

Multiplex nanodose assay (MNA) system and translation to breast cancer patients: The illustrated microdevice (FIG. 6A) is a non-toxic 4×0.8 mm resin cylinder with eighteen 200 μm deep reservoirs, that are packed with active compounds (drugs or drug combinations) in solid form. The device is implanted and stays in the tumor tissue for up to 8 days; after which the tumor/tissue surrounding the device is harvested with the device in place and formalin fixed and paraffin embedded (FFPE). The tumor tissue is analyzed adjacent to each drug well using multiplex IHC (mIHC) with antibodies that interrogate one or more of cleaved caspase activity, epithelial, mesenchymal, endothelial status, as well as immune composition and activity. FIG. 6B Design of the ex vivo platform using primary tumor biopsy. In principle, the system is similar to that illustrated in FIG. 6A, except that the tissue core/biopsy is removed from the subject, placed into a maintaining device that supports the tumor core in a substantially vertical position, then the drug-dispensing nanodevice is inserted into the tumor sample ex vivo. The ex vivo tumor sample is then maintained in a supportive environment, as described herein, for a period of hours to days, to allow the microdevice delivered drugs to act on adjacent tissue in the ex vivo tumor sample. Analysis can be carried out similarly to that used for in vivo embodiments. FIG. 6C Image processing of the acquired phenotypes. Briefly, red staining is extracted by color deconvolution, the image is transformed to 8 bit format, and automatic threshold is applied. Two iterations of noise removal/dilation/closure and erosion are run using binary images. Fiji4 plugins and macro is used for automated processing. Signal of individual markers are merged and the overlap is quantified.

Microenvironmental signals mediate resistance to targeted therapies in HER2+ breast cancers: FIGS. 7A-7D: Hepatocyte growth factor (HGF) and neuregulin-1b (NRG1b) mediate the resistance to tyrosine kinase inhibitors (TKIs), Neratinib and Lapatinib, in subtype-specific manner. While HGF is changing the TKI effectivity by decreasing apoptosis to normal levels in basal-like, JIMT1, NRG1b restores the proliferation in luminal-like BT474 tumors (Watson et al., Cell Syst. 1-14, 2018). The Initial discoveries were revealed using microenvironmental microarrays (MEMA, Gray and Korkola Lab). The implantable microdevice was used to validate these results in vivo which set the proof of concept and validated the correlative nature our implantable technique.

Figure 8C:
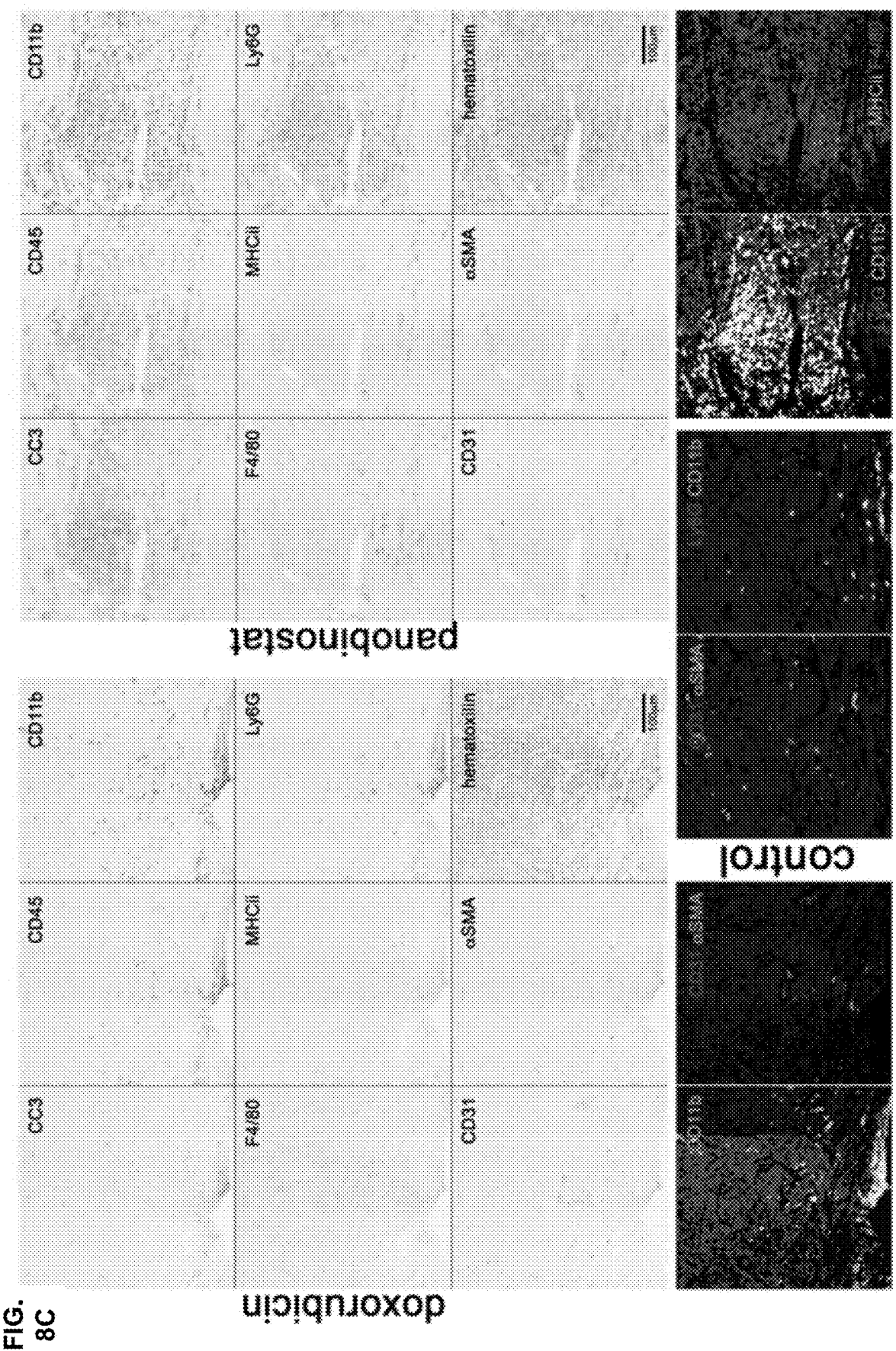
Figure 8E:
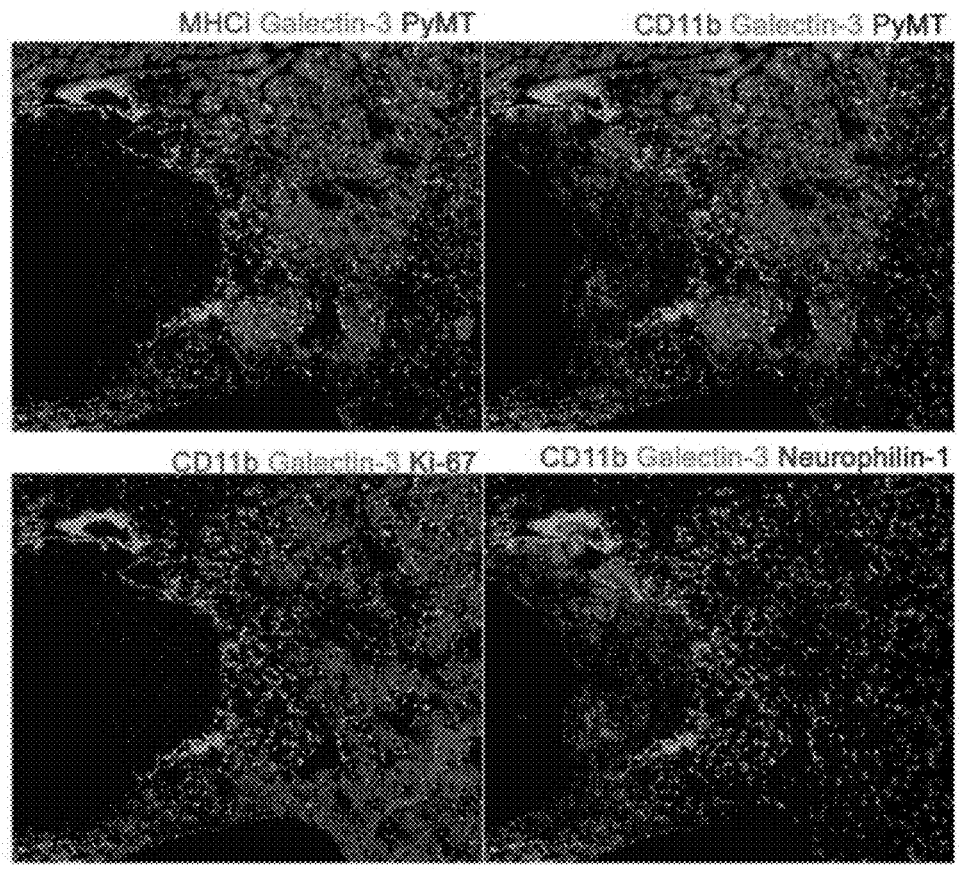
Figure 8F:
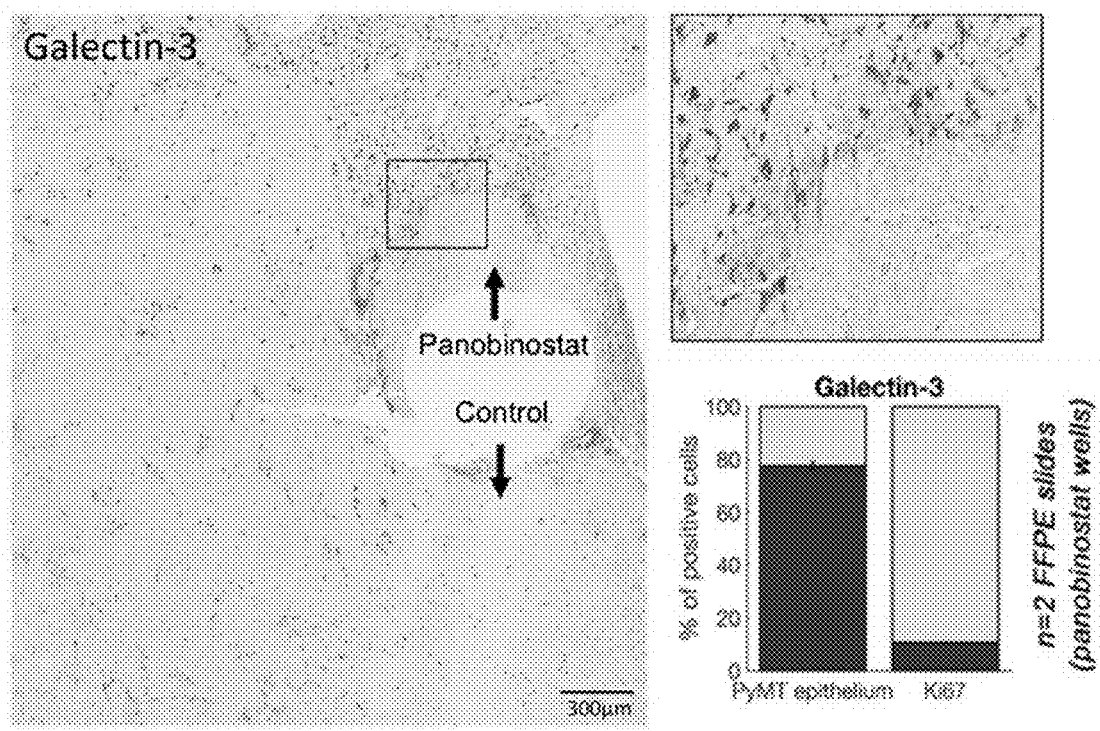
Figure 8G:
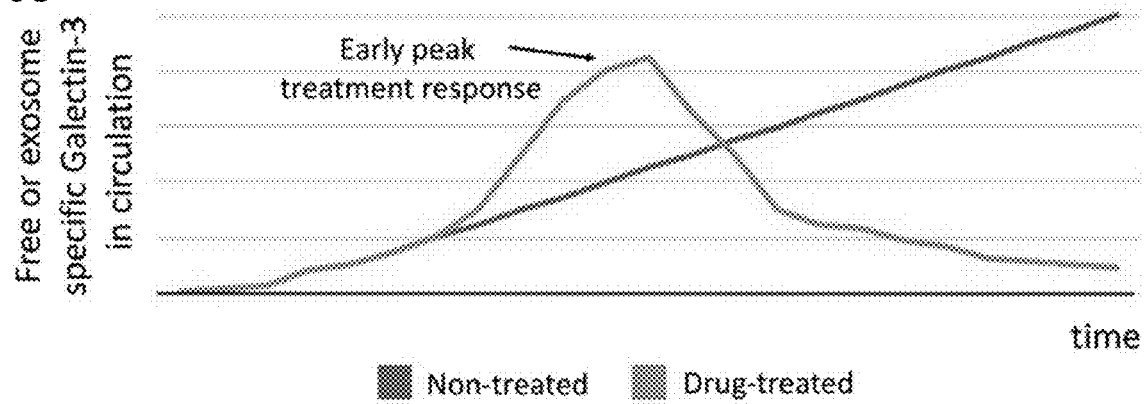
Figure 8H:
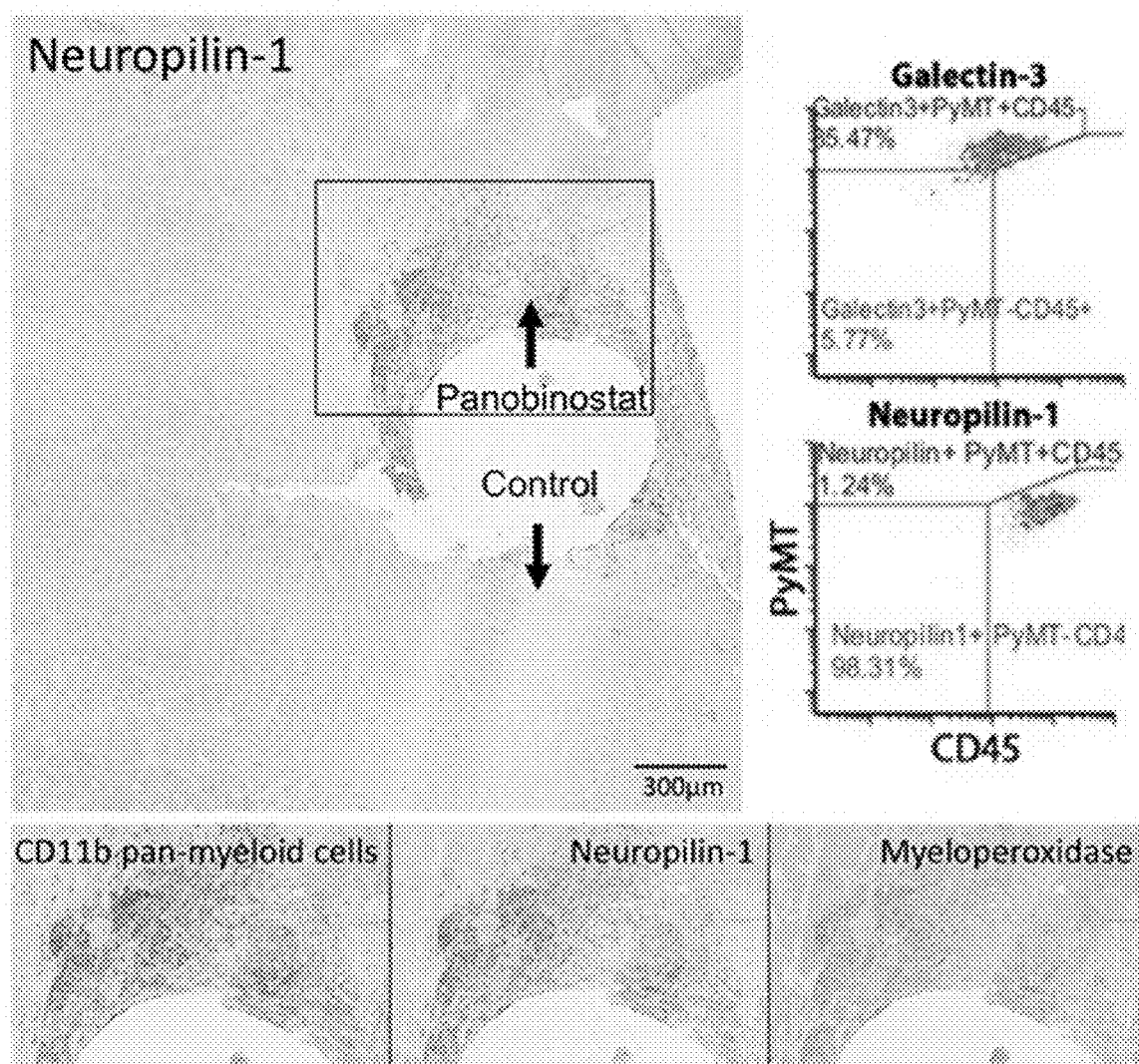
Figure 8I:
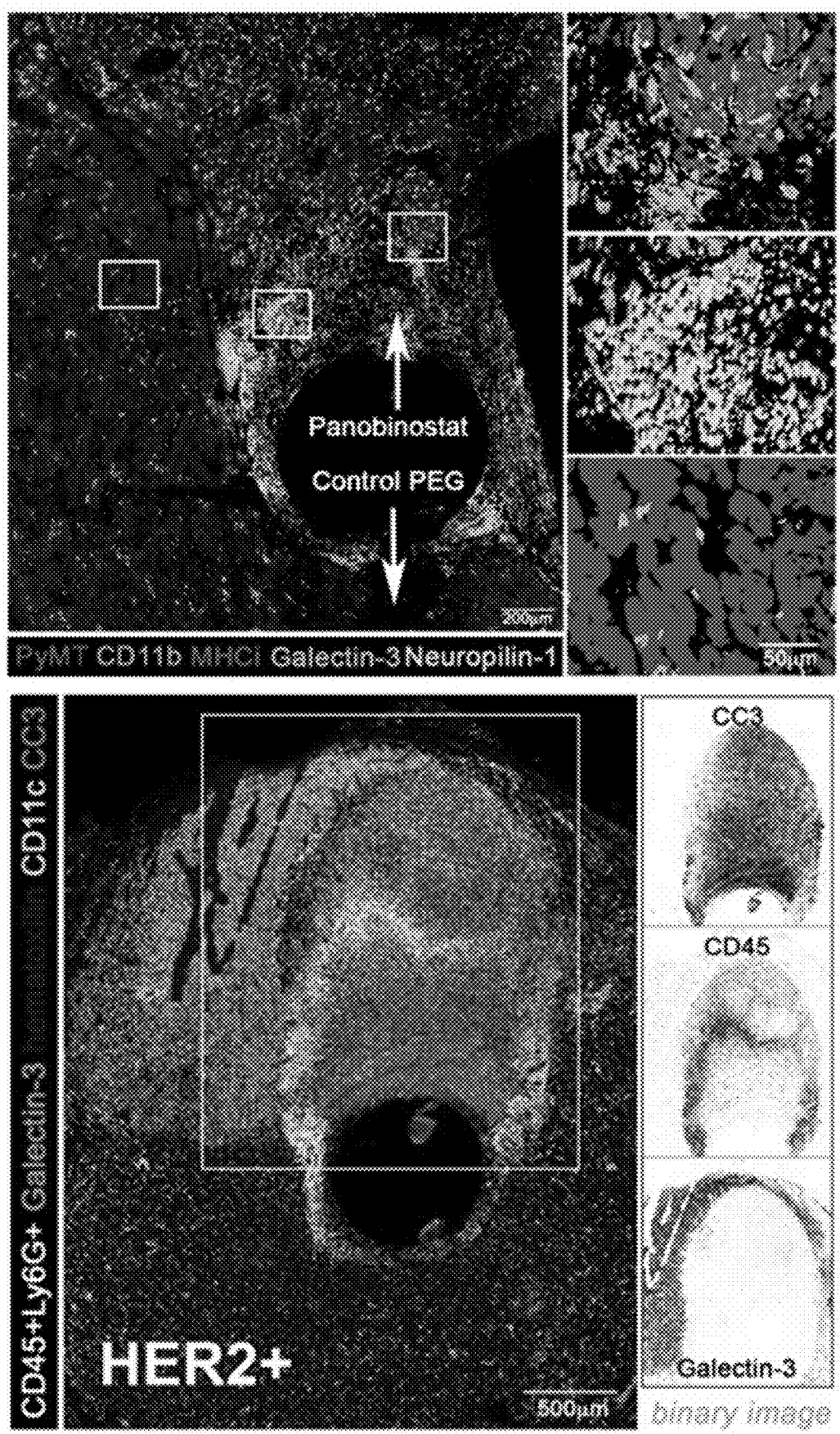
Figure 8J:
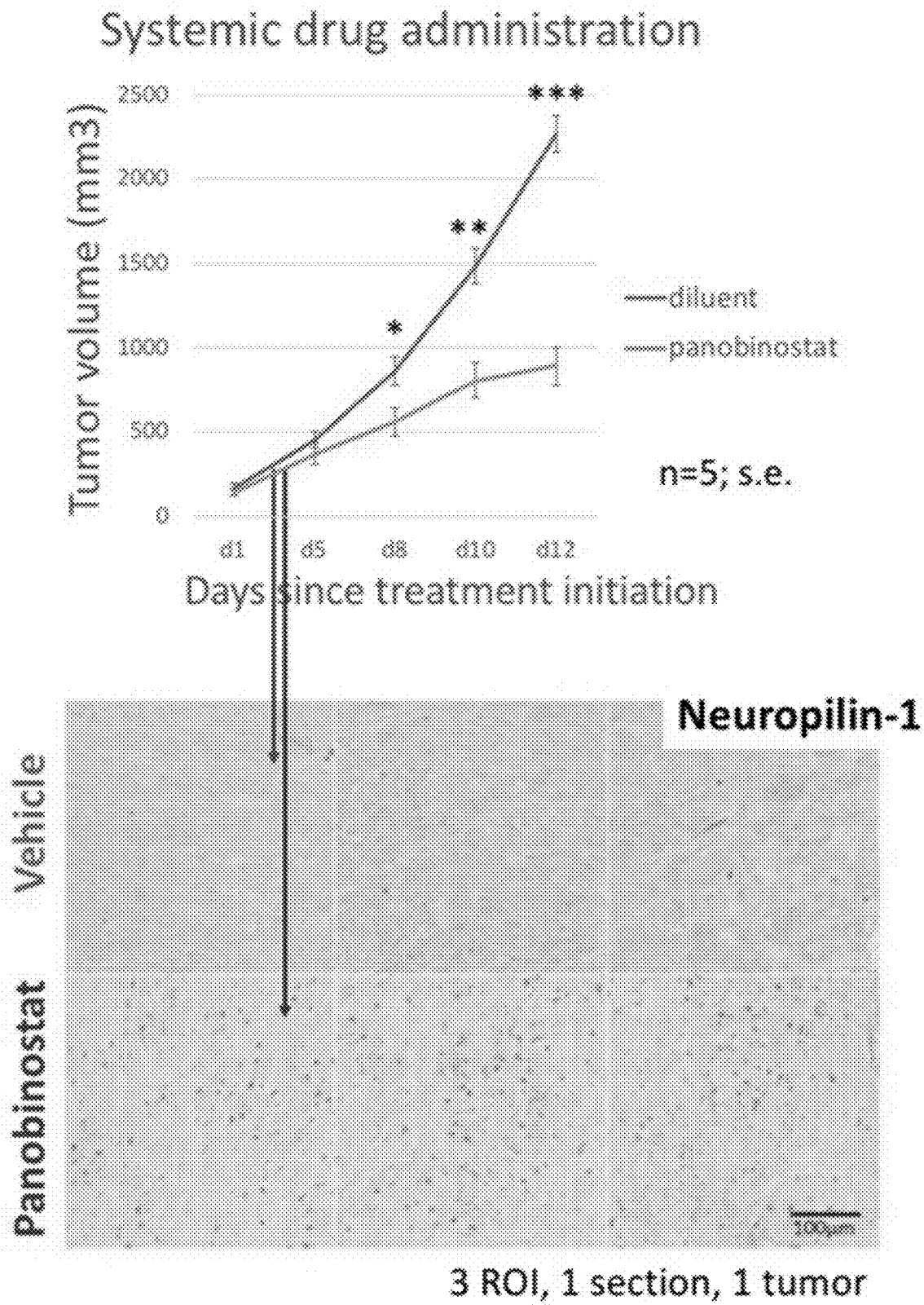
Figure 9:
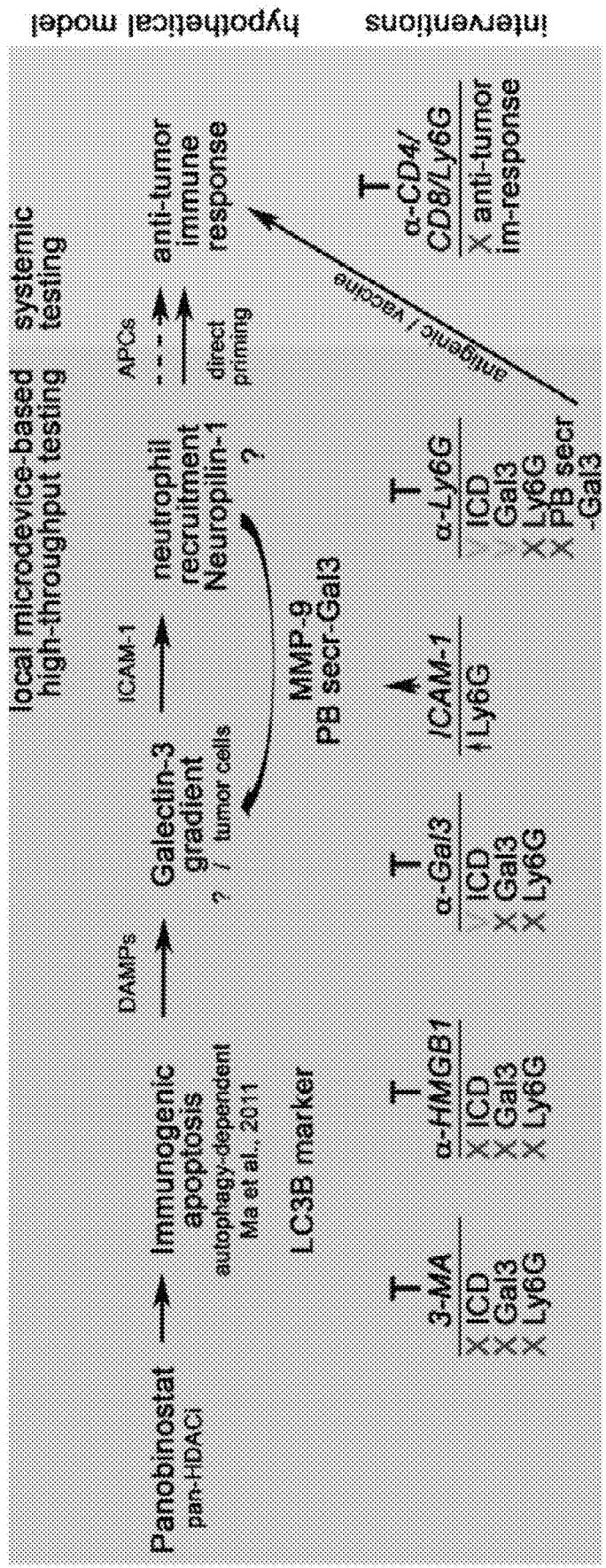
FIG. 9. Proposed pathways and gene involvement in panobinostat action. It is proposed that panobinostat increases immunogenicity through i) immunogenic cell death, ii) by enhancing molecules for antigen presentation and ii) by triggering professional APC and so presets the immune state for effective anti-PD-1 therapy. The immunogenic apoptosis, is dependent on autophagy to provoke anticancer immune response. Galectin-3 has been recently linked to recognizing "pattern of pathogenesis" and mediating autophagy (Feeley et al., *PNAS* 114(9):E1698-E1706, 2017). Also, it been described to be involved in slow rolling of leukocytes during acute inflammation through immunoglobulin like molecule ICAM-1. This and the spatial distribution of galectin-3 at the panobinostat reservoir leads to hypothesis that Galectin-3 plays critical role in early stage of antitumor immune response by linking Danger Associated Molecular Patterns (DAMPs) recognition with neutrophils recruitment during immunogenic apoptosis. The Neuropilin-1 profile suggest the function of the protein to be linked to i) Anti-tumor (N1) neutrophils, ii) antigen loading or direct presentation, iii) sequestering of pro-tumor compounds from microenvironment and iv) Galectin-3 cleavage are among candidate mechanisms.

Small scale screening and mIHC suggest synergy of panobinostat with anti-PD-1 therapy in the PyMT BC model: Results of a small scale screening are shown in FIG. 8A-8F. (FIG. 8A). A single PyMT mouse was implanted at day 105 and stayed in situ for 3 days. Mean intensity value of the CC3 signal was measured adjacent to the drug releasing reservoir and was normalized to control PEG only loaded reservoir. FIG. 8B) List of antibodies used in mIHC procedure. #marks the antigen retrieval cycle in the mIHC procedure. The basic MNA panel is in pink and is composed of 15 markers. Alternative antibodies, present in yellow, were tested in later cycles thus are source for replacement or a 2nd slide can be stained. M5/114.12.2 clone is used for MHCii, HLAA for MHCi. FIG. 8C) mIHC was applied to panobinostat and doxorubicin reservoir. Most remarkable phenotypes of the basic panel are displayed. Blue is hematoxylin. We observed presence of a very small population of F4/80+MHCii+ macrophages in an immediate proximity to the panobinostat reservoir. Such macrophage population have strong positive prognostic value, especially when located in intratumoral nests vs. stroma (Kawai et al., 2008). We expected that this population will be critical for effective panobinostat-mediated cell death and observed a significant decrease in CC3 signal next to panobinostat reservoir when mice were treated systemically by CSF-1R inhibitor for 10 days (FIG. 8D). Both molecules for antigen presentation, MHCii and MHCi, have increased presence in immunogenic vs. 'cold' tumors, inducing CTL infiltrate and predispose for checkpoint inhibitor response (Gibney et al., 2016). We observed a relative enhancement of MHCi on tumor cells right at the border of myeloid immune and tumor region (FIG. 8F). Next, in the MNA panel, we included two significant biomarkers, Galectin-3 and Neuropilin-1, that have strong prognostic and/or predictive value in other cancers but their functional role in BC is ambiguous or unknown, respectively. Using the second panobinostat replicate, we found that neuropilin-1 is co-localized with the CD11 b pan-myeloid infiltrate while galectin-3 is present outside this area in a gradient manner. The galectin-3 marker is present both on tumor and nontumor, but exclusively on non-proliferating (non-GO) cells. Values are means±s.e.m. (n=3 regions of interest in one sample for (FIG. 8F) and n=3 drug loaded wells for (FIG. 8D); significance was calculated by a two-tailed t-test with equal variance. Of note, early microdevice studies validated each well to be a biological replicate due to heterogeneous nature of tumors in general (Jonas et al., Sci Transl. Med. 7, 284ra59, 2015). Microfluidic ex vivo platform maintains the viability of the primary mouse tumor tissue.

On-going work relates to identifying the role of Neuropilin-1 and Galectin-3 in panobinostat mediated tumor-killing and in the anti-tumor immune response; confirming the usefulness of Galectin-3 as a predictive biomarker for positive treatment response in breast cancers; and performing correlative studies to determine the accuracy of the ex vivo platform and translate the technology towards breast cancer patients.

From the observed phenotypes, it hypothesize that panobinostat increases immunogenicity through i) immunogenic cell death, ii) by enhancing molecules for antigen presentation and ii) by triggering professional APC and so presets the immune state for effective anti-PD-1 therapy. The immunogenic apoptosis, is dependent on autophagy to provoke anticancer immune response. Galectin-3 has been recently linked to recognizing "pattern of pathogenesis" and mediating autophagy (Feeley et al., PNAS 114(9):E1698—#1706, 2017). Also, it been described to be involved in slow rolling of leukocytes during acute inflammation through immunoglobulin like molecule ICAM-1. This and the spatial distribution of galectin-3 at the panobinostat reservoir leads to hypothesis that Galectin-3 plays critical role in early stage of antitumor immune response by linking Danger Associated Molecular Patterns (DAMPs) recognition with neutrophils recruitment during immunogenic apoptosis.

Prior to data extension we will validate our preliminary results with statistical power. Jackknife resampling is recalculating t-test statistics after progressively removing individual replicates and will determine the number of replicates needed to acquire significant results. This applies for in vivo as well as microfluidic based experiments. Panobinostat will serve as a positive control.

A time course study and mIHC will be performed to define the sequence of events for effective therapy response. The high throughput nature of the microdevice technique will dramatically decrease the requirements on animal experimentation. An enhanced CTL infiltrate at the later, day 8 time point is expected for systemic anti-tumor immune response.

We will test the drug systemically, compare the tumor growth rate with conditions when conventional chemotherapies doxorubicin and paclitaxel are applied. Combination therapies and depleting antibodies will be used in the final validation of the model. Ideally Galectin-3−/− mouse model will be involved.

The potential role of Neuropilin-1 is less clear. i) Anti-tumor (N1) neutrophils, ii) antigen loading or direct presentation, iii) sequestering of pro-tumor compounds from microenvironment and iv) Galectin-3 cleavage are among candidate mechanisms.

Example 2

This example provides a system intended to address two challenges identified by the Breast Cancer Research Program, to revolutionize treatment regimens by replacing them with ones that are more effective, less toxic, and impact survival, and to eliminate the mortality associated with metastatic breast cancer. To accomplish these goes, there is described an analytical system that allows efficient, simultaneous optimization of drug combinations to increase tumor kill and to modulate the tumor microenvironment to enhance immune surveillance.

It is increasingly clear that durable control of metastatic human breast cancers will require combinations of drugs to achieve tumor cell kill, block escape pathways, enhance immune surveillance, and/or reduce microenvironment mediated resistance.

Immunotherapy with immune checkpoint blocking (ICB) antibodies combined with tumor targeted therapies is revolutionizing treatment for several solid malignancies but efficacy in metastatic breast cancer so far has been demonstrated for patients with triple negative breast cancer (TNBC). This lack of efficacy is in large part attributed to two mechanisms: i) Low antigenicity through decreased expression of major histocompatibility complex class I (MHC-I)—observed mainly in luminal estrogen receptor positive (ER+) BC and human epidermal growth factor receptor 2 positive (HER2+) BCs; and ii) naturally immunosuppressive tumor microenvironment (TME) associated mainly with TN and HER2+ BC. These mechanisms limit the CD8+ T cell-mediated anti-tumor response, which then cannot be leveraged to improve efficacy of ICB therapies. We hypothesize that significant improvements can be achieved by combining conventional chemotherapies and/or targeted anticancer agents that induce cells death to stimulate immune surveillance. However, further understanding of drug-immune system interactions is required to design the most effective and safe combinatorial regimens.

To rapidly test these interactions, our labs have developed a new high-throughput bioengineering tool called the multiplexed nanodose assay (MNA) that provides detailed information on responses of immune competent model tumors to drug combinations that can be analyzed to elucidate mechanisms of response and select effective combinations. Successful demonstration of efficacy and treatment response in the proposed pre-clinical setting will directly facilitate translational efforts using our MNA approach in the clinic.

Details of the method and preliminary data: The MNA system uses an implantable screening microdevice that permits localized intratumoral delivery of nanodoses of up to 18 different drugs or drug combinations at once and provides information that can be analyzed to identify effective combinations within few days after application (FIG. 10A). Specifically, the MNA system allows quantitative evaluation of the impact of drug combinations on tumor kill, immune response and microenvironment composition and organization in immunocompetent mice (FIG. 10B).

Nanodoses of the drugs are passively released from nanowells in the delivery device into confined, spatially separate tumor regions and regions in close proximity to each nanowell and responses are assessed in these regions using multiplex immunohistochemistry (mIHC) procedure (FIG. 11). This is a sequential IHC staining procedure that stains a single formalin fixed paraffin embedded (FFPE) tissue section cut through tissue adjacent to each well for multiple proteins that report on the cell types, states and functions in each section. The spatial architecture of the tumor is preserved in this process so the multiplex images can be analyzed computationally to assess changes in cell type, organization and molecular state as a function of distance from each nanowell. This allows assessment of drug induced tumor kill, infiltration and activity of immune cells, changes in fibroblast and ECM organization and distances between the diverse cell types. These data enable identification of drug combinations elicit the highest cell kill, most efficiently recruit desirable immune cells and decrease microenvironment mediated resistance (FIG. 10B, FIG. 13 and FIG. 14). The most effective combinations can then be tested for efficacy in more conventional whole animal experiments (FIG. 17).

In this project, we will focus our efforts on ER+ BC as, to current date, this breast cancer subtype has not responded well to immune checkpoint blocking therapies. Our work is guided by preliminary studies in which we analyzed publicly available transcriptomic profiles measured for breast cancer cells treated with therapeutic agents to identify drugs that increase MHC-I expression on tumor cells. We postulate that these drugs will be likely to elicit effective antitumor immune response. We identified panobinostat, a pan-histone deacetylase inhibitor (HDACi), as the top candidate to upregulate MHC-I on estrogen receptor positive (ER+) MCF7 cells (FIG. 12).

We used our MNA system to quantitatively assess the response of late stage tumors that arose in the immunocompetent MMTV-PyMT (mouse mammary tumor virus-polyoma middle tumor-antigen) mouse model. The tumors that arise in MMTV-PyMT mice closely resemble the progression and morphology of human breast cancers. Importantly, although expression of ERα decreases in MMTV-PyMT tumors as they progress to late carcinoma, expression profiling shows that they cluster with the luminal breast cancers.

Figure 13A:
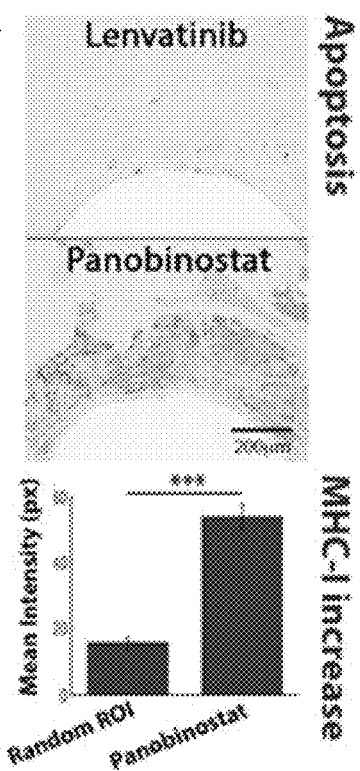
FIGS. 13A-13B.
Figure 13B:
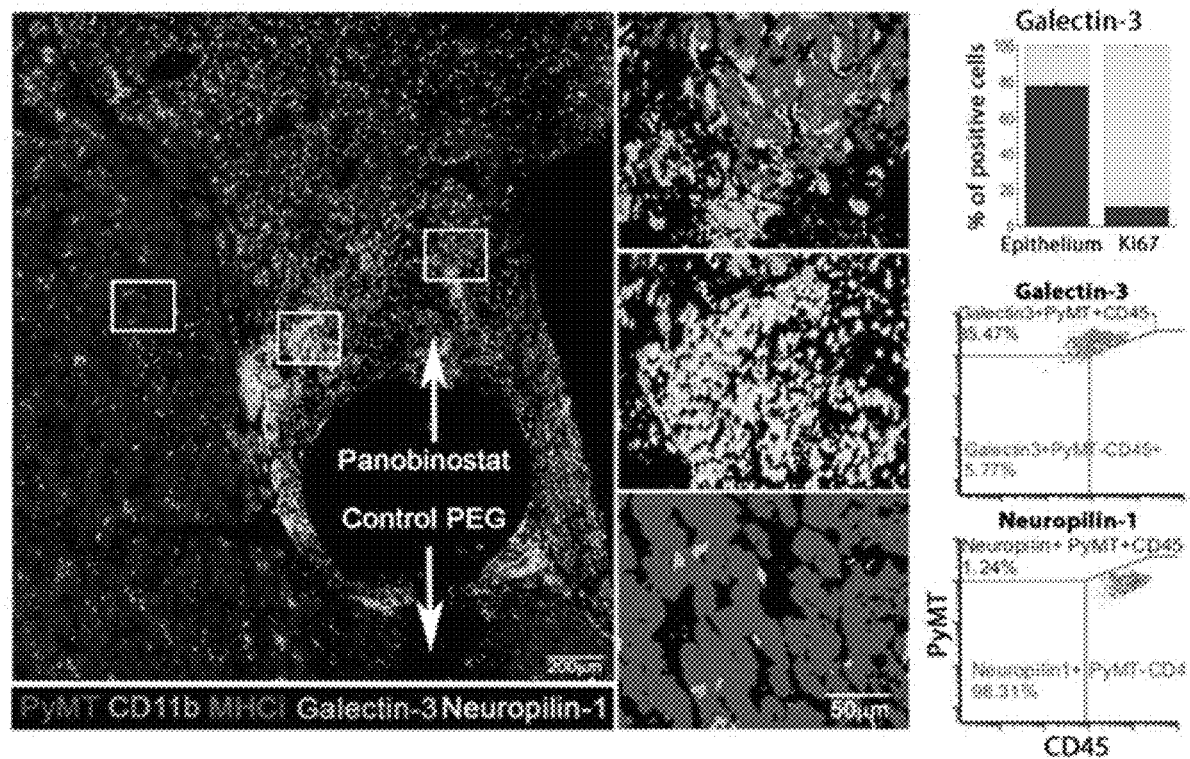

Tumors in MMTV-PyMT mice were implanted with the nanodosing microdevice loaded with polyethylene glycol (PEG) control, panobinostat, two conventional chemotherapies used in breast cancer treatment, and two targeted anti-cancer therapies—with modes of action different from panobinostat. The implanted tumors were extracted, fixed and assessed of apoptosis by cleaved caspase-3 (CC3) and MHC-I using conventional immunohistochemical staining, 3 days after exposure to the various drugs. This analysis showed that panobinostat significantly increased apoptosis in close proximity to the nanodosing well (FIG. 13A). We also observed an increase of MHC-I on tumor cells approximately 500 µm from the reservoir at the outer border of the dying cells (FIGS. 13A and 13B). Because panobinostat met both our criteria for ICB response (CC3 and MHC-I increase), we applied the multiplex IHC staining (FIG. 11) and performed multivariate single cell analysis to identify cellular and molecular mechanisms driving this positive response. We found that response to panobinostat also was associated with infiltration of a small population of professional antigen presenting cells and heavy infiltrate of cytotoxic neutrophils (FIG. 10B and FIG. 13B).

We took the advantage of multiprotein staining capability of mIHC staining to add two biomarkers, Galectin-3 and Neuropilin-1, to the readout panel. These proteins have been reported to be related to danger associated molecular patterns and CD8+ T cell priming activity, but their potential utility as biomarkers of immune response in breast cancer had not been explored. Our MNA analysis showed that increased levels of these proteins was positively correlated with panobinostat induced immune cell recruitment. While ~85% of Neuropilin-1 positive cells were cytotoxic neutrophils; Galectin-3 was present outside the CD11b pan-myeloid region, was enriched on tumor cells close to MHC-I, was present with gradient profile and specifically on non-proliferating cells (FIG. 13B).

A recent report showed that drug-mediated apoptosis associated with heavy infiltration of cytotoxic neutrophils was linked to immunogenic cell death. Based on that report, and our observation of panobinostat induction of cytotoxic neutrophils invasion, we performed a functional, whole animal immunization study to determine whether panobinostat-induced tumor killing was also immunogenic (immunogenic antigen specific immune response). Our study showed that immunization with panobinostat-treated cells resulted in delayed tumor growth as compared to control, however, the protection against tumor development was not durable after 23 days (FIG. 14B), suggesting resistance mechanisms have been induced. To interrogate potential pathways of resistance, we combined panobinostat with other drugs increasing MHC-I expression on tumor cells from FIG. 12 except that we used FDA-approved variants targeting similar pathways. We found that combination of panobinostat with the BCL2 inhibitor, venetoclax, decreased the frequency of Ly6G positive neutrophils and completely cleared tumor cells by day 8. Interestingly, the border of the cleared tissue was occupied by professional antigen presenting CD11c+MHCii+ dendritic cells (FIG. 14B); cell populations linking the innate and adaptive immunity.

Our studies show the power of the MNA system in accessing cytotoxic and immune activation potential of drug combinations. This system may also be used to further explore the cellular and molecular mechanisms driven by drug combinations.

The systems may also help in identifying the sequence of cellular and molecular events at the interface of dying tumor cells and the tumor immune microenvironment. The MNA system may be used with a defined set of established cell-specific markers to perform time course studies to delineate sequence of events driving effective tumor killing and consequent immune responses. Spatial information of cell coordinates can be used to measure changes in tumor and immune system composition, molecular status and organization following treatment with tested drugs or drug combinations in the implantable microdevice over time. Quantitative image analysis tools can be used to generate a map of interrelated phenomenon at 24 h, 48 h, 3, 5 and 8 days for single drugs and a drug combination to help discover putative causal relationships evolving at the intersection of dying tumor and tumor microenvironment.

The systems may also be used to determine the functional role of specific proteins in drug immune modulation. Blocking antibodies added to a drug in the MNA help determine the functional role off the protein(s) in a drug's mode of action by quantitative measure of tumor killing and consequent immune responses. mIHC staining can be extended to further characterize the type, function and activity of the defined protein in protein positive cells. Specific focus may be placed on events related to the "danger signal" recognition, autophagy, anti-tumor (N1) neutrophils and MHC-I antigen presentation machinery.

The ability of combination therapy to improve the immune checkpoint blocking efficacy in a whole animal approach may also be determined. Drug combinations may be administered systemically and used to measure the effect on tumor growth, metastatic dissemination, increase of intratumoral CD8+ T cell infiltration and synergy with PD-1 blockade therapy as compared to single drugs and controls. The treatment response will be correlated with the MNA-discovered histopathological signature to determine its early predictive value stratify ICB benefit. This will also foster evaluation of the predictive nature of the MNA system as compared to systemic drug administration.

Figure 15A:
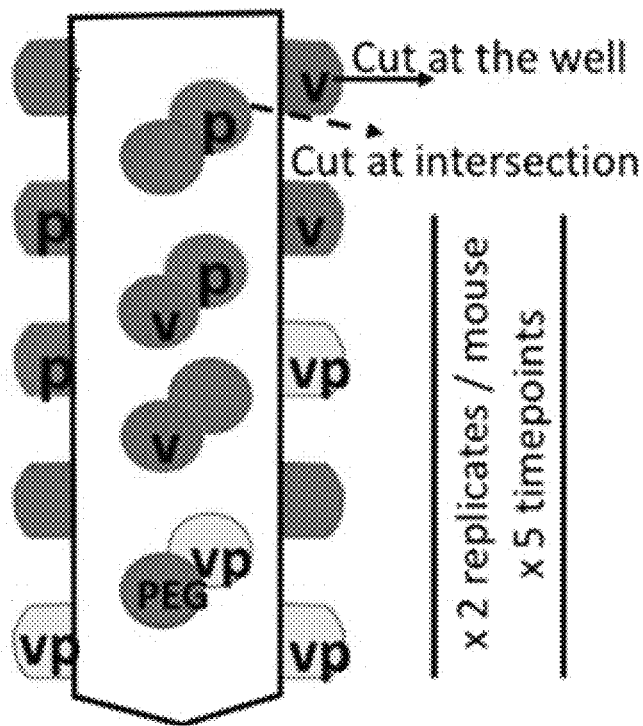
FIGS. 15A-15D. Schematic presentation of microdevice loading strategy (FIG. 15A), image analysis (FIG. 15B); and preliminary results (FIG. 15C) reflecting tumor microenvironment profiling after sub-compartmentalization of the assay with distance from the well-being related to drug concentration. (i) The borders of the regions will be identified automatically using the contour detection function from MATLAB (The MathWorks, Inc). This process will define the "zones" in the assay area and will account for the potential signal distortion—expected pitfall (FIG. 15B). Signal distortions are expected as tumor is not a homogeneous material. The borders through automatic region detection will be defined by the biological phenotype and will be overlaid with the drug release profile as defined by anti-PEG antibody (from adjacent slide). ii) Next, within each zone I will average the results from smaller regions of interest (FIG. 15C). Analyzing and averaging the results from the smaller ROIs instead of analyzing the whole region will compensate for the number of cells and will provide more unbiased analysis. The number of ROIs will depend on the overall occupancy of the zone. E.g. immediate zone might have lower n as compared to proximal or distal ROIs. We plan to analyze, however, at least 2 ROIs/sample/ZONE—thus a total of 2×6=12 ROIs per timepoint/ZONE. (iii) Inside the ROIs, I will determine the geographical interaction (FIG. 15D) between individual cells types by proximity measurements using the pdist2 function MATLAB (The MathWorks, Inc.) which returns the distance of each pair of observations (cell type) in X and Y using the metric specified by Euclidean distance. (iv) To identify interrelated phenomenon, I will set the threshold distance to 100 µm, which represents ~5-10 cells. I assume that cells within this distance range might have effect on each other in a complex tissue. Percentage of positivity will quantify interrelated cell phenotypes. Early proximity measures suggest that the CC3 signal present immediately at the panobinostat well at 3 days is mediated by cytotoxic neutrophils rather than by e.g. F480 macrophages or by CD8+ T cells (FIG. 15D). The same analysis will be applied (1) to all individual zones in the drug effected area (immediate, proximal, border, distal); plus random, random stromal regions, (2) to all timepoints and (3) to all cell types (defined by set of probes). Outcome: Quantitative measures will generate a map of interrelated phenomenon over time for single therapies, for the intersection of the two drugs and their combination after sequential release. The study will provide comprehensive direct evidence of cellular events evolving at the intersection of dying tumor and TME and will help to identify cause-consequence cell associations critical for positive drug response.

The present systems and devices further help identify the sequence of cellular and molecular events at the interface of dying tumor cells and the tumor immune microenvironment. Devices will be loaded with individual drugs and combinations thereof using four replicates (FIG. 15A). The stoichiometry of the loaded drugs may be conserved. Drug-release properties have been previously established as a biological replicate due to the heterogeneity of the tumors. In the MNA assay, we prefer to use mouse models with spontaneously developing tumors to account for all steps of immune-editing (27). At least two devices may be implanted to one mouse as the tumor development is multi-focal in this model. Considering 25% replicate loss due to the technical issues (well implanted close to the tumor border or necrotic area), one can analyze 8*0.75=6 assay areas from one mouse per time point. Previously we identified that 3 replicates per condition are sufficient to identify significant changes between functionally different conditions. Thus, this experimental design may reliably detect drug-mediated phenotypes.

Figure 15B:
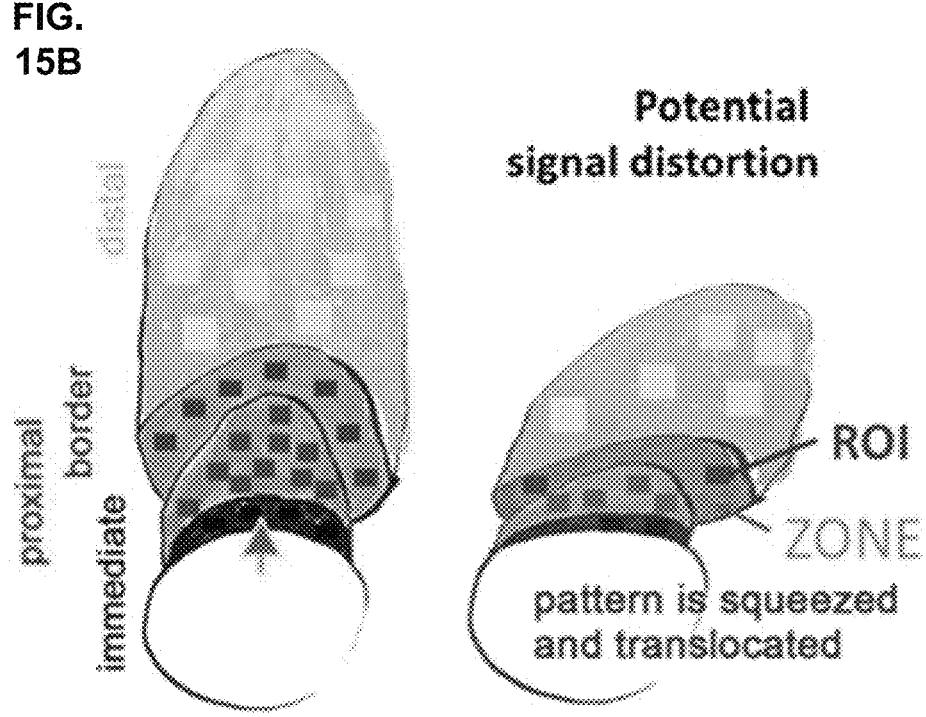
Figure 15C:
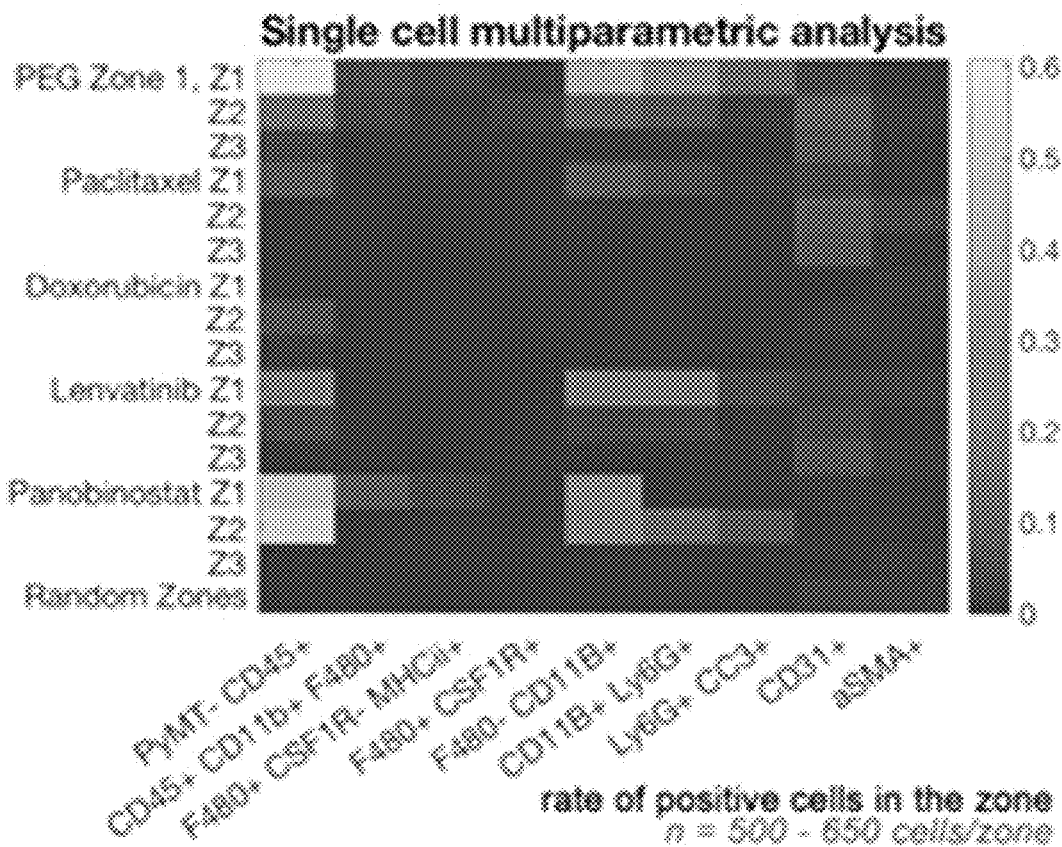

Quantitative image analysis can be conducted to identify cellular associations. Single cell multivariate analysis may be performed as shown (FIG. 10B), except that, in some embodiments, the assay area may be divided into sub-compartments with distance from the well-being related to drug concentration (FIG. 15B).

i) The borders of the regions may be identified automatically using the contour detection function from MATLAB (The MathWorks, Inc). This process will define the "zones" in the assay area and will account for the potential signal distortion—expected pitfall (FIG. 15B). Signal distortions are expected as tumor is not a homogeneous material. The borders through automatic region detection are defined by the biological phenotype and overlaid with the drug release profile as defined by anti-PEG antibody.

ii) Next, within each zone the average of the results from smaller regions of interest are taken (FIG. 15C). Analyzing and averaging the results from the smaller ROIs instead of analyzing the whole region compensates for the number of cells and provides more unbiased analysis. The number of ROIs depends on the overall occupancy of the zone. E.g. immediate zone might have lower n as compared to proximal or distal ROIs. Analysis can then be conducted with at least 2 ROIs/sample/ZONE—thus a total of 2×6=12 ROIs per timepoint/ZONE.

(iii) Inside the ROIs, one can determine the geographical interaction (FIG. 15D) between individual cells types by proximity measurements using the pdist2 function MATLAB (The MathWorks, Inc.) which returns the distance of each pair of observations (cell type) in X and Y using the metric specified by Euclidean distance.

Figure 15D:
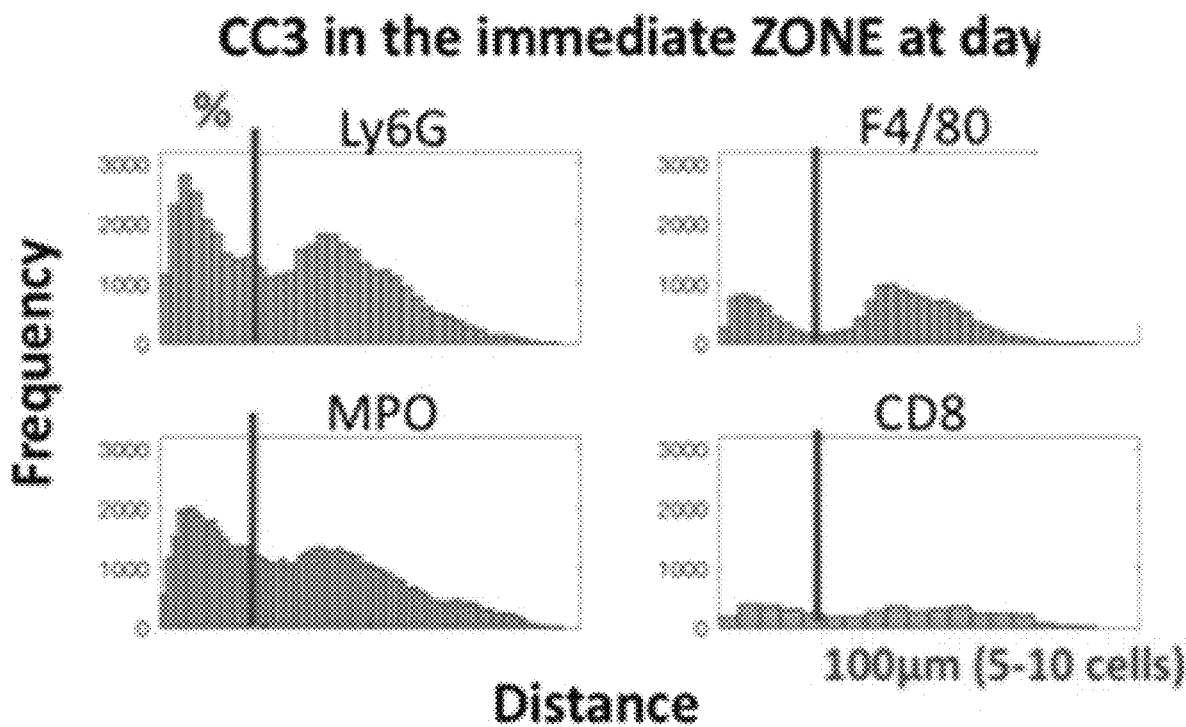

(iv) To identify interrelated phenomenon, the threshold distance is set to 100 μm, which represents ~5-10 cells. The cells within this distance range might have effect on each other in a complex tissue. Percentage of positivity will quantify interrelated cell phenotypes. Early proximity measures suggest that the CC3 signal present immediately at panobinostat wells at 3 days is mediated by cytotoxic neutrophils rather than by e.g. F480 macrophages or by CD8+ T cells (FIG. 15D). The same analysis is applied (1) to all individual zones in the drug effected area (immediate, proximal, border, distal); plus random, random stromal regions, (2) to all timepoints and (3) to all cell types (defined by set of probes).

Outcome: Quantitative measures will generate a map of interrelated phenomenon over time for single therapies, for the intersection of the two drugs and their combination after sequential release. The study will provide comprehensive direct evidence of cellular events evolving at the intersection of dying tumor and TME and will help to identify cause-consequence cell associations critical for positive drug response.

We can also determine the functional role of specific proteins in a particular drug's mechanism of action, for instance, the role of Galectin-3 and Neuropilin-1 in panobinostat immune modulation. We have shown that panobinostat mediates immunogenic cell death associated with upregulating MHC-I expression on tumor cells, and recruitment cytotoxic neutrophils and that the expression of Galectin-3 and Neuropilin-1 on tumor cells and neutrophils, respectively, correlated with therapeutic response.

The functional role of Galectin-3 and Neuropilin-1 in panobinostat mechanism of action may also be determined by applying 10% of Galectin-3 and Neuropilin-1 blocking antibody on top of panobinostat, followed by incubation in the devices for 2 and 3 days in vivo (FIG. 16A). Previously we have shown that this concentration and incubation time mediates physiologically relevant effects maintaining the half-life of the protein (10). We have also already shown that Galectin-3 and neutrophils (by anti-Ly6G) antibody decreased CC3 mediated by panobinostat, suggesting that these cell populations are functionally important for panobinostat mediated anti-tumor activity (FIG. 16B). The anti-Neuropilin-1 antibody can be added to the set of interventions and TME-profiling performed with the 21 established probes similar to above. A total of 2 mice may be used to test 8 conditions with 8 replicates. Finally, a total of 6 assay areas (8×0.75) can be analyzed for the 2 day and 3 day time point each. The analysis will quantitatively evaluate the contribution of each protein to each phenotype in defined assay zones. A total of 48 mice would be required to test the same set of interventions with standard whole animal approaches.

Based on the spatial distribution of Galectin-3 and Neuropilin-1, and the literature review, Galectin-3 and Neuropilin-1 plays a critical role in early anti-tumor in BC by linking "danger signals" with activation of adaptive immunity. mIHC staining may be extended to test this hypothesis (FIG. 16C), with specific focus on i) events related to the "danger signal" recognition (19), autophagy (24, 29) and MHC-I antigen presentation machinery (30, 31) (to test the role of Galectin-3), and on ii) anti-tumor (N1) neutrophils (17, 32) (to test the role of Neuropilin-1). As an alternative, the high-throughput nature of the MNA system may be used to perform a systematic perturbation study using small molecule inhibitors, blocking antibodies and cytokines to rapidly test the hypothetical mechanistic model (FIG. 16C, bottom part of the panel).

It is also possible to determine the ability of combination therapies, such as panobinostat/venetoclax, to improve the ICB efficacy in a whole animal approach. The predictive value of our MNA system can be addressed, for example, by administering panobinostat systemically through intraperitoneal injection. We have shown that panobinostat significantly decreases the tumor growth, as well as increases intratumoral Neuropilin-1 (mIHC staining ongoing) as compared to control (FIGS. 17A and 17B), which in part validates the correlative nature of the MNA system compared to systemic drug administrations.

Figure 17C:
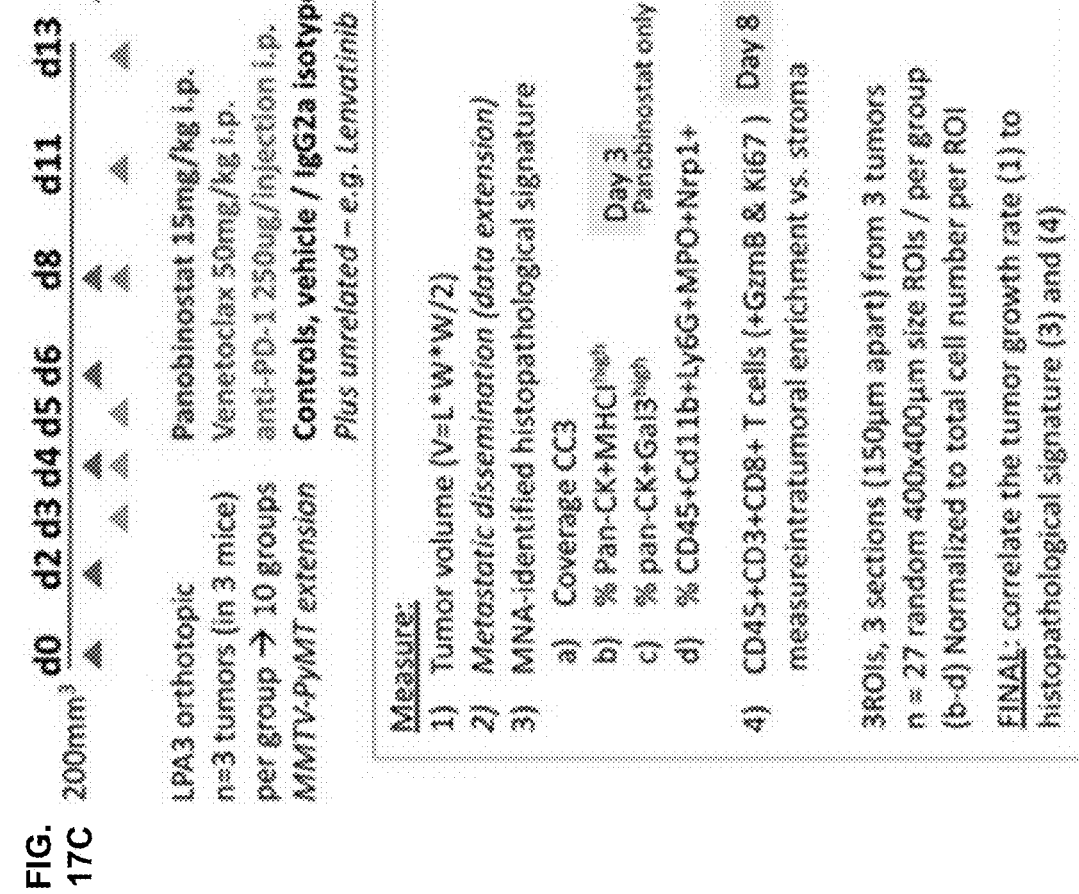
FIGS. 17A-17C. Preliminary data (FIG. 17A) and (FIG. 17B) and experimental plan (FIG. 17C) testing the efficacy of Panobinostat/Venetoclax combination after systemic drug administration and expected biomarker response.
Figure 17A:
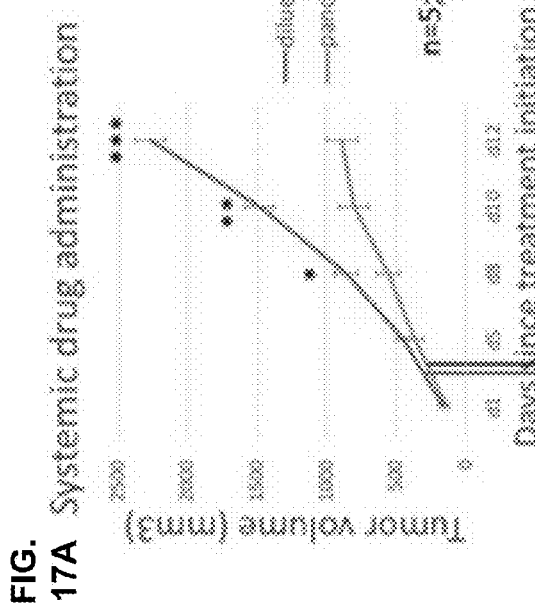

One can also test the potential of combinations, such as Panobinostat/Venetoclax, to further control tumor growth, as well as to trigger effective anti-tumor response and synergize with anti-PD-1 therapy (FIG. 17C). This can be studied using syngeneic ER+ LPA3 mouse model with established tumors. Based on our previous studies (FIG. 19A), the minimal number of required animals to obtain significant data is n=3/group. This is defined by a formula $n= ((sd_{group1}^2+Sd_{group2}^2)*Z)$ $(mean_{group1}-mean_{group2})^2$, $Z=13$ for $\alpha=0.05$ and $\beta=0.05$ (tabular parameters). Dose and schedule of the treatment can be determined by our preliminary data for panobinostat (FIG. 17A) and from the literature for venetoclax and anti-PD-1 antibody. Groups should be checked for signs of toxicity and weight loss. Female mice may be used in all studies, as male breast cancer is a rare disease that accounts for less than 1% of all BCs.

Figure 17B:
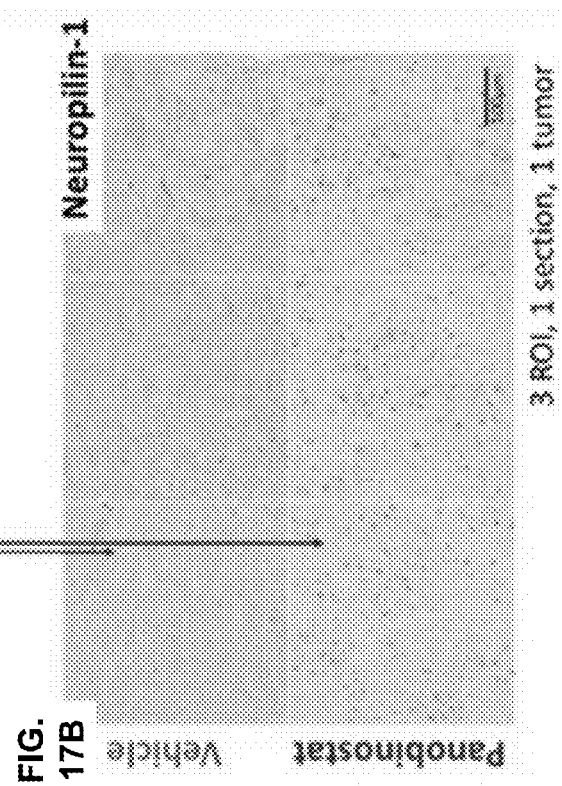

Tumors may be collected (i) at day 3 and analyzed for a local panobinostat signature (CC3, MHC-I, Galectin-3 and Neuropilin-1 increase), and (ii) at day 8 and for increased intratumoral CD8+ T cell increase as compared to stroma. The phenotypes are then quantified and correlated with the response rate to anti-PD-1 therapy (FIGS. 17B and 17C).

The MNA system can also be used to search for other drugs that synergize with panobinostat therapeutic response or will antagonize processes mediating resistance to therapy. Candidate therapies can be tested, for instance, for autophagy inducers, as ICD is dependent on autophagy; hypoxia and TGFβ signaling inhibitors for N1 neutrophil polarization; and epithelial to mesenchymal (EMT) transition inhibitors, as EMT was repeatedly linked to decreased MHC-I antigenicity. The synergy of panobinostat may also be tested with other MHC-I inducers from the transcriptomic analysis (FIG. 12). FDA-approved compounds targeting the same signaling pathways will be preferred.

Example 3: Neutrophil Polarization to Improve Immunotherapy in Breast Cancer

Immune checkpoint blockade (ICB) therapies, have shown promise in some solid and "liquid" heme malignancies, but good efficacy in breast cancer (BC) has not been reported (Voorwerk et al., Breast Cancer Manag. 7(1), TMT05, 2018). The most recent data reinforces the concept that ICB therapies are not effective unless primary antitumor response—cell death—is generated (Patel & Minn, Immunity. 48:417-33, 2018; Luo et al., Nat Commun 1-11, 2018, doi.org/10.1038/s41467-017-02630-w). We have identified that panobinostat, a pan-histone deacetylase inhibitor, induced immunogenic cell death in mammary carcinoma, which was associated with strong infiltration of Neuropilin-1 positive cytotoxic neutrophils. We hypothesize that Neuropilin-1 cells are antitumor neutrophils with tumor killing capacity. As such, one can investigate if therapeutic interventions further polarizing neutrophils towards antitumor phenotype will synergize with panobinostat mechanism of action to induce baseline immune state for effective ICB response. Also addressable is the possibility that Neuropilin-1 can serve as an early biomarker to stratify ICB benefit.

Polarization of tumor associated neutrophils to modulate disease progression:

Neutrophils are the first defenders and the most abundant effector cells of the innate immune system. Upon sterile or microbe-triggered signals, they rapidly migrate from bone marrow to the damaged site, phagocytose and release reactive chemicals and proteases. Given that this neutrophils arsenal can also damage host tissue, its deployment is tightly regulated for normal tissue homeostasis. Functional diversity exists between different neutrophils subpopulations as a result of specialization and adaptation to changing environment (Nicolás-Ávila et al., Immunity, and Cancer. Immunity 46:15-28, 2017). In the context of cancer, immune cells, as well, exhibit functional plasticity and, depending on the tumor milieu, they can undergo phenotypic change—regarded as alternatively activated or polarized. The concept of immune cell polarization is mostly known for macrophages but recent data indicate that tumor-associated neutrophils (TANs) also have differential states of activation, suggesting a classification scheme to more "beneficial" tumor killing (N1) versus protumorigenic (N2), which contribute to tumor progression (Fridlender et al., Cancer Cell 16:183-94, 2009; Shaul et al., Oncoimmunology 5:1-14, 2016; Andzinski et al., Int J Cancer. 138:1982-93, 2016). N1 and N2 neutrophils differ in their expression of proinflammatory (ICAM-1 and TNFα) and angiogenic factors (VEGF), as well as in their ability to promote or inhibit effector T-cells (Hagerling & Werb, Semin Immunol. 28:197-204, 2016). Such plasticity of neutrophils provides a potential target for therapies that increase their antitumor effect while limiting protumor functions. Definitive answers on neutrophil polarization, their isolation and further phenotypic characterization are limited in part because specific markers discriminating between anti and protumor neutrophils have yet to be identified.

Panobinostat induces immunogenic cell death associated with Neuropilin-1 neutrophil infiltration: We have developed a novel pre-clinical model system—the Multiplex Nanodose Assay (MNA)—that enables a comprehensive single cell analysis of drug-mediated effects in complex tumor microenvironment (TME). The MNA is based on a recently developed implantable microdevice that performs drug sensitivity testing of multiple drugs at once inside a living tissue (FIGS. 18A and 18B) (Jonas et al., Sci Transl Med 7:284ra57, 2015; Watson et al., Cell Syst 1-14, 2018, doi.org/10.1016/j.cels.2018.02.001). The drugs are passively released into distinct tumor regions and we analyze the drug mediated effects in close proximity to the drug releasing well by multiplex immunohistochemistry (mIHC) (FIG. 18C). This is a sequential IHC staining on a single formalin fixed paraffin embedded (FFPE) tissue for multiparametric characterization of single cells similar to flow cytometry, except that the cells are studies in their natural intact environment (Tsujikawa et al., Cell Rep 19:203-17, 2017; Chang et al., Proc Annu Int Conf IEEE Eng Med Biol Soc EMBS. 4046-9, 2017). The spatial relation of the functionally different populations facilitates identification of the drug-mediated cellular mechanisms. This knowledge can be then translated to rapidly identify rational combination treatment strategies.

With the MNA, we have performed a small scale screening using 5 FDA approved drugs in immunocompetent mouse models of triple negative and HER2+ breast cancer with late stage spontaneously developing tumors. The implanted tumors were extracted and processed by histochemistry for analysis of apoptosis by cleaved caspase-3 (CC3) 3 days of exposure to the various drugs. Panobinostat, a pan-histone deacetylase inhibitor, significantly increased the rate of apoptosis in close proximity to the nanodosing well (FIG. 18B). In an immunization study we validated panobinostat induced tumor cell death to be immunogenic (FIG. 19A). This was further confirmed by measuring increased antigen presentation on tumor cells after panobinostat treatment both in transcriptomic analysis as well as in the MNA system.

Since panobinostat-mediated effects in vivo are likely linked to effective anti-tumor immunity and increased response to PD-1 blockade therapy, we took a closer look at the immediate interaction between dying tumor cells and tumor microenvironment. For this, we used the multiplex IHC staining and performed comprehensive multivariate single cell analysis (Tsujikawa et al., Cell Rep 19:203-17, 2017; Chang et al., Proc Annu Int Conf IEEE Eng Med Biol Soc EMBS. 4046-9, 2017) in close proximity to the drug releasing well. In the multiplex readout panel, we incorporated stains that interrogate basic drug-sensitivity testing, epithelial, mesenchymal, endothelial compartment, but mainly multiple markers of immune composition and activity. With this system, we identified that the drug-mediated apoptosis was associated with increased infiltration of cytotoxic neutrophils (FIG. 18A). We also identified that proteins Galectin-3 and Neuropilin-1 were positively correlated with panobinostat therapeutic response. While Galectin-3 was present on non-proliferating tumor cells at the border of the affected area; ~85% of Neuropilin-1 positive cells were cytotoxic neutrophils (as defined by Myeloperoxidase (MPO) staining; FIG. 19B). The phenotype was observed in both mouse models of triple negative and HER2+ BC (not shown) suggesting the panobinostat-mediated effects are induced independently of BC subtype. Blocking Galectin-3 cells and neutrophils in the assay area decreased panobinostat-mediated tumor killing indicating the functional role of these cells in panobinostat mechanism of action (FIG. 19C).

Preliminary results suggest that Neuropilin-1 cells recruited to panobinostat-release site are antitumor neutrophils. We hypothesize that therapeutic interventions further enhancing the antitumor capacity of the recruited neutrophils will synergize with panobinostat mechanism of action in setting baseline immune state for effective immune checkpoint blockade response and that increased Neuropilin-1 in tumors will be the early predictive biomarker discriminating the ICB benefit.

Our systems may be used to identify if polarization of panobinostat-recruited neutrophils towards N1 phenotype further increases the apoptosis at the drug-releasing well. A systematic approach may be taken to perform perturbation studies using small molecule inhibitors, blocking antibodies and cytokines known to target N1 antitumor neutrophil polarization in tumors (Fridlender et al., *Cancer Cell* 16:183-94, 2009; Andzinski et al., *Int J Cancer.* 138:1982-93, 2016). Specific focus can be placed on TGFβ and hypoxia inhibitors, and type I IFN and ICAM-1 targeted compounds. A total of 6 MMTV-PyMT mice can be used to test 35 interventions (controls included) in 4 replicates. Apoptosis measurements as defined by our preliminary data will quantitatively evaluate the contribution of each factor in inhibiting or increasing intratumoral killing. Different baseline panobinostat concentrations can be used to address assay sensitivity; while sequential drug release will determine the optimal schedule of the combination therapy. Adding anti-Neuropilin-1 antibody in the set of interventions will test the functional role of Neuropilin-1 in panobinostat mediated tumor killing.

The systems and methods may also be used to determine if Neuropilin-1 is the novel biomarker of anti-tumor neutrophils.

Apoptosis measurements discussed above can be coupled with the established multiparametric single cell analysis. Immunohistochemical staining can be extended and will correlate the rate of Neuropilin-1 positive cells gated on cytotoxic neutrophils with antitumor (ICAM-1; Fridlender et al., *Cancer Cell* 16:183-94, 2009) and protumor (CXCR2; Hagerling & Werb, *Semin Immunol.* 28:197-204, 2016) phenotypes. Following steps can sort Neuropilin-1 positive and Neuropilin-1 negative neutrophils from tumor-bearing mice and compare their gene expression profiles for N1 and N2 markers using real-time RT-PCR. The same neutrophil populations can be tested in their potential to delay tumor growth, which will definitely address their anti-tumor potential.

Further steps can determine if panobinostat combination approach balancing tumor associated neutrophils towards N1 phenotype improves the efficacy of ICB in breast cancer. The vaccination with panobinostat-killed tumor cells validated apoptosis to be immunogenic, however, the protection against tumor development was not shown to be long-lasting (FIG. 19A)—suggesting resistance mechanisms have been induced. We hypothesize that polarization of TANs, recruited by panobinostat, towards N1 phenotype will further increase tumor killing, which is the essential component of effective anti-tumor immunity (Patel & Minn, *Immunity.* 48:417-33, 2018). The top two candidates from AIM1 can be tested in whole animal studies in their ability to synergize with panobinostat to increase intratumoral CD8 T cell infiltrate and to improve the efficacy of ICB in mammary carcinoma. The treatment response, measured by tumor growth, will be correlated with Neuropilin-1 histopathological signature to test if this biomarker has early predictive value to stratify ICB benefit.

Research Design and Methods

Perturbation study to determine the role of antitumor neutrophils in panobinostat-induced cell death: Upon entering tumor microenvironment, neutrophils acquire different activation state referred to as "polarization" of neutrophils towards a tumor promoting or an antitumor phenotype (Hagerling & Werb, *Semin Immunol.* 28:197-204, 2016). Specifically, TANs phenotype is modulated by cytokines Interferon beta (IFNβ) that induces antitumor state (Andzinski et al., *Int J Cancer.* 138:1982-93, 2016); while Transforming growth factor beta (TGFβ) differentiates neutrophils towards a protumorigenic phenotype (Fridlender et al., *Cancer Cell* 16:183-94, 2009). N1 neutrophils are characterized by high tumor killing capacity, high expression of Intracellular Adhesion Molecule 1 (ICAM-1), Tumor necrosis factor alpha (TNFα) and high neutrophils extracellular traps (NETs) presence (Fridlender et al., *Cancer Cell* 16:183-94, 2009; Shaul et al., *Oncoimmunology* 5:1-14, 2016; Andzinski et al., *Int J Cancer.* 138:1982-93, 2016). N2 TANs display general downregulation of genes involved in immune response and MHCi antigen-presentation, and increased Vascular endothelial growth factor (VEGF), CXC motif chemokine receptor 2 (CXCR2), and Arginase expression, which is known to inhibit T-cell effector functions (Shaul et al., *Oncoimmunology* 5:1-14, 2016; Hagerling & Werb, *Semin Immunol.* 28:197-204, 2016). In tumor development, neutrophils initially recruited during the early stage have an anti-tumor phenotype but they become more protumorigenic with disease progression (Hagerling & Werb, *Semin Immunol.* 28:197-204, 2016; Albrengues et al., *Science* 361(6409), 2018, doi:10.1126/science.aao4227).

Perturbation studies can address the N1/N2 neutrophil polarization in combination with panobinostat, which induced neutrophils recruitment to the drug-releasing site, using devices loaded with combination of compounds as designed in the Table 1. In some examples, two different concentrations of panobinostat can be used (20%—original concentration; and lower ~12.5% of drug in PEG). The lower concentration will be preferred in wells, where the added compound is expected to enhance panobinostat mediated-tumor killing at the reservoir. This to obtain better sensitivity. We have recently described the optimal loading the of proteins that mediate physiologically relevant effects (Watson et al., *Cell Syst* 1-14, 2018, doi.org/10.1016/j.cels.2018.02.001). 10% of protein in the reservoir and 2-day incubation, maintaining the half-life of the protein, will be used in this study (FIG. 19C). Small molecule inhibitors will be combined with panobinostat in 1:1 ratio. Stoichiometry is be conserved in control (single compound) wells. Results with the same panobinostat baseline concentration will be compared and significant differences in CC3 signal will be determined by unpaired two-tailed t-test such as described previously (FIG. 18B and Watson et al., *Cell Syst* 1-14, 2018, doi.org/10.1016/j.cels.2018.02.001). Devices can be loaded with compounds in 6 replicates. In the microdevice implantation studies, we prefer to use mouse models with spontaneously developing tumors to account for all steps of immune-editing (Dunn et al., *Annu Rev Immunol* 22:329-60, 2004), such as the MMTV-PyMT tumor, which has better penetrance. At least two devices can be implanted to one MMTV-PyMT mouse as tumor development is multi-focal (Guy et al., *Mol Cell Biol.* 12:954-61, 1992). Considering 33% replicate loss due to the technical issues (device implanted close to the tumor border, necrotic or cystic area) final analysis would involve 6*0.66=4 assay areas for each condition.

Previously we have identified that n=3/condition is sufficient to obtain significant differences (FIG. 18B and Watson et al., *Cell Syst* 1-14, 2018, doi.org/10.1016/j.cels.2018.02.001). A total of 6 MMTV-PyMT mice can be used to test 35 interventions (controls included) in 4 replicates, using a total of 140 mice to address the hypothesis with the same set of interventions using standard, whole animal, approaches. Of note, the devices should be implanted and extracted at the same time of the day as neutrophils are released form bone marrow depending on circadian rhythm (Casanova-Acebes et al., *Cell*. 153:1025-35, 2013). In the perturbation study, we expect recombinant proteins IFNβ, ICAM-1 (Fridlender et al., *Cancer Cell* 16:183-94, 2009; Andzinski et al., *Int J Cancer.* 138:1982-93, 2016), TGFβ inhibitors (Fridlender et al., *Cancer Cell* 16:183-94, 2009; Shaul et al., *Oncoimmunology* 5:1-14, 2016), and hypoxia inhibitors (Casbon et al., *Proc Natl Aced Sci USA* 112:E566-75, 2015) to enhance the panobinostat-mediated killing. Inversely, blocking Galectin-3, neutrophils (already shown in FIG. 18C), Neuropilin-1 and IFNβ signaling should decrease the CC3 signal if N1 neutrophil polarization is essential for panobinostat-mediated tumor killing (FIG. 20). The extent to which apoptosis is diminished is quantified and compared to the negative (PEG) and positive (panobinostat only) control. The sequential drug release (blocking compound on top of panobinostat and vice versa) will define the sequence of events critical to mediate the most robust tumor killing. This drug treatment sequence will be then used in AIM 3 in whole animal studies testing the combination approach to improve PD-1 blockade efficacy. Use of anti-Neuropilin-1 antibody in the intervention panel will determine the functional role of Neuropilin-1 in panobinostat mediated tumor killing.

Extended multivariate single cell analysis to validate N1 polarization at the drug releasing well: Up to 15 slides can be sectioned from tumors at each drug-releasing well. An adjacent slide from the steps above can be stained with the established multiplex immunohistochemistry staining with preferential focus on myeloid immune cells. The mIHC is extended to interrogate the N1 neutrophil phenotypes in the assay area. Specifically, ICAM-1 and NETs are expected to be enriched in the assay area (Andzinski et al., *Int J Cancer.* 138:1982-93, 2016; Patnaik et al., *Cancer Discov.* 7:750-65, 2017; Brinkmann et al., *Front Immunol.* 7, 2016); while CXCR2 should be excluded on neutrophils under conditions where N1 polarization was induced. N1 profile can then be measured by single cell multivariate analysis as defined previously (FIG. 18C and Tsujikawa et al., *Cell Rep* 19:203-17, 201) and correlated with % of Neuropilin-1 high neutrophils in the assay area. These studies address the possibility of Neuropilin-1 to be a novel biomarker of antitumor neutrophils through quantitative measure after local assessment.

Anti-tumor N1 phenotype measurements of sorted Neuropilin-1 positive cells: We observed that Neuropilin-1-high cells preferentially co-localized with MPO positive cytotoxic neutrophils at the panobinostat drug-releasing well (FIG. 19C). We treated the LPA3 mice (model of ER+ breast cancer; Liu et al., *Cancer Cell*. 15:539-50, 2009) with panobinostat systemically and observed increased Neuropilin-1 infiltrate inside the tumor bed 3 days after drug application (FIG. 21A). To obtain enough Neuropilin-1 neutrophils from tumor bearing mice, this model may be used and sort cells for downstream analysis. Finally, comparison is made to two sorted populations (high, low) from panobinostat-treated mice and one (Neuropilin-1 low) from vehicle treated control to differentiate the drug-effect on neutrophils in general. In the first study, gene expression is measured for N1 (ICAM-1, TNFα, CCL3) and N2 (VEGF, CCL2, CCL5, Arginase) markers using real-time RT-PCR (Fridlender et al., *Cancer Cell* 16:183-94, 2009). In the second study, measurements are taken of the anti-tumor properties of different neutrophil populations in delaying the rate of tumor growth when injected with tumor cells into syngeneic mice. The cells will be injected in 1:1 ratio (Shaul et al., *Oncoimmunology* 5:1-14, 2016). Injection of 60,000 tumor cells orthotopically into mammary fat pad is sufficient to induce 1.5 cm$^3$ tumors within 3 weeks (FIG. 21B). Based on our previous results, the minimal number of required animals to obtain significant results is n=3/group. Formula $n=((sd_{group1}^2+Sd_{group2}^2)*Z)$ $(mean_{group1}-mean_{group2})^2$; Z=13 for α=0.05 and β=0.05 (tabular parameters) was used for the power calculation. We expect Neuropilin-1-high cells to have increased expression of markers of antitumor neutrophils. Neuropilin-1-high neutrophils co-injected with tumor cells should significantly delay the tumor growth if being N1 antitumor neutrophils.

Drug combination testing to trigger anti-tumor immunity and to improve PD-1 blockade efficacy: The top two candidates enhancing panobinostat mediated tumor killing (from AIM 1) can then be tested in whole animal studies, such as with small molecule inhibitors and FDA approved drugs. Schedule of drug administration may be defined by optimal sequential release assessment from AIM1. The combination approach is tested in its potential to i) delay tumor growth and ii) metastatic dissemination to lungs, iii) and to significantly enhance the efficacy of anti-PD-1 therapy as compared to single treatments. Long-term disease control is expected in the triple combination group. Groups are checked for signs of toxicity and weight loss. Neuropilin-1 will be measured early (day 3) to correlate the disease response with this in situ biomarker. Cytotoxic T cell infiltrate will be measured late (day 10) (Luo et al., *Nat Commun* 1-11, 2018, doi.org/10.1038/s41467-017-02630-w) after the treatment initiation to identify if anti-tumor immunity is induced. We expect significant increases in the described phenotypes in the combination approach as compared to single treatments and control. Studies may be performed using the orthotopically induced LPA3 mouse model (FIG. 21B). As defined above, three animals are used per groups for tumor growth rate measurements; plus three animals will be added for early- and late-tumor extraction for IHC staining. This part of the project will identify optimal treatment combination and schedule to improve the success of immunotherapy in breast cancers. The outcomes (by tumor volume measurements) are then correlated with Neuropilin-1 increase determining if this protein can serve as early predictive biomarker to stratify ICB benefit.

Alternatively, MNA system can be used to search for other drugs that synergize with panobinostat therapeutic response and/or antagonize processes mediating resistance to therapy. E.g. other TGFβ inhibitors (DZNep and Losartan) or cytokines (HGF; Finisguerra et al., *Nature*. 522:349-53, 2015). To identify novel therapeutic targets, we might combine the microdevice technology with gene expression profiling with RNA-seq.

Such studies raise novel insights—comprehensive direct evidence—on the interface of dying tumor cells and tumor immune microenvironment, explaining the immuno-modulatory function of panobinostat in mammary carcinoma and the role of Neuropilin-1 in this process. The studies address the possibility that therapies targeting neutrophil polarization might be beneficial to enhance the success of immune checkpoint blockade in breast cancer. The robust nature of the MNA system will allow us to rapidly identify rational combination strategies. These discoveries might result in a direct clinical application, where knowing the proper schedule and sequencing of the effective combination treatment approach is essential. Considering the fact that panobinostat-mediated effects were similar in different breast cancer subtypes, the identified mechanisms may benefit a very large number of breast cancer patients.

Example 4: An Exemplary Procedure for Ex Vivo Tumor/Tissue Biopsy Core Culture

1. Fabricate a dual cylinder PDMS scaffold system.
2. Inject the ECM-(like) matrix, with or without stromal cells, into the outer compartment of the dual cylinder scaffold system.
3. After the mixture (from step 2) solidifies, insert the biopsy needle containing a tumor/tissue sample in the needle bore vertically into this biomimetic scaffold inner compartment.
4. Insert the implantable microdevice into the tumor/tissue sample inside the biopsy needle, approaching from the top opening of the biopsy needle.
5. Remove the biopsy needle from the scaffold system. The modified microdevice design includes a handle that will keep the tumor/tissue sample stationary while the biopsy needle is being removed by, for example, a tweezer.
6. The tumor/tissue sample is now deployed into scaffold system with the microdevice directly exposed to the in vivo mimicking microenvironment.
7. Submerge the scaffold system with deployed tissue/microimplant in a standard culturing medium and put to a tissue culture incubator (5% $CO_2$, 37° C.). The PDMS elastomer is gas and vapor permeable and thus maintains pH and humidity. Additionally, such microfluidic/PDMS manifold generates a miniaturized environment that by default concentrates the soluble and ECM factors produced by the tumor/tissue explant and/or by the injected stromal cells (Tatárová et al., 2016).
8. In case these amounts of produced factors are not satisfactory for cell viability, will allow the soluble factors to diffuse to the inner microenvironment through the pin-size inlets/outlets in the PDMS dual cylinder scaffold system.
9. The scaffold is designed so that it can be attached to an automated or manual active microfluidic supply system that will increase the nutrient delivery and viability of the cells (Tatárová et al., 2016). Endothelial cells are expected to contract, form tubes and branching (for example, if pulsative flow is applied to, e.g., 5 inlets and 15 outlets) thus presenting complete vasculature mimicry. Timing of the supply pulsing may be adjusted depending on the tumor/tissue explant size so that it balances the nutrient delivery and washout of the cell produced stromal factors. Exemplary pulse durations of nutrient medium flow and nutrient medium diffusion into the system (flow stopped) will range between 5 s-2 hours for the flow step and 5 s-24 h for the diffusion (supply flow stopped).
10. After performing the functional drug sensitivity screen (0-28 days), the tissue may be processed for standard formalin fixed paraffin embedded histology. Alternatively, OCT or tissue clearing may be utilized for other visualization techniques.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed:

1. A method of assessing cell response to a plurality of anticancer agents, the method comprising:
   inserting into an ex vivo tissue sample an implantable drug-delivery device comprising at least 8 microwell reservoirs, and each reservoir holding one or more agents;
   incubating the ex vivo tissue sample with the inserted implantable drug-delivery device in a sustaining ex vivo environment for at least 12 hours and no more than 30 days;
   formalin fixing and paraffin embedding the ex vivo tissue sample with the drug-delivery device in place;
   analyzing composition or molecular status of tissue or cells adjacent each reservoir; and
   comparing the effects of each agent on adjacent tissue or cells,
   wherein one or more of the plurality of anticancer agents is in solid or semi-solid form.

2. The method of claim 1, wherein the cell is a tumor cell, the tissue sample is a tumor tissue sample, and at least one of the agents is an anti-cancer agent.

3. The method of claim 2, wherein at least one agent is an anti-cancer agent, a carcinogen, a growth factor, an siRNA, a small molecule, a cytokine, a chemokine, an antibody, or a radio-labeled compound.

4. The method of claim 1, wherein analyzing the composition or the molecular status of tissue or cells adjacent each reservoir comprises one or more of immunohistochemistry (IHC), immuno-detection, in situ RNA hybridization, sequencing, protein isolation, nucleic acid isolation, microscopic observation, or staining.

5. The method of claim 1, wherein at least one microwell reservoir contains two different agents.

6. The method of claim 5, wherein each microwell reservoir contains a different agent, a different mixture of agents, and/or a different dosage of agents.

7. The method of claim 1, wherein the sustaining ex vivo environment comprises a dual cylinder vapor-permeable microfluidics manifold device comprising: an inner tube configured with a plurality of pinholes; and an outer tube of larger mean diameter than the inner tube, the outer tube configured with a plurality of pinholes.

8. A method for determining efficacy of a compound in a tissue comprising:
   inserting into an ex vivo tissue sample outside of an organism an implantable microdevice comprising:
      a cylindrical support structure having microwells on a surface of or formed within the support structure, the microwells each containing and releasing after implantation a microdose of one or more active agents selected from therapeutic, prophylactic, and/or diagnostic agents;
      a microdose of one or more active agents in at least one microwell; and
      compound release mechanism comprising a polymeric matrix for controlling the release of the one or more active agents from the microwell;
   wherein the microdevice is configured to release the one or more active agents from the microwells to separate and discrete areas of tissue adjacent to each microwell without overlap between the discrete areas;
   incubating the ex vivo tissue sample with the inserted implantable microdevice in a sustaining ex vivo environment for at least 12 hours and no more than 30 days to produce agent-exposed tissue; and subjecting the agent-exposed tissue to multiplex immunohistochemistry (mIHC) analysis to determine the presence of Galectin-3 and Neuropilin-1, where presence or upregulation of either or both of Galectin-3 and Neuropilin-1 indicates the compound is effective.

9. The method of claim 8, wherein the tissue sample is a tumor tissue sample, and at least one of the agents is an anti-cancer agent.

10. The method of claim 8, wherein at least one agent is an anti-cancer agent, a carcinogen, a growth factor, an siRNA, a small molecule, a cytokine, a chemokine, an antibody, or a radio-labeled compound.

11. The method of claim 8, wherein analyzing the composition or the molecular status of tissue or cells adjacent each reservoir comprises one or more of immunohistochemistry (IHC), immuno-detection, in situ RNA hybridization, sequencing, protein isolation, nucleic acid isolation, microscopic observation, or staining.

12. The method of claim 8, wherein at least one microwell reservoir contains two different agents.

13. The method of claim 8, wherein each microwell reservoir contains a different agent, a different mixture of agents, and/or a different dosage of agents.

14. A method of determining efficacy of an anti-cancer agent to treat a solid tumor, comprising:
    administering the anti-cancer agent, to a subject having a solid tumor, for a period of at least 2 days;
    subsequent to administering the anti-cancer agent:
        analyzing blood from the subject to determine presence and/or quantity of circulating galectin; and
        analyzing a tumor tissue sample from the solid tumor of the subject to determine the presence and/or quantity of neuropilin;
    wherein an increase in galectin and/or neuropilin compared to a control indicates that the anti-cancer agent is effective to treat the solid tumor.

15. The method of claim 14, wherein the solid tumor is a breast cancer tumor.

16. A method of assessing cell response to a plurality of anticancer agents, the method comprising:
    inserting into an ex vivo tissue sample an implantable drug-delivery device comprising at least 8 microwell reservoirs, and each reservoir holding one or more agents;
    incubating the ex vivo tissue sample with the inserted implantable drug-delivery device in a sustaining ex vivo environment for at least 12 hours and no more than 30 days;
    formalin fixing and paraffin embedding the ex vivo tissue sample with the drug-delivery device in place;
    analyzing composition or molecular status of tissue or cells adjacent each reservoir; and
    comparing the effects of each agent on adjacent tissue or cells,
    wherein the sustaining ex vivo environment comprises a dual cylinder vapor-permeable microfluidics manifold device comprising: an inner tube configured with a plurality of pinholes; and
    an outer tube of larger mean diameter than the inner tube, the outer tube configured with a plurality of pinholes.

* * * * *